US012156909B2

(12) United States Patent
Philip et al.

(10) Patent No.: US 12,156,909 B2
(45) Date of Patent: Dec. 3, 2024

(54) REVERSE PEPTIDE VACCINE

(71) Applicant: Emergex Vaccines Holding Limited, Oxfordshire (GB)

(72) Inventors: Ramila Philip, Sparks, NV (US); Richard David Perrins, Oxfordshire (GB); Xiaofang Huang, Jenkintown, PA (US); Thomas Rademacher, Oxfordshire (GB); Christopher Upton, Victoria (CA)

(73) Assignee: Emergex Vaccines Holding Limited, Oxfordshire (GB)

(*) Notice: Subject to any disclaimer, the term of this patent is extended or adjusted under 35 U.S.C. 154(b) by 634 days.

(21) Appl. No.: 17/054,104

(22) PCT Filed: May 20, 2019

(86) PCT No.: PCT/GB2019/051386

§ 371 (c)(1),
(2) Date: Nov. 9, 2020

(87) PCT Pub. No.: WO2019/220150

PCT Pub. Date: Nov. 21, 2019

(65) Prior Publication Data

US 2021/0299241 A1 Sep. 30, 2021

Related U.S. Application Data

(60) Provisional application No. 62/673,647, filed on May 18, 2018.

(51) Int. Cl.

*A61K 39/145* (2006.01)
*A61K 39/12* (2006.01)
*A61P 31/16* (2006.01)
*C07K 14/005* (2006.01)
*C12Q 1/70* (2006.01)

(52) U.S. Cl.

CPC ............ *A61K 39/145* (2013.01); *A61K 39/12* (2013.01); *A61P 31/16* (2018.01); *C07K 14/005* (2013.01); *C12Q 1/70* (2013.01); *C12N 2760/14134* (2013.01); *C12N 2760/14234* (2013.01); *C12N 2760/16122* (2013.01); *C12N 2760/16134* (2013.01); *C12N 2770/24134* (2013.01)

(58) Field of Classification Search

None
See application file for complete search history.

(56) References Cited

U.S. PATENT DOCUMENTS

| | | | | |
|---|---|---|---|---|
| 9,205,144 | B2 * | 12/2015 | Brusic | G01N 33/505 |
| 11,273,216 | B2 | 3/2022 | Philip | |

FOREIGN PATENT DOCUMENTS

| | | | |
|---|---|---|---|
| WO | 94/09035 | A1 | 4/1994 |
| WO | WO 1994/09035 | | 4/1994 |
| WO | 2002/32404 | A2 | 4/2002 |
| WO | 2006/037979 | A2 | 4/2006 |
| WO | 2007/015105 | A2 | 2/2007 |
| WO | 2007/122388 | A2 | 11/2007 |
| WO | 2013/034726 | A1 | 3/2013 |

OTHER PUBLICATIONS

Clifford et al., Virology Journal 2009, 6:198 (Year: 2009).*
Ding et al. (Int J Nanomedicine, vol. 12, pp. 5239-5254 (Year: 2017).*
Pennock et al., Trends in Immunology, vol. 37, No. 3, pp. 170-180 (Year: 2016).*
Search Report and Written Opinion issued by the Intellectual Property Office of Singapore in corresponding Singapore Patent Application No. 11202011122X dated Jan. 7, 2022.
Clifford et al., "Evidence for a novel gene associated with human influenza A viruses", *Virol J.*, 6:198, 2009.
Reemers et al., "Identification of novel avian influenza virus derived CD8+ T-cell epitopes", *PLoS One*, 7(2):e31953, 2012.
Zhong et al., "Genome-wide characterization of a viral cytotoxic T lymphocyte epitope repertoire", *J Biol Chem.*, 278(46):45135-44, 2003.
Clifford et al., "Evidence for a novel gene associated with human influenza A viruses", Virology Journal, Biomed Central, London, GB, vol. 6, No. 1, Nov. 16, 2009 (Nov. 16, 2009), p. 198.
Database UniProt [Online] UNIPROT: Q0R5M6, Sep. 5, 2006.
Hickman et al., "Influenza A Virus Negative Strand RNA is Translated for CD8+ T Cell Immunosurveillance", bioRxiv preprint first posted online Feb. 7, 2018, https://doi.org/10.1101/261966.
Meziere et al., "In Vivo T Helper Cell Response to Rretro-Inverso Peptidomimetics" J. Immunol. 159, (1997) 3230-3237.
Tumpey et al., "Characterization of the Reconstructed 1918 Influenza Pandemic Virus", Science, vol. 310, Oct. 7, 2005.
Wen et al., "Dengue virus-reactive CD8+ T cells mediate cross-protection against subsequent Zika virus challenge", Nature Communications, 8:1459, Nov. 13, 2017.
Yang et al., "Uncovering the Potential Pan Proteomes Encoded by Genomic Strand RNAs of Influenza A Viruses", PLOS ONE, vol. 11, No. 1, Jan. 13, 2016, page e0146936.
Zhirnov et al., "Structural and evolutionary characteristics of HA, NA, NS and M genes of clinical influenza A/H3N2 viruses passaged in human and canine cells", Aug. 1, 2009 (Aug. 1, 2009), Journal of Clinical Virology, vol. 45, No. 4, p. 322-333.
Zhong et al., "Genome-wide Characterization of a Viral Cytotoxic T Lymphocyte Epitope Repertoire", The Journal of Biological Chemistry, vol. 278, No. 46, pp. 45135-45144 (2003).
Badovinac, Valdimir P. et al., "Accelerated CD8+ T-Cell Memory and Prime-Boost Response after Dendritic-Cell Vaccination"; Nature Medicine, vol. 11, No. 7; pp. 748-756; Jul. 2005.

* cited by examiner

*Primary Examiner* — Shanon A. Foley
*Assistant Examiner* — Myron G Hill
(74) *Attorney, Agent, or Firm* — Norton Rose Fulbright US LLP

(57) ABSTRACT

The invention relates to vaccine compositions comprising peptides encoded by an open reading frame (ORF) encoded by at least part of the genome of a ssRNA virus in the opposite sense to positive sense RNA capable of translation, and the use of such compositions for the treatment and prevention of viral infection.

21 Claims, 14 Drawing Sheets

Specification includes a Sequence Listing.

Fig. 4 (Cont. I)
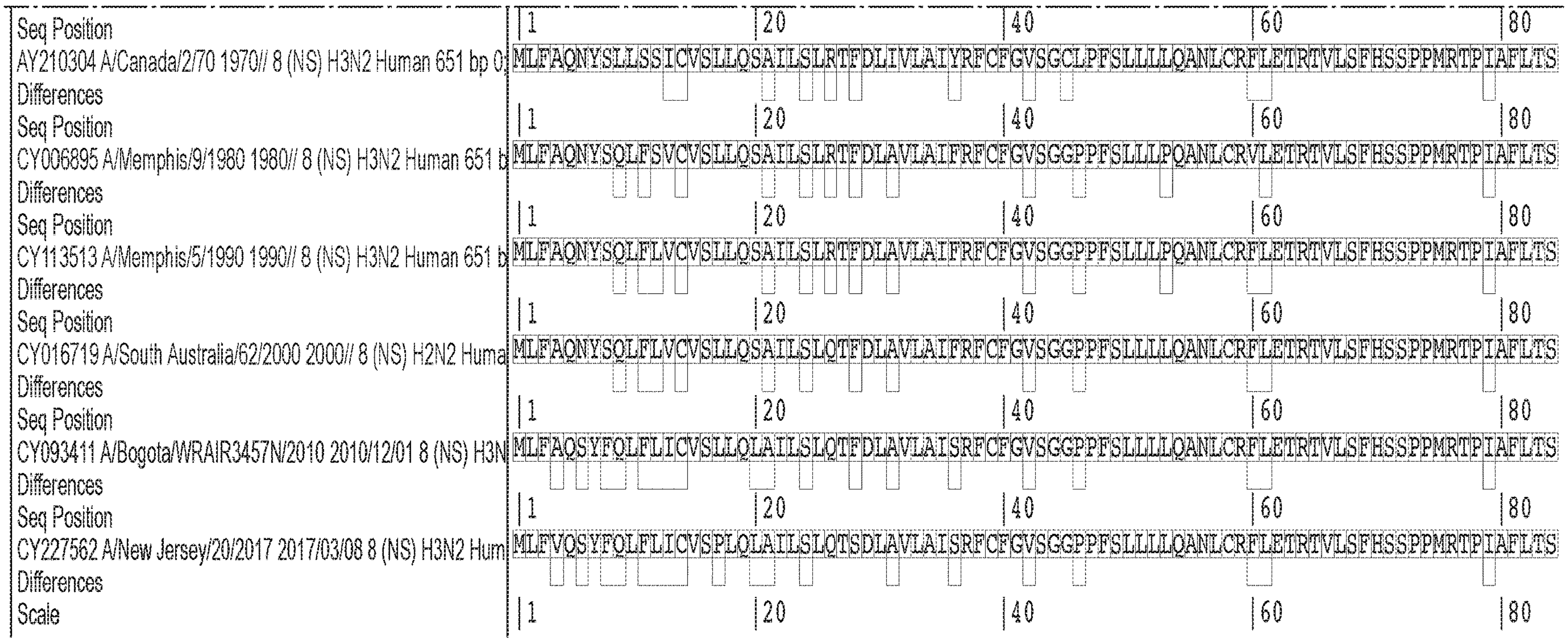

Fig. 4 (Cont. II)
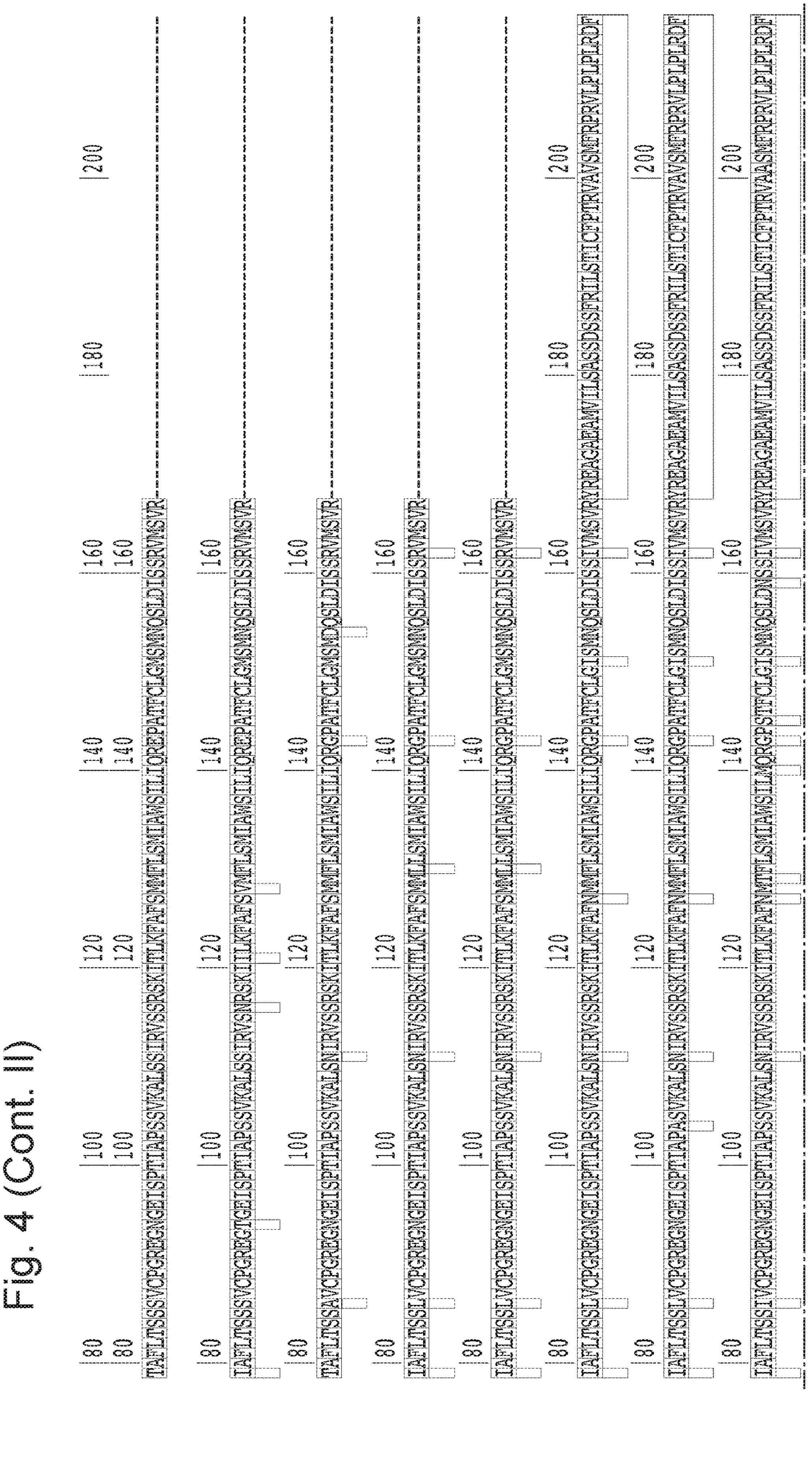

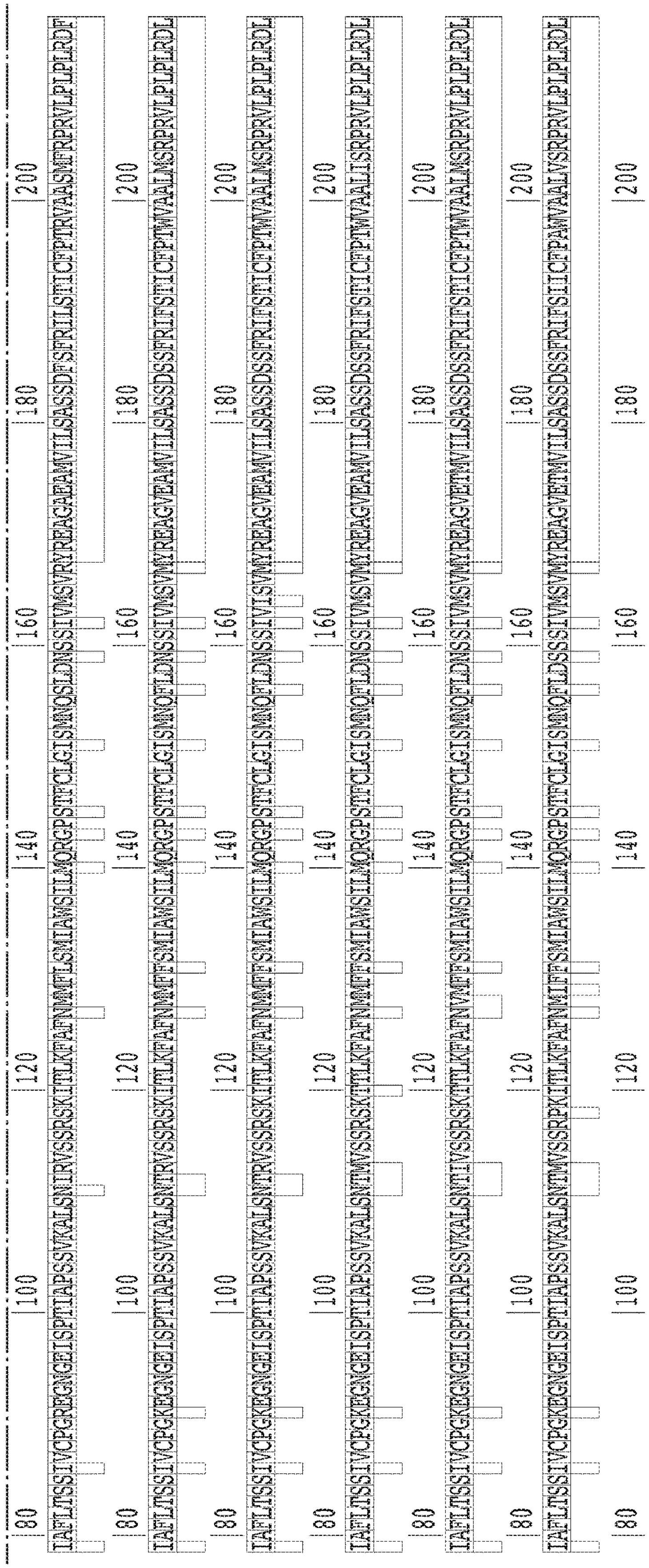
Fig. 4 (Cont. III)

REVERSE PEPTIDE VACCINE

CROSS-REFERENCE TO RELATED APPLICATIONS

This application is a national phase application under 35 U.S.C. § 371 that claims priority to International Application No. PCT/GB2019/051386, filed May 20, 2019, which claims priority to U.S. Provisional Patent Application Ser. No. 62/673,647, filed May 18, 2018, both of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Nov. 9, 2020, is named Sequence_Listing.txt and is 36,578 bytes in size.

FIELD OF THE INVENTION

The invention relates to vaccine compositions comprising peptides encoded by an open reading frame (ORF) encoded by at least part of the genome of a ssRNA virus in the opposite sense to positive sense RNA capable of translation, and the use of such compositions for the treatment and prevention of viral infection.

BACKGROUND TO THE INVENTION

Influenza is a significant global health problem, infecting up to 20% of the world's population annually, causing up to 5 million cases of severe illness and >300,000 deaths worldwide. In the U.S. alone, an estimated >30,000 deaths and nearly 300,000 hospitalizations are attributed to influenza infection each year. With the recent appearance of new, severe and potentially recurrent seasonal disease, widespread vaccination campaigns that reduce the incidence of influenza-induced pneumonia are being encouraged by the World Health Organization. Effectively reducing the incidence of influenza will require continued intense surveillance, increased use of currently available influenza vaccines, and availability of alternative vaccines and antiviral medications that can provide broader protection against shift-and-drift strains of influenza. Successful influenza vaccination campaigns can have enormous societal and economic impact.

The immune response to influenza is governed by both innate and adaptive immunity. The innate immune response to influenza limits initial viral replication but is relatively non-specific. Efficient clearance of influenza virus requires a robust adaptive immune response. Conventional influenza vaccines aim to elicit such an adaptive immune response by inducing humoral immunity to influenza virus. Humoral immunity as mediated by secretory IgA and IgM antibodies provides protection against the establishment of initial infection, while IgG antibodies neutralize newly replicating virus in established infection. CD4+ T cell responses may assist in the development of humoral immunity and have roles in isotype-switching to IgG and in the generation of higher affinity antibodies and CTL memory. This is emphasised by the finding that hemagglutinin (HA)-specific CD4+ T cells proliferate following influenza vaccination in humans and aid the development of heterosubtypic influenza antibody responses.

Despite their ability to induce humoral immunity, conventional influenza vaccines are not completely protective. This is due, at least in part, to the occurrence of antigenic variations. Furthermore, it is thought that cell mediated immunity may play a key role in protecting against influenza. CD8+ cytotoxic T lymphocytes (CTLs) mediate viral clearance and have been shown to have cross-reactive responses to different subtypes of influenza A virus. This may help to explain the relative paucity of disease among individuals that are older and have been vaccinated against influenza or have been previously exposed to influenza virus multiple times.

Influenza vaccines currently on the market are updated yearly. Their design is based on annual WHO strain recommendations, and they are manufactured prior to the beginning of an influenza season or pandemic. Current vaccines for influenza induce a protective humoral immune response against the HA and neuraminidase (NA) glycoproteins on the virion surface. However, viral HA and NA glycoproteins are highly susceptible to frequent and unpredictable antigenic drift and less frequent, but more severe, shift mutations, which result in loss of antibody recognition. This necessitates the frequent development of new vaccines to match the current viral serotype(s) infecting the human population. Accordingly, existing influenza vaccines are costly to produce and are unlikely to be protective against novel strains that emerge mid-season (e.g. 2009 H1N1 swine flu, H5N1, H7N9). Moreover, these vaccines are designed to provide antibody-based protection, with little consideration given to the induction of cell mediated immunity that is important for eliminating virus-infected cells from the body.

Several quadrivalent vaccines (protecting against two influenza A and two influenza B viruses) have been approved by the FDA. While these vaccines provide broader protection than conventional influenza vaccines, they are still unlikely to be protective against novel strains that emerge mid-season or emergent pandemic strains, and are costly to produce. Furthermore, like conventional influenza vaccines, the quadrivalent vaccines are not designed to elicit cell mediated immunity that is important for eliminating virus-infected cells from the body.

A "universal" influenza vaccine providing broad protection against all seasonal influenza strains and pandemic strains for years, if not a whole lifetime, is therefore desirable. Development of an effective universal influenza vaccine would lessen fears of future influenza pandemics and would be more cost-effective than developing, manufacturing and administering annual seasonal influenza vaccines as is the current practice.

SUMMARY OF THE INVENTION

The present invention relates to a vaccine composition comprising an immunogenic peptide encoded by an open reading frame (ORF) encoded by at least part of the genome of a ssRNA virus, such as influenza virus, in the opposite sense to positive sense RNA capable of translation. The immunogenic peptide comprises an epitope that is capable of recognition by a CD8+ T cell.

The present inventors have surprisingly identified a number of peptides that are presented by MHC class I molecules on cells infected with influenza virus and that are encoded by an ORF encoded by part of the negative, genomic strand of influenza virus segment 8. The ORF is widely conserved amongst human influenza viruses and is therefore thought to confer a selective advantage to such viruses. Including one or more peptides encoded by the conserved ORF in a vaccine composition may confer protective capability against multiple human influenza virus strains, overcoming the problems caused by their tendency to antigenic shift and drift. Including a plurality of such peptides, each capable of binding to a different HLA supertype, in the vaccine composition may provide a broad-spectrum vaccine that is effective in individuals having different HLA types.

The present inventors consider that cells infected with other ssRNA viruses, such as filoviruses or flaviviruses, may also present peptides that are encoded by a conserved ORF encoded by part of the genome in the opposite sense to positive sense RNA capable of translation on their MHC class I molecules. Including one or more of these peptides in a vaccine composition may confer protective capability against multiple virus species, strains or serotypes, providing cross-protection within a virus family.

Accordingly, the present invention provides a vaccine composition comprising an immunogenic peptide comprising a CD8+ T cell epitope from a polypeptide encoded by an open reading frame (ORF) encoded by at least part of the genome of a ssRNA virus in the opposite sense to positive sense RNA capable of translation.

The present invention further provides:

a method of preventing or treating a viral infection, comprising administering the vaccine composition of the invention to an individual infected with, or at risk of being infected with, an ssRNA virus;

a method of identifying an immunogenic peptide comprising a CD8+ T cell epitope from an ORF encoded by at least part of the genome of a ssRNA virus in the opposite sense to positive sense RNA capable of translation by:

(a) identifying an ORF encoded by at least part of the genome of a ssRNA virus in the opposite sense to positive sense RNA capable of translation;

(b) predicting the sequence of the polypeptide encoded by the ORF; and (c) assessing whether a peptide that binds a MHC Class I molecule comprises a sequence present in the predicted sequence, thereby identifying an immunogenic peptide comprising an epitope that is capable of recognition by a CD8+ T cell;

an immunogenic peptide comprising a CD4+ T cell epitope from a polypeptide encoded by an ORF encoded by at least part of the genome of a ssRNA virus in the opposite sense to positive sense RNA capable of translation; and a method of determining the pandemic potential of an influenza A virus, the method comprising the steps of: (i) identifying a first ORF encoded by at least part of segment 8 of the genome of the influenza A virus in the opposite sense to positive sense RNA capable of translation; (ii) determining the number of codons comprised in the first ORF; and (iii) comparing the number of codons comprised in the first ORF to the number of codons comprised in a second ORF encoded by at least part of segment 8 of the genome of a known pandemic influenza A virus in the opposite sense to positive sense RNA capable of translation, wherein a difference in the number of codons in the first ORF compared to the second ORF is indicative of pandemic potential.

DETAILED DESCRIPTION OF THE INVENTION

Vaccine Compositions

Figure 1A:
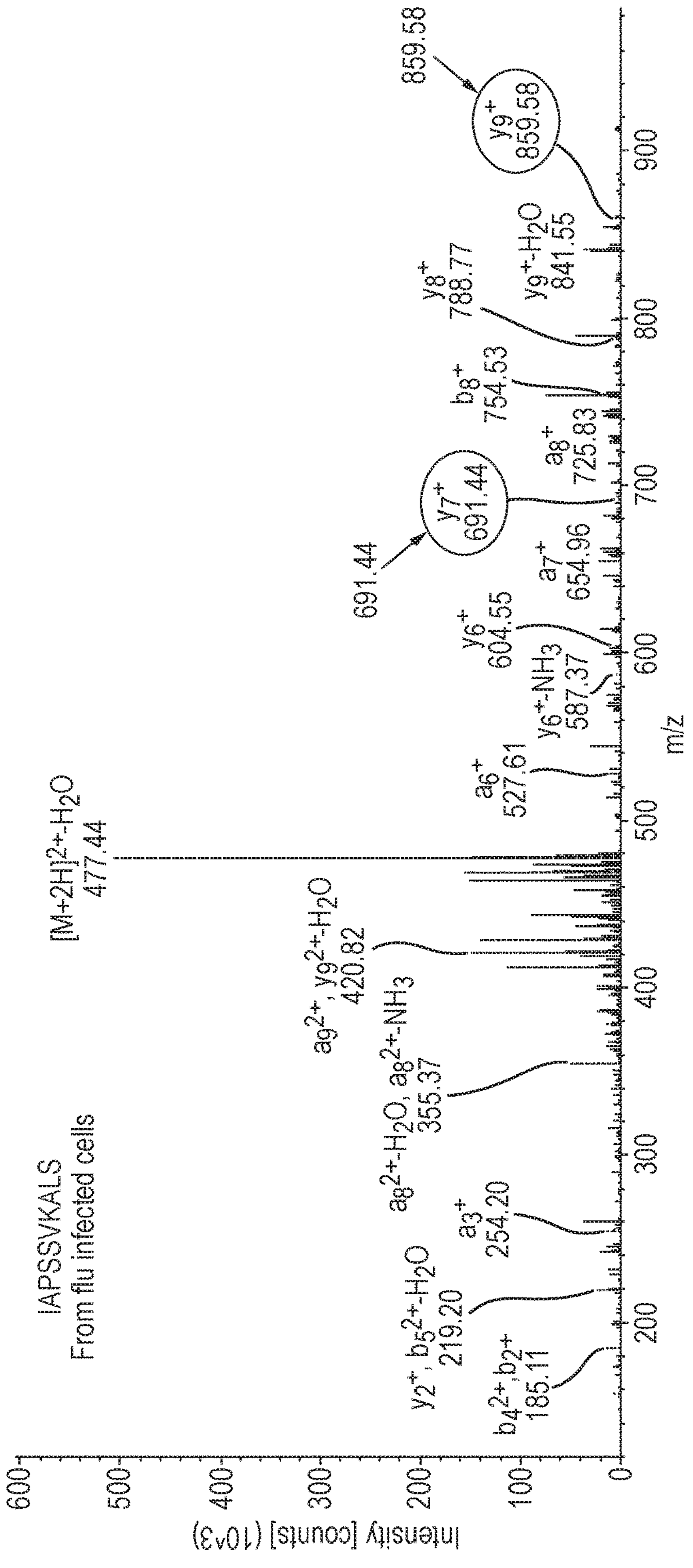
FIG. 1: Comparison of mass spectra of IAPSSVKALS from influenza virus A infected cells (A) and synthetic IAPSSVKALS peptide (B). Some typical ions in each spectrum are circled to emphasise the identity of the peptide from infected cells with that synthesised.

The present invention provides a vaccine composition comprising an immunogenic peptide comprising a CD8+ T cell epitope from a polypeptide encoded by an ORF) encoded by at least part of the genome of a ssRNA virus in the opposite sense to positive sense RNA capable of translation. This vaccine composition has a number of benefits which will become apparent from the discussion below. The key benefits are summarised here.

Firstly, the vaccine composition of the invention advantageously comprises a peptide comprising a CD8+ T cell epitope, such as an epitope set out in SEQ ID NOs: 5 to 41 and newly identified by the inventors. The vaccine composition is therefore capable of stimulating a cellular immune response (e.g. a CD8+ T cell response) against a ssRNA virus. CD8+ cytotoxic T lymphocytes (CTLs) mediate viral clearance via their cytotoxic activity against infected cells. Stimulating cellular immunity may therefore provide a beneficial defence against virus infection, such as influenza virus, flavivirus or filovirus infection.

Secondly, the ORF encoding the epitope comprised in the immunogenic peptide may be conserved between multiple viruses. The epitope itself may therefore be conserved between multiple viruses. For instance, the ORF and/or the epitope may be conserved between human influenza A viruses. The vaccine composition may therefore provide cross-protection against a plurality of human influenza A viruses. In this way, the vaccine composition of the invention is suitable for providing broad-spectrum prophylaxis against human influenza A viruses, countering the problems caused by the antigenic shift and antigenic drift to which human influenza A viruses are prone. In other words, a single vaccine composition of the invention may induce protective immunity against a wide variety of existing and emerging human influenza A viruses, reducing or eliminating the need for a new seasonal influenza vaccine to be developed each year.

The ORF and/or the epitope may be conserved between human influenza A viruses and a swine, equine and/or avian influenza A virus. In this way, the vaccine composition of the invention may prevent swine, equine and/or avian influenza A viruses becoming established in the human population. In other words, as well as protecting against existing and emerging human influenza A viruses, the vaccine composition of the invention may prevent swine, equine and/or avian influenza A viruses crossing the species divide. This may prevent the emergence of pandemic influenza A virus strains.

Thirdly, the immunogenic peptide comprised in the vaccine composition of the invention may be capable of binding to different HLA supertypes. Inclusion of multiple peptides each comprising a CD8+ T cell epitope capable of binding to a different HLA supertypes results in a vaccine composition that is effective in individuals having different HLA types. In this way, a single vaccine composition can be used to confer protection against an ssRNA virus in a large proportion of the human population. This provides a cost-effective means of controlling the incidence and spread of virus infection.

Fourthly, the polypeptide encoded by the ORF may enhance the fitness of the ssRNA virus in humans. In other words, the polypeptide may confer a selective advantage on the ssRNA virus by which it is encoded. The vaccine composition of the invention may therefore target epitopes associated with a ssRNA virus conferred with a selective advantage. The vaccine composition of the invention may therefore be well-designed to provide effective prophylaxis against emergent and/or potentially pandemic strains of a ssRNA virus.

Fifthly, the immunogenic peptide comprised in the vaccine composition of the invention may be attached to a nanoparticle, for example a gold nanoparticle. As described in more detail below, attachment to a nanoparticle reduces or eliminates the need to include an adjuvant in the vaccine composition. Thus, the vaccine composition of the invention is less likely to cause adverse clinical effects upon administration to an individual.

Reverse Peptide Vaccines

Single stranded RNA (ssRNA) viruses are classified as positive-sense or negative-sense depending on the sense or polarity of their genomic RNA. In a negative-sense ssRNA virus, the negative-sense (3' to 5') genomic RNA is complementary to the mRNA and must generally be converted to a positive-sense RNA by RNA polymerase before translation. In a positive-sense ssRNA virus, the positive-sense (5' to 3') genomic RNA can also serve as mRNA and can be translated into protein in the host cell. That is, replication of a negative-sense ssRNA virus generally occurs following transcription of the genome to form an mRNA that is complementary to the genome, and translation of the mRNA. Replication of a positive-sense ssRNA virus generally occurs following translation the genomic RNA that doubles as mRNA.

Traditionally, it has been considered that the negative sense RNA of ssRNA viruses is non-coding. However, non-canonical translation may be possible. It appears that the negative-sense genomic RNA of influenza virus may actually be capable of translation in the 5' to 3' direction, yielding different gene products to those obtained via canonical translation (i.e. 3' to 5' transcription forming a complementary mRNA, and translation of the mRNA 5' to 3'). Similarly, the RNA complementary to the genome of positive-sense ssRNA viruses may actually be translatable.

The present inventors have obtained data that demonstrates that polypeptides obtained from non-canonical translation in ssRNA viruses may comprise peptides that are recognised by the immune system of an individual infected with the ssRNA virus. For instance, a polypeptide obtained from non-canonical translation in ssRNA viruses may comprise a peptide that is capable of presentation by an MHC class I molecule and of recognition by a T cell receptor (TCR) present on a CD8+ T cell. In other words, a polypeptide obtained from non-canonical translation in ssRNA viruses may comprise a peptide that is a CD8+ T cell epitope. Such an immunogenic peptide may be administered to an individual, for instance in a vaccine composition, in order to induce an immune response against the ssRNA virus. In this way, prophylaxis and/or therapy may be achieved.

Accordingly, the present invention provides a vaccine composition that comprises an immunogenic peptide comprising a CD8+ T cell epitope from a polypeptide encoded by an ORF encoded by at least part of the genome of a ssRNA virus in the opposite sense to positive sense RNA capable of translation.

Immunogenic Peptides

An immunogenic peptide is a peptide that is capable of eliciting an immune response. The vaccine composition of the invention comprises an immunogenic peptide comprising a CD8+ T cell epitope from a polypeptide encoded by an ORF encoded by at least part of the genome of a ssRNA virus in the opposite sense to its positive sense RNA capable of translation. The vaccine composition may comprise from about one to about 50 such immunogenic peptides, such as about 2 to 40, 3 to 30, 4 to 25, 5 to 20, 6 to 15, 7, 8, 9 or 10 such immunogenic peptides.

The immunogenic peptide comprises a CD8+ T cell epitope. A CD8+ T cell epitope is a peptide that is capable of (i) presentation by a class I MHC molecule and (ii) recognition by a T cell receptor (TCR) present on a CD8+ T cell. Preferably, recognition by the TCR results in activation of the CD8+ T cell. CD8+ T cell activation may lead to increased proliferation, cytokine production and/or cyotoxic effects. Typically, a CD8+ T cell epitope is around 9 amino acids in length. A CD8+ T cell epitope may though be shorter or longer. For example, a CD8+ T cell epitope may be about 8, 9, 10, 11, 12, 13, 14 or 15 amino acids in length. A CD8+ T cell epitope may be about 8 to 15, 9 to 14 or 10 to 12 amino acids in length.

The CD8+ T cell epitope comprised in the immunogenic peptide is from a polypeptide encoded by an ORF encoded by at least part of the genome of a ssRNA virus in the opposite sense to positive sense RNA capable of translation. In other words, the CD8+ T cell epitope may, in nature, be comprised in or form part of a polypeptide encoded by an ORF encoded by at least part of the genome of a ssRNA virus in the opposite sense to positive sense RNA capable of translation. The polypeptide may be expressed on the surface of the ssRNA virus, or intracellularly within the ssRNA virus. Expression of the polypeptide by the virus may be transient i.e. the polypeptide may only be expressed by the ssRNA virus at certain points in its lifecycle and/or under certain environmental conditions. Alternatively, the ssRNA virus may have sustained expression of the polypeptide. The polypeptide may be a structural peptide or a functional peptide, such as a peptide that is involved in the metabolism or replication of the ssRNA virus. In some cases, however, the purpose and/or function of the polypeptide may be unknown.

The polypeptide that gives rise to the CD8+ T cell epitope may enhance the fitness of the ssRNA virus in humans. For example, the polypeptide may improve the survival and/or replication of the virus in a human host cell. Accordingly, the polypeptide may confer a selective advantage on the ssRNA virus. In other words, expression of the polypeptide may enable the ssRNA virus to survive and/or reproduce better than an ssRNA virus that does not express the polypeptide. In this case, the evolutionary selective process may select for viruses in which at least part of the genome encodes, in the opposite sense to positive sense RNA capable of translation, an ORF encoding the polypeptide. The ORF (and, consequently, the polypeptide) may therefore be conserved between different ssRNA viruses of a particular type. For instance, the ORF and/or the polypeptide may be conserved between different strains of Influenza A virus, or different between flaviviruses (e.g. between Zika virus and Dengue virus). The ORF (and, consequently, the polypeptide) is conserved between two or more different ssRNA viruses if there is at least 20% (such as at least 30%, at least 40%, at least 50%, at least 60%, at least 70%, at least 75%, at least 80%, at least 90%, at least 95%, at least 98% or at least 99%) identity between the ORF encoded by at least part of the genome of each virus, in the opposite sense to positive sense RNA capable of translation.

The immunogenic peptide may comprise only one CD8+ T cell epitope from a polypeptide encoded by an ORF encoded by at least part of the genome of a ssRNA virus in the opposite sense to positive sense RNA capable of translation. Alternatively, the immunogenic peptide may comprise two or more, such as three or more, four or more, five or more, six or more, seven or more, eight or more, nine or more, ten or more, fifteen or more, or twenty or more such epitopes.

As well as the CD8+ T cell epitope(s) from a polypeptide encoded by an ORF encoded by at least part of the genome of a ssRNA virus in the opposite sense to positive sense RNA capable of translation, the immunogenic peptide may comprise one or more other CD8+ T cell epitopes, one or more CD4+ T cell epitopes and/or one or more B cell epitopes. For example, the immunogenic peptide may comprise one or more, such as two or more, three or more, four or more, five or more, ten or more, fifteen or more, or twenty or more CD8+ T cell epitopes that are not a CD8+ T cell epitope from a polypeptide encoded by an ORF encoded by at least part of the genome of a ssRNA virus in the opposite sense to positive sense RNA capable of translation. The immunogenic peptide may comprise one or more, such as two or more, three or more, four or more, five or more, ten or more, fifteen or more, or twenty or more CD4+ T cell epitopes. The immunogenic peptide may comprise one or more, such as two or more, three or more, four or more, five or more, ten or more, fifteen or more, or twenty or more B cell epitopes.

Preferably, the immunogenic peptide comprises one or more of the sequences set out in SEQ ID NO: 5 to 41.

The vaccine composition may comprise two or more immunogenic peptides, such as about one to about 50, 2 to 40, 3 to 30, 4 to 25, 5 to 20, 6 to 15, 7, 8, 9 or 10 immunogenic peptides. In this case, each of the two or more immunogenic peptides may, for example, be an immunogenic peptide that comprises a CD8+ T cell epitope from a polypeptide encoded by an ORF encoded by at least part of the genome of a ssRNA virus in the opposite sense to positive sense RNA capable of translation. Alternatively, the vaccine composition may contain a mixture of (i) immunogenic peptides that comprise a CD8+ T cell epitope from a polypeptide encoded by an ORF encoded by at least part of the genome of a ssRNA virus in the opposite sense to positive sense RNA capable of translation and (ii) other immunogenic peptides.

The vaccine composition may comprise two or more immunogenic peptides each comprising a different CD8+ T cell epitope from a polypeptide encoded by an ORF encoded by at least part of the genome of a ssRNA virus in the opposite sense to positive sense RNA capable of translation. In other words, the vaccine composition may comprise two or more immunogenic peptides that each comprise a different fragment of a polypeptide encoded by an ORF encoded by at least part of the genome of a ssRNA virus in the opposite sense positive sense RNA capable of translation. Preferably, the fragment is immunogenic. The vaccine composition may comprise about one to about 50, 2 to 40, 3 to 30, 4 to 25, 5 to 20, 6 to 15, 7, 8, 9 or 10 immunogenic peptides each comprising a different CD8+ T cell epitope from a polypeptide encoded by an ORF encoded by at least part of the genome of a ssRNA virus in the opposite sense to positive sense RNA capable of translation. In some aspects, each of the immunogenic peptides may interact with a different HLA subtype, as described in detail below.

The vaccine composition may comprise (i) one or more (such as about 2 to 40, 3 to 30, 4 to 25, 5 to 20, 6 to 15, 7, 8, 9 or 10) immunogenic peptides that each comprise a CD8+ T cell epitope from a polypeptide encoded by an ORF encoded by at least part of the genome of a ssRNA virus in the opposite sense to positive sense RNA capable of translation, and (ii) one or more other immunogenic peptides (i.e. immunogenic peptides that do not comprise a CD8+ T cell epitope from a polypeptide encoded by an ORF encoded by at least part of the genome of a ssRNA virus in the opposite sense to positive sense RNA capable of translation). The other immunogenic peptide(s) may therefore comprise one or more epitopes, such as about 2 to 40, 3 to 30, 4 to 25, 5 to 20, 6 to 15, 7, 8, 9 or 10 epitopes. The epitope may be B cell epitope, a CD4+ T cell epitope and/or CD8+ T cell epitope. The CD4+ T cell epitope may, for example, be a peptide that is expressed by one or more ssRNA viruses and that is that is capable of (i) presentation by a class II MHC molecule and (ii) recognition by a T cell receptor (TCR) present on a CD4+ T cell. Alternatively, the CD4+ T cell epitope may be an CD4+ T cell epitope that is not expressed by one or more ssRNA viruses. The CD8+ T cell epitope may, for example, be a peptide that is expressed by one or more ssRNA virus and that is that is capable of (i) presentation by a class I MHC molecule and (ii) recognition by a T cell receptor (TCR) present on a CD8+ T cell. Preferably, the CD8+ T cell epitope is a CD8+ T cell epitope that is not a CD8+ T cell epitope from a polypeptide encoded by an ORF encoded by at least part of the genome of a ssRNA virus in the opposite sense to positive sense RNA capable of translation. The CD8+ T cell epitope may be an CD8+ T cell epitope that is not expressed by one or more ssRNA viruses.

Many B cell epitopes, CD4+ T cell epitopes and CD8+ T cell epitopes (such as B cell epitopes, CD4+ T cell epitopes and CD8+ T cell epitopes from ssRNA viruses) are known in the art. Methods for identifying B cell epitopes, CD4+ T cell epitopes and CD8+ T cell epitopes are known in the art. Epitope mapping methods include X-ray co-crystallography, array-based oligo-peptide scanning (sometimes called overlapping peptide scan or pepscan analysis), site-directed mutagenesis, high throughput mutagenesis mapping, hydrogen-deuterium exchange, crosslinking coupled mass spectrometry, phage display and limited proteolysis. MHC motif prediction methodologies may also be used. CD8+ T cell epitopes presented by ssRNA virus-infected cells can be identified in order to directly identify CD8+ T cell epitopes for inclusion in the vaccine composition, as described below.

Any of the immunogenic peptides described herein may contain any number of amino acids, i.e. be of any length. Typically, the immunogenic peptide is about 8 to about 30, 35 or 40 amino acids in length, such as about 9 to about 29, about 10 to about 28, about 11 to about 27, about 12 to about 26, about 13 to about 25, about 13 to about 24, about 14 to about 23, about 15 to about 22, about 16 to about 21, about 17 to about 20, or about 18 to about 29 amino acids in length.

Any of the immunogenic peptides described herein may be chemically derived from a polypeptide antigen, for example by proteolytic cleavage. More typically, the immunogenic peptide may be synthesised using methods well known in the art.

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—NH2 may be modified to —NH(Me) or —$N(Me)_2$).

The term "peptide" also includes peptide variants that increase or decrease the half-life of the peptide in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

Open Reading Frame (ORF)

The CD8+ T cell epitope comprised in the immunogenic peptide is from a polypeptide encoded by an ORF encoded by at least part of the genome of a ssRNA virus in the opposite sense to positive sense RNA capable of translation.

A reading frame is a grouping of three successive nucleotides in a nucleic acid sequence, such as an RNA sequence, that constitutes the codons for the amino acids encoded by the nucleic acid sequence. An ORF is the part of a reading frame that can be translated. An ORF is a continuous stretch of codons that contain a start codon and a stop codon. Within the ORF, an initiation codon (e.g. ATG) may serve as an initiation site for translation of the RNA into protein.

In the present invention, the ORF is encoded by at least part of the genome of the ssRNA virus, in the opposite sense to positive sense RNA capable of translation. In a negative-sense ssRNA virus, the ORF is present in the genomic RNA (normally thought of as negative sense) and may, for example, be translated without intervening transcription. In a positive-sense ssRNA virus, the viral genomic RNA is the same sense as the mRNA and can be translated without intervening transcription i.e. the genomic RNA doubles as mRNA. Here, the ORF is encoded in the opposite sense to the viral genomic RNA and, therefore, the mRNA.

The ORF may, for example, be encoded by the whole of the genome of the ssRNA virus in the opposite sense to positive sense RNA capable of translation. Alternatively, the ORF may be encoded by only some of the genome of the ssRNA virus in the opposite sense to positive sense RNA capable of translation. For instance, the ORF may be encoded by about 1% to about 99%, such as about 2% to about 98%, about 3% to about 97%, about 5% to about 95%, about 10% to about 90%, about 15% to about 85%, about 20% to about 80%, about 25% to about 75%, about 30% to about 70%, about 40% to about 60%, or about 50% of the genome of the ssRNA virus in the opposite sense to positive sense RNA capable of translation.

Some ssRNA viruses have a segmented genome. The ORF may be encoded by all or part of a genome segment, in the opposite sense to positive sense RNA capable of translation. For instance, the ORF may be encoded by about 1% to about 99%, such as about 2% to about 98%, about 3% to about 97%, about 5% to about 95%, about 10% to about 90%, about 15% to about 85%, about 20% to about 80%, about 25% to about 75%, about 30% to about 70%, about 40% to about 60%, or about 50% of a genome segment, in the opposite sense to positive sense RNA capable of translation. The genome segment may, for example, be segment 1, segment 2, segment 3, segment 4, segment 5, segment 6, segment 7 or segment 8 of the genome of an Influenza A virus. Preferably, the genome segment is segment 8 of the genome of an Influenza A virus.

The ORF may be of any length. For example, the ORF may be about 8 to about 300, such as about 9 to about 290, about 10 to about 280, about 11 to about 275, about 12 to about 270, about 13 to about 260, about 14 to about 250, about 15 to about 240, about 16 to abut 230, about 17 to about 225, about 18 to about 220, about 19 to about 210, about 20 to about 200, about 25 to about 190, about 30 to about 180, about 35 to about 175, about 40 to about 170, about 45 to about 160, about 50 to about 150, about 55 to about 140, about 60 to about 130, about 65 to about 125, about 70 to about 120, about 75 to about 110, about 80 to about 100, about 85 to about 95, about 167 to about 216, or about 90 codons in length. The ORF may be at least 8, such as at least 9, at least 10, at least, 11, at least 12, at least 13, at least 14, at least 15, at least 20, at least 30, at least 40, at least 50, at least 60, at least 70, at least 80, at least 90, at least 100, at least 125, at least 150, at least 175, at least 200, at least 225, at least 250 or at least 275 codons in length. The ORF may, for example, be at least 31, at least 36, at least 37, at least 39, at least 40, at least 41, at least 45, at least 48, at least 49, at least 50, at least 53, at least 58, at least 60, at least 63, at least 73, at least 74, at least 80, at least 81, at least 84, at least 85, at least 87, at least 88, at least 89, 92, 93, at least 94, at least 105, 1 at least 21, at least 135, at least 140, at least 167, at least 170, at least 178, at least 197, at least 216 or at least 246 codons in length. The ORF may, for example, be at least 85 codons in length. The ORF may, for example, be at least 167 codons in length. The ORF may, for example, be at least 216 codons in length.

The ORF may comprise the sequence:

```
                                           (SEQ ID NO: 56)
TTAAATAAGCTGAAACGAGAAAGTTCTTATCTCTTGCTCCACTTCAAGC
AATAGTTGTAAGGCTTGCATAAATGTTATTTGCTCAAAACTATTCTCTG
TTATCTTCAGTCTATGTCTCACTTCTTCAATCAACCATCTTATTTCTTC
AAACTTCTGACTTAATTGTTCTCGCCATTTTCCGTTTCTGTTTTGGAGG
GAGTGGAGGTCTCCCATTCTCATTACTGCTTCTCCAAGCGAATCTCTGT
AGAGTTTCAGAGACTCGAACTGTGTTATCATTCCATTCAAGTCCTCCGA
TGAGGACCCCAACTGCATTTTTGACATCCTCATCAGTATGTCCTGGAAG
AGAAGGCAATGGTGAAATTTCGCCAACAATTGCTCCCTCTTCGGTGAAA
GCCCTTAGTAGTATTAGAGTCTCCAGCCGGTCGAAAATCACACTGAAGT
TCGCTTTCAGTATGATGTTCTTATCCATGATCGCCTGGTCCATTCTGAT
ACAAAGAGAGCCTGCCACTTTCTGCTTGGGCATGAGCATGAACCAGTCC
CTTGACATCTCCTCAAGAGTCATGTCAGTTAGGTAGCGCGAAGCAGGTA
CAGAGGCAATGGTCATTTTAAGTGCCTCATCGGATTCTTCCTTCAGAAT
CCGCTCCACTATCTGCTTTCCAGCACGGGTGGCTGTCTCGATGTCCAGA
CCAAGAGTGCTGCCTCTTCCTCTTAGGGACTTCTGATCTCGGCGAAGCC
GATCAAGGAATGGGGCATCACCCAGTTCTTGGTCTGCAAACCGTTTGCG
GACATGCCAAAGAAAGCAGTCTACCTGAAAGCTTGACACAGTGTTGGAA
TCCAT.
```

The ORF may encode a polypeptide comprising the sequence:

```
                                           (SEQ ID NO: 1)
MLFAQNYSLLSSVYVSLLQSTILFLQTSDLIVLAIFRFCFGGSGGLPFS
LLLLQANLCRVSETRTVLSFHSSPPMRTPTAFLTSSSVCPGREGNGEIS
PTIAPSSVKALSSIRVSSRSKITLKFAFSMMFLSMIAWSILIQREPATF
CLGMSMNQSLDISSRVMSVR.
```

The ORF may comprise the sequence:

```
                                           (SEQ ID NO: 57)
TATCATTAAATAAGCTGAAATGAGAAAGTTCTTATCTCCTGTTCCACTT
CAAACAGCAGTTGTAATGCTTGCATGAATGTTATTTGTTCAAAGCTATT
TTCCGTTGTTTTTAGTCTGTGTCTCACTTCTTCAATCAGCCATCTTATC
TCTTCAAACTTTTGACCTAGCTGTTCTCGCCATTTTCCGTTTCTGTTTT
GGAGTAAGTGGAGGTCCCCCATTCTCATTACTGCTTCTCCAAGCGAATC
TCTGTAGATTTTTAGAGACTCGAACTGTGTTATCATTCCATTCAAGTCC
TCCGATGAGGACCCCAATTGCATTTTTGACATCCTCAATAGTATGTCCT
GGAAAAGAAGGCAATGGTGAGATTTCGCCAACAATTGCTCCCTCTTCGG
TGAAAGCCCTTAGTAATACTATGGTCTCTAGTCGGTCAAAAATCACACT
GAAATTCGCTTTCAATATGATGTTTTTCTCCATGATTGCCTGGTCCATT
```

-continued

```
CTGATGCAAAGAGGTCCTTCCACTTTCTGCTTGGGCATTAGCATGAACC
AGTTTCTTGACAATTCCTCAATAGTCATGTCAGTTATGTATCGCGAAGC
AGGTGTGGAGACCATGGTCATTTTAAGTGCCTCATCAGATTCTTCTTTC
AGAATCTTTTCTACAATTTGCTTTCCAACATGGGTGGCTGCTTTGATGT
CTAGACCGAGAGTATTGCCTCTTCCCCTTAGGGACCTCTGATCTCGGCG
AAGCCGATCAAGGAATGGGGCATCACTCAGTTCTTGGTCTACAACTTGT
TTCCGGATATGCCAAAGAAAGCAATCTACCTGGAAACTTGACACAGTGT
TGGAATCCATTATGT.
```

The ORF may encode a polypeptide comprising the sequence:

```
                                           (SEQ ID NO: 2)
MLFVQSYFPLFLVCVSLLQSAILSLQTFDLAVLAIFRFCFGVSGGPPFS
LLLLQANLCRFLETRTVLSFHSSPPMRTPIAFLTSSIVCPGKEGNGEIS
PTIAPSSVKALSNTMVSSRSKITLKFAFNMMFFSMIAWSILMQRGPSTF
CLGISMNQFLDNSSIVMSVMYREAGVETMVILSASSDSSFRIFSTICFP
TWVAALMSRPRVLPLPLRDL.
```

The ORF may encode a polypeptide comprising the sequence:

```
                                           (SEQ ID NO: 3)
MLFARNYSLLSSIYVSLLQSTTLFLQTSDSIVLAIFRFCFGGSGGLLSS
LLLLQANLCRVSETRTVLSFHSSPPMRTPIAFLTSSSVCPGREGTGEIS
PTIAPSSVKALSSIRVSNRSKIILKFAFSVMFLSMIAWSILIQREPATF
CLGMSMNQSLDISSRVMSVR.
```

The ORF may encode a polypeptide comprising the sequence:

```
                                           (SEQ ID NO: 4)
MLFAQNYSLLSSVCVSLLQSTILFLQTSDLIVPAISRFCFGVSCGLPFS
LLLLQANLCRVSETRTVLSFHSSPPMRTPTAFLTSSAVCPGREGNGEIS
PTIAPSSVKALSNIRVSSRSKITLKFAFSMMFLSMIAWSILIQRGPATF
CLGMSMDQSLDISSRVMSVR.
```

The ORF may encode a polypeptide comprising the sequence:

```
                                           (SEQ ID NO: 5)
MLFAQNYSLLFSICVSLLQSTILFLRTSDLIVLAIFRFCFGVSGGLPVS
LLLLQANLCRVLETRTVLSFHSSPPMRTPIAFLTSSLVCPGREGNGEIS
PTIAPSSVKALSNIRVSSRSKITLKFAFSMMLLSMIAWSILIQRGPATF
CLGMSMNQSLDISSIVMSVR.
```

The ORF may encode a polypeptide comprising the sequence:

(SEQ ID NO: 6)
MLFAQNYSLLFSICASLLQSTILFLRTSDLIVLAIFRFCFGVSGGLPVS

LLLLQANLCRVLETRTVLSFHSSPPMRTPIAFLTSSLVCPGREGNGEIS

PYIAPSSVKALSNIRVSSRSKITLKFAFSMMLLSMIAWSILIQRGPATF

CLGMSMNQSLDISSIVMSVR.

The ORF may encode a polypeptide comprising the sequence:

(SEQ ID NO: 7)
MLFAQNYSLLSSICVSLLQSAILFLRTFDLIVLAIFRFCFGVSGGLPFS

LLLLQANLCRVLETRTVLSFHSSPPMRTPIAFLTSSLVCPGREGNGEIS

PTIAPSSVKALSNIRVSSRSKITLKFAFNMMFLSMIAWSILIQRGPATF

CLGISMNQSLDISSIVMSVRYREAGAEAMVILSASSDSSFRILSTICFP

TRVAVSMFRPRVLPLPLRDF.

The ORF may encode a polypeptide comprising the sequence:

(SEQ ID NO: 8)
MLFAQNYSLLSSICVSLLQSAILFLRTFDLIVLAIFRFYFGVSGGLPFS

SLLLQANLCRVLETRTVLSFHSSPPMRTPIAFLTSSLVCPGREGNGEIS

PTIAPASVKALSNIRVSSRSKITLKFAFNMMFLSMIAWSILIQRGPATF

CLGISMNQSLDISSIVMSBRYREAGAEAMVILSASSDSSFRILSTICFP

TRVAVSMFRPRVLPLPLRDF.

The ORF may encode a polypeptide comprising the sequence:

(SEQ ID NO: 9)
MLFAQNYSLLSSICVSLLQSAILSLRTFDLTVLAIFRFCFGVSGGLPFS

LLLPQANLCRVLETRTVLSFHSSPPMRTPIAFLTSSIVCPGREGNGEIS

PTIAPSSVKALSNIRVSSRSKITLKFAFNMTFLSMIAWSILMQRGPSTF

CLGISMNQSLDNSSIVMSVRYREAGAEAMVILSASSDSSFRILSTICFP

TRVAASMFRPRVLPLPLRDF.

The ORF may encode a polypeptide comprising the sequence:

(SEQ ID NO: 10)
MLFAQNYSLLSSICVSLLQSAILSLRTFDLIVLAIYRFCFGVSGCLPFS

LLLLQANLCRFLETRTVLSFHSSPPMRTPIAFLTSSIVCPGREGNGEIS

PTIAPSSVKALSNIRVSSRSKITLKFAFNMMFLSMIAWSILMQRGPSTF

CLGISMNQSLDNSSIVMSVRYREAGAEAMVILSASSDFSFRILSTICFP

TRVAASMFRPRVLPLPLRDF.

The ORF may encode a polypeptide comprising the sequence:

(SEQ ID NO: 11)
MLFAQNYSQLFSVCVSLLQSAILSLRTFDLAVLAIFRFCFGVSGGPPFS

LLLPQANLCRVLETRTVLSFHSSPPMRTPIAFLTSSIVCPGKEGNGEIS

PTIAPSSVKALSNTRVSSRSKITLKFAFNMMFFSMIAWSILMQRGPSTF

CLGISMNQFLDNSSIVMSVMYREAGVEAMVILSASSDSSFRIFSTICFP

TWVAALMSRPRVLPLPLRDL.

The ORF may encode a polypeptide comprising the sequence:

(SEQ ID NO: 12)
MLFAQNYSQLFLVCVSLLQSAILSLRTFDLAVLAIFRFCFGVSGGPPFS

LLLPQANLCRFLETRTVLSFHSSPPMRTPIAFLTSSIVCPGKEGNGEIS

PYIAPSSVKALSNTRVSSRSKITLKFAFNMMFFSMIAWSILMQRGPSTF

CLGISMNQFLDNSSIVISVMYREAGVEAMVILSASSDSSFRIFSTICFP

TWVAALMSRPRVLPLPLRDL.

The ORF may encode a polypeptide comprising the sequence:

(SEQ ID NO: 13)
MLFAQNYSQLFLVCVSLLQSAILSLQTFDLAVLAIFRFCFGVSGGPPFS

LLLLQANLCRFLETRTVLSFHSSPPMRTPIAFLTSSIVCPGKEGNGEIS

PTIAPSSVKALSNTMVSSRSKTTLKFAFNMMFFSMIAWSILMQRGPSTF

CLGISMNQFLDNSSIVMSVMYREAGVEAMVILSASSDSSFRIFSTICFP

TWVAALISRPRVLPLPLRDL.

The ORF may encode a polypeptide comprising the sequence:

(SEQ ID NO: 14)
MLFVQSYFQLFLICVSLLQLAILSLQTFDLAVLAISRFCFGVSGGPPFS

LLLLQANLCRFLETRTVLSFHSSPPMRTPIAFLTSSIVCPGKEGNGEIS

PTIAPSSVKALSNTIVSSRSKITLKFAFNVMFFSMIAWSILMQRGPSTF

CLGISMNQFLDNSSIVMSVMYREAGVETMVILSASSDSSFRIFSTICFP

TWVAALMSRPRVLPLPLRDL.

The ORF may encode a polypeptide comprising the sequence:

(SEQ ID NO: 15)
MLFVQSYFQLFLICVSPLQLAILSLQTSDLAVLAISRFCFGVSGGPPFS

LLLLQANLCRFLETRTVLSFHSSPPMRTPIAFLTASIVCPGKEGNGEIS

PTIAPSSVKALSNTMVSSRPKITLKFAFNMIFFSMIAWSILMQRGPSTF

CLGISMNQFLDSSSIVMSVMYREAGVETMVILSASSDSSFRIFSIICFP

AWVAALVSRPRVLPLPLRDL.

The ORF may encode a polypeptide comprising the sequence:

```
                                        (SEQ ID NO: 58)
MLFVRNYSLSLSICAAFLQLTTLFPQISVPIALATFHFCSGGSEGLPFS
SQFLQANLCIFSETRTVLPFHSSPPMRTPTAFLTSS.
```

As mentioned above, the ORF encoding the epitope comprised in the immunogenic peptide may be conserved between different ssRNA viruses, such as different ssRNA viruses of the same type. The ORF may be conserved between two or more different ssRNA viruses if there is at least 50% (such as at least 60%, at least 70%, at least 75%, at least 80%, at least 90%, at least 95%, at least 98% or at least 99%) identity between the ORF encoded by at least part of the genome of each virus in the opposite sense to positive sense RNA capable of translation. For example, the ORF may be conserved between two or more different ssRNA viruses if there is about 75% (such as about 70% to about 80%, e.g. about 71%, about 72%, about 73%, about 74%, about 76%, about 77%, about 78%, or about 79%) identity between the ORF encoded by at least part of the genome of each virus, in the opposite sense to positive sense RNA capable of translation. The polypeptide encoded by the ORF may enhance the fitness of the ssRNA virus in humans, i.e. confer a selective advantage on the ssRNA virus.

The ORF may be conserved between two or more (such as three or more, four or more, five or more, six or more, seven or more, eight or more, nine or more, 10 or more, 20 or more, 50 or more, 100 or more, 250 or more, 500 or more, 750 or more, or 1000 or more) influenza A viruses. The influenza A viruses between which the ORF is conserved may be of the same serotype. The influenza A viruses between which the ORF is conserved may be of different serotypes. For example, the ORF may be conserved between two or more viruses each belonging to one of the following serotypes: H1N1, H2N2, H3N2, H5N1, H7N7, H1N2, H9N2, H7N2, H7N3, H10N7, H7N9, H6N1, The ORF may be conserved between two or more (such as three or more, four or more, five or more, six or more, seven or more, eight or more, nine or more, 10 or more, 20 or more, 50 or more, 100 or more, 250 or more, 500 or more, 750 or more, or 1000 or more) human influenza A viruses. The ORF may be conserved between one or more (such as two or more, three or more, four or more, five or more, six or more, seven or more, eight or more, nine or more, 10 or more, 20 or more, 50 or more, 100 or more, 250 or more, 500 or more, 750 or more, or 1000 or more) human influenza A viruses and one or more (such as two or more, three or more, four or more, five or more, six or more, seven or more, eight or more, nine or more, 10 or more, 20 or more, 50 or more, 100 or more, 250 or more, 500 or more, 750 or more, or 1000 or more) swine Influenza A viruses. The ORF may be conserved between one or more (such as two or more, three or more, four or more, five or more, six or more, seven or more, eight or more, nine or more, 10 or more, 20 or more, 50 or more, 100 or more, 250 or more, 500 or more, 750 or more, or 1000 or more) human influenza A viruses and one or more (such as two or more, three or more, four or more, five or more, six or more, seven or more, eight or more, nine or more, 10 or more, 20 or more, 50 or more, 100 or more, 250 or more, 500 or more, 750 or more, or 1000 or more) avian Influenza A viruses. The ORF may be conserved between one or more (such as two or more, three or more, four or more, five or more, six or more, seven or more, eight or more, nine or more, 10 or more, 20 or more, 50 or more, 100 or more, 250 or more, 500 or more, 750 or more, or 1000 or more) human influenza A viruses and one or more (such as two or more, three or more, four or more, five or more, six or more, seven or more, eight or more, nine or more, 10 or more, 20 or more, 50 or more, 100 or more, 250 or more, 500 or more, 750 or more, or 1000 or more) equine Influenza A viruses.

The ORF may be conserved between two or more (such as three or more, four or more, five or more, six or more, seven or more, eight or more, nine or more, 10 or more, or 20 or more) flaviviruses. For example, the ORF may be conserved between two or more Dengue virus serotypes selected from DENV-1, DENV-2, DENV-3 and DENV-4. The ORF may be conserved between two or more strains of Zika virus, such as African Zika virus and Asian Zika virus. The ORF may be conserved between one or more Dengue virus serotypes (e.g. one or more of DENV-1, DENV-2, DENV-3 and DENV-4) and one or more strains of Zika virus (e.g. one or both of African Zika virus and Asian Zika virus).

The ORF may be conserved between two or more (such as three or more, four or more, five or more, six or more, seven or more, eight or more, nine or more, 10 or more, or 20 or more) filoviruses. For example, the ORF may be conserved between two or more ebolaviruses selected from Zaire ebolavirus (ZEBOV), Bundibugyo ebolavirus (BDBV), Reston ebolavirus (RESTV), Sudan ebolavirus (SUDV), and Tai Forest ebolavirus (TAFV). The ORF may be conserved between two or more Marburgviruses, such as Marburg virus (MARV) and Ravn virus (RAVV). The ORF may be conserved between one or more ebolaviruses (e.g. one or more of ZEBOV, BDBV, RESTV, SUDV and TAFV) and one or more marburgviruses (e.g. one or both of MARC and RAVV).

The polypeptide encoded by the ORF, and/or the epitope it includes, may similarly be conserved between two or more viruses. The vaccine composition may therefore be capable of providing cross-protection against multiple viruses. A single vaccine composition of the invention may therefore be able to induce protective immunity against a variety of existing and emerging ssRNA viruses, such as Influenza A viruses, flaviviruses or filoviruses. For example, in one aspect, the polypeptide and/or epitope may be conserved between two or more human influenza A viruses. In this case, the vaccine composition of the invention may be capable of providing protection against two or more human influenza A viruses. In another aspect, the polypeptide and/or epitope may be conserved between human influenza A viruses and a swine, equine and/or avian influenza A virus. In this case, the vaccine composition of the invention may be able to protect a human subject against infection with a swine, equine and/or avian influenza A virus, preventing swine, equine and/or avian influenza A viruses from crossing the species divide. In any case, the two or more human influenza A viruses may be of the same or different serotypes. Each of the two or more human influenza A viruses may be of serotype H1N1, H2N2, H3N2, H5N1, H7N7, H1N2, H9N2, H7N2, H7N3, H10N7, H7N9 or H6N1.

Viruses

The ssRNA virus whose genome encodes, in the opposite sense to positive sense RNA capable of translation RNA, an ORF encoding a polypeptide may be a negative-sense ssRNA virus or a positive sense-ssRNA virus.

The ssRNA virus may be any negative-sense ssRNA virus. Negative-sense ssRNA viruses are well known in the art and include viruses from the orders Mononegavirales and Bunyvirales. The order Mononegavirales includes the Bornaviridae, Filoviridae, Mymonaviridae, Nyamiviridae, Paramyxoviridae, Pneumoviridae, Rhabdoviridae and Sunviridae families, as well as the Anphevirus, Arlivirus, Chengtivirs, Crustavirus and Wastrivirus genera. The order Bunyavirales includes the Feraviridae, Fimoviridae, Hantavirida, Jonviridae, Nairoviridae, Peribunyaviridae, Phasmaviridae, Phenuiviridae and Tospoviridae families. Other negative-sense ssRNA viruses include those of the Arenaviridae, Ophiovirida and Orthomyxoviridae families, as well as the Deltavirus genus.

The ssRNA virus may be an Orthomyxovirus. For example, the ssRNA virus may be an influenza virus. Hundreds of strains of influenza virus exist which may be classified in three main categories, Influenza A, Influenza B or Influenza C, based on the HA and NA proteins they express. The ssRNA virus may be an Influenza A, Influenza B or Influenza C virus of any strain. Thus, the ORF encoding the polypeptide comprising the CD8+ T cell epitope may be encoded by at least part of the genome of an Influenza A, Influenza B and/or Influenza C virus in the opposite sense to positive sense RNA capable of translation. Preferably, the ssRNA virus is an Influenza A virus. The Influenza A virus may be of any serotype. Preferably, the Influenza A virus is of serotype H1N1, H2N2, H3N2, H5N1, H7N7, H1N2, H9N2, H7N2, H7N3, H10N7, H7N9 or H6N1. Influenza viruses and the ORFs they may encode are considered in more detail below.

The ssRNA virus may be a Filovirus. Numerous species of filovirus exist across two main genera, ebolaviruses and marburgviruses. Ebolavirus species include Zaire ebolavirus (ZEBOV), Bundibugyo ebolavirus (BDBV), Reston ebolavirus (RESTV), Sudan ebolavirus (SUDV), and Tai Forest ebolavirus (TAFV). Marburgvirus species include Marburg virus (MARV) and Ravn virus (RAVV). A third genus, cuevaviruses, includes the Lloviu virus species. Preferably, the ssRNA virus is an Ebola virus or Marburg virus.

The ssRNA virus may be any positive-sense ssRNA virus. Positive-sense ssRNA viruses are well known in the art and include the Picornaviridae, Astroviridae, Caliciviridae, Hepeviridae, Flaviviridae, Togaviridae, Arteriviridae and Coronaviridae families.

The ssRNA virus may be a Flavivirus. Numerous species of flavivirus exist, including Zika virus, Dengue virus, West Nile virus and yellow fever virus, as well as St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest virus, Omsk Hemorrhagic Fever virus, Powassan virus, Louping Ill virus, Rio Bravo virus, Tyuleniy virus, Ntaya virus and Modoc virus. There are four serotypes of Dengue virus (DENV-1, DENV-2, DENV-3 and DENV-4) and two strains of Zika virus (African Zika virus and Asian Zika virus). Preferably, the ssRNA virus is a Dengue virus or a Zika virus.

Influenza Virus

As set out above, the ssRNA virus may be a negative-sense ssRNA virus. For example, the ssRNA virus may be an Orthomyxovirus, such as an influenza virus. The influenza virus may, for instance, be an influenza A virus, and influenza B virus or an influenza C virus. Preferably, the ssRNA virus is an influenza A virus. The influenza A virus may, for example, be a human influenza A virus, a swine influenza A virus, an equine influenza A virus, or an avian influenza A virus. The influenza A virus may be a zoonotic influenza A virus.

The influenza virus may, for example, be a Spanish flu virus, such as the H1N1 influenza A virus that was responsible for the 1918 flu pandemic (the "1918 influenza virus"). The complete coding sequence of the 1918 influenza virus is known in the art. The influenza virus may, for example, be a reconstructed Spanish flu virus. A reconstructed Spanish flu virus is an influenza virus that bears the coding sequences of the eight gene segments of the 1918 influenza virus. For instance, a reconstructed Spanish flu virus comprises the known coding sequence of the 1918 influenza virus and non-coding regions corresponding to those from a closely related virus. The closely related virus may, for example, be a H1N1 influenza a virus, such as A/WSN/33 (H1N1) virus.

The genome of influenza A viruses is segmented, comprising 8 segments of negative-sense ssRNA. While many structural and genetic similarities exist between human, swine, equine and avian influenza A viruses, cross-species infection tends to be infrequent and inefficient. However, co-infection of a single host with multiple different influenza A viruses can lead to re-assortment of the segmented genome, giving rise to new strains that may have pandemic potential.

When translated in the normal way (i.e. following transcription to complementary mRNA), segment 8 of the influenza A virus genome encodes two proteins, NS1 and NEP. In human influenza A viruses, segment 8 also encodes an ORF in the opposite sense to positive sense RNA capable of translation. The ORF is known as NEG8, as it is encoded by the so-called negative strand of segment 8. Almost all human influenza A viruses isolated in the first half of the $20^{th}$ century possessed a NEG8 ORF of 167 codons in length. Conservation of the 167 codon NEG8 ORF in human influenza A viruses over a period of around 50 years indicates that the 167 codon NEG8 ORF confers a selective advantage to human influenza A viruses. This is emphasised by the fact that viruses that lost the 167 codon NEG8 ORF did not persist in the human population for more than a few years. About halfway through the $20^{th}$ century, a mutation of the TAG stop codon of the 167 codon NEG8 ORF to TAT (encoding tyrosine) occurred, giving rise to an extended, 216 codon NEG8 ORF. The mutation had no effect on the other proteins encoded by segment 8, due to degeneracy in the amino acid code. Essentially all human influenza A viruses isolated after 1947 possess the 216 codon NEG8 ORF, indicating that this ORF also confers a selective advantage to human influenza A viruses. Recently, an 85 codon NEG8 ORF has also been observed in some human influenza A viruses. The 167 codon and 216 codon ORFs have also each been observed in a number of swine and avian influenza A viruses. ORFs of other lengths have also been observed in human, avian, equine and swine influenza A viruses (see Example 5). For example, a 93 codon ORF (or more rarely, a 135 codon ORF) has been observed in avian, avian-like swine, and equine influenza A viruses. A 140 codon ORF and a 167 codon ORF have been observed in swine influenza A viruses.

The presence of a conserved 85, 167 codon or 216 codon NEG8 ORF conferring a selective advantage on (i.e. enhancing the fitness of) human influenza A viruses has important implications for the emergence of new influenza A virus strains. In particular, co-infection of a host with two or more influenza A viruses can cause re-assortment of the viral genome. In essence, segments can switch between the viruses, giving rise to viruses having new combinations of genome segments. For instance, co-infection with virus X and virus Y could lead to the generation of a new virus having, for example, segments 1 to 7 from virus X and segment 8 from virus Y. This is worrying because segment 8 from a human influenza A virus possessing the 216 codon NEG8 ORF could re-assort with segments from an avian influenza A virus (e.g. H5N1), an equine influenza A virus, or a swine influenza A virus (e.g. H1N1). Normally, the avian influenza A virus does not possess the NEG8 ORF, and has limited pathogenicity and/or poor transmission in humans. Acquisition of the NEG8 ORF via re-assortment with a human influenza A virus may enhance the fitness of the avian, equine or swine influenza A virus in humans, potentially leading to the development of a new pandemic strain.

Furthermore, analysis of segment 8 from swine, equine or avian influenza A viruses has shown that, for certain strains, only minor mutations are needed to give rise to the 167 codon or 216 codon NEG8 ORF conferring viral fitness in humans. For example, only 2 stop codons need be removed (each by a single nucleotide change) from swine-derived H1N1 genome segment 8 to give rise to the 216 codon NEG8 ORF found in human influenza A viruses. Only 1 nucleotide change is needed to arrive at the 167 codon NEG8 ORF historically found in human influenza A viruses.

It is clear, therefore, that an effective vaccine composition against influenza A virus infection is needed. In one aspect, the vaccine composition of the invention is a vaccine composition against influenza A virus infection. Preferably, the immunogenic peptide comprised in the vaccine composition comprises a CD8+ T cell epitope from a polypeptide encoded by an ORF that is encoded by at least part of segment 8 of the influenza A virus genome, in the opposite sense to positive sense RNA capable of translation. Accordingly, the ORF may be a NEG8 ORF. The ORF may be encoded by all or part of segment 8, in the opposite sense to positive sense RNA capable of translation. For instance, the ORF may be encoded by about 1% to about 99%, such as about 2% to about 98%, about 3% to about 97%, about 5% to about 95%, about 10% to about 90%, about 15% to about 85%, about 20% to about 80%, about 25% to about 75%, about 30% to about 70%, about 40% to about 60%, or about 50% of segment 8, in the opposite sense to positive sense RNA capable of translation.

The ORF may be of any length, as described above. For example, the ORF may be about 8 to about 300, such as about 9 to about 290, about 10 to about 280, about 11 to about 275, about 12 to about 270, about 13 to about 260, about 14 to about 250, about 15 to about 240, about 16 to abut 230, about 17 to about 225, about 18 to about 220, about 19 to about 210, about 20 to about 200, about 25 to about 190, about 30 to about 180, about 35 to about 175, about 40 to about 170, about 45 to about 160, about 50 to about 150, about 55 to about 140, about 60 to about 130, about 65 to about 125, about 70 to about 120, about 75 to about 110, about 80 to about 100, about 85 to about 95, about 167 to about 216, or about 90 codons in length. The ORF may be at least 8, such as at least 9, at least 10, at least, 11, at least 12, at least 13, at least 14, at least 15, at least 20, at least 30, at least 40, at least 50, at least 60, at least 70, at least 80, at least 90, at least 100, at least 125, at least 150, at least 175, at least 200, at least 225, at least 250 or at least 275 codons in length. The ORF may, for example, be at least 31, at least 36, at least 37, at least 39, at least 40, at least 41, at least 45, at least 48, at least 49, at least 50, at least 53, at least 58, at least 60, at least 63, at least 73, at least 74, at least 80, at least 81, at least 84, at least 85, at least 87, at least 88, at least 89, 92, 93, at least 94, at least 105, 1 at least 21, at least 135, at least 140, at least 167, at least 170, at least 178, at least 197, at least 216 or at least 246 codons in length. The ORF may, for example, be at least 85 codons in length. Preferably, the ORF is at least 167 codons in length. Preferably, the ORF is at least 216 codons in length.

In some aspects, the ORF may comprise the sequence:

```
                                          (SEQ ID NO: 56)
TTAAATAAGCTGAAACGAGAAAGTTCTTATCTCTTGCTCCACTTCAAGC
AATAGTTGTAAGGCTTGCATAAATGTTATTTGCTCAAAACTATTCTCTG
TTATCTTCAGTCTATGTCTCACTTCTTCAATCAACCATCTTATTTCTTC
AAACTTCTGACTTAATTGTTCTCGCCATTTTCCGTTTCTGTTTTGGAGG
GAGTGGAGGTCTCCCATTCTCATTACTGCTTCTCCAAGCGAATCTCTGT
AGAGTTTCAGAGACTCGAACTGTGTTATCATTCCATTCAAGTCCTCCGA
TGAGGACCCCAACTGCATTTTTGACATCCTCATCAGTATGTCCTGGAAG
AGAAGGCAATGGTGAAATTTCGCCAACAATTGCTCCCTCTTCGGTGAAA
GCCCTTAGTAGTATTAGAGTCTCCAGCCGGTCGAAAATCACACTGAAGT
TCGCTTTCAGTATGATGTTCTTATCCATGATCGCCTGGTCCATTCTGAT
ACAAAGAGAGCCTGCCACTTTCTGCTTGGGCATGAGCATGAACCAGTCC
CTTGACATCTCCTCAAGAGTCATGTCAGTTAGGTAGCGCGAAGCAGGTA
CAGAGGCAATGGTCATTTTAAGTGCCTCATCGGATTCTTCCTTCAGAAT
CCGCTCCACTATCTGCTTTCCAGCACGGGTGGCTGTCTCGATGTCCAGA
CCAAGAGTGCTGCCTCTTCCTCTTAGGGACTTCTGATCTCGGCGAAGCC
GATCAAGGAATGGGGCATCACCCAGTTCTTGGTCTGCAAACCGTTTGCG
GACATGCCAAAGAAAGCAGTCTACCTGAAAGCTTGACACAGTGTTGGAA
TCCAT or a variant of SEQ ID NO: 56.
```

In some aspects, the ORF may comprise the sequence:

```
                                          (SEQ ID NO: 57)
TATCATTAAATAAGCTGAAATGAGAAAGTTCTTATCTCCTGTTCCACTT
CAAACAGCAGTTGTAATGCTTGCATGAATGTTATTTGTTCAAAGCTATT
TTCCGTTGTTTTTAGTCTGTGTCTCACTTCTTCAATCAGCCATCTTATC
TCTTCAAACTTTTGACCTAGCTGTTCTCGCCATTTTCCGTTTCTGTTTT
GGAGTAAGTGGAGGTCCCCCATTCTCATTACTGCTTCTCCAAGCGAATC
TCTGTAGATTTTTAGAGACTCGAACTGTGTTATCATTCCATTCAAGTCC
TCCGATGAGGACCCCAATTGCATTTTTGACATCCTCAATAGTATGTCCT
GGAAAAGAAGGCAATGGTGAGATTTCGCCAACAATTGCTCCCTCTTCGG
TGAAAGCCCTTAGTAATACTATGGTCTCTAGTCGGTCAAAAATCACACT
GAAATTCGCTTTCAATATGATGTTTTTCTCCATGATTGCCTGGTCCATT
CTGATGCAAAGAGGTCCTTCCACTTTCTGCTTGGGCATTAGCATGAACC
AGTTTCTTGACAATTCCTCAATAGTCATGTCAGTTATGTATCGCGAAGC
AGGTGTGGAGACCATGGTCATTTTAAGTGCCTCATCAGATTCTTCTTTC
AGAATCTTTTCTACAATTTGCTTTCCAACATGGGTGGCTGCTTTGATGT
CTAGACCGAGAGTATTGCCTCTTCCCCTTAGGGACCTCTGATCTCGGCG
AAGCCGATCAAGGAATGGGGCATCACTCAGTTCTTGGTCTACAACTTGT
TTCCGGATATGCCAAAGAAAGCAATCTACCTGGAAACTTGACACAGTGT
TGGAATCCATTATGT or a variant of SEQ ID NO: 57.
```

Over the entire length of the nucleotide sequence of SEQ ID NO: 56 or SEQ ID NO: 57, a variant will preferably be at least 50% identical to that sequence based on nucleotide identity. More preferably, the variant may be at least 55%, at least 60%, at least 65%, at least 70%, at least 75%, at least 80%, at least 85%, at least 90% and more preferably at least 95%, 97% or 99% identical based on nucleotide identity to the nucleotide sequence of SEQ ID NO: 56 or SEQ ID NO: 57 over the entire sequence. There may be at least 80%, for example at least 85%, 90% or 95%, nucleotide identity over a stretch of 100 or more, for example 125, 150, 175 or 200 or more, contiguous nucleotides.

As described above, the ORF may be conserved between two or more human influenza A viruses. The ORF may be conserved between one or more human influenza A viruses and one or more avian influenza A viruses. The ORF may be conserved between one or more human influenza A viruses and one or more equine influenza A viruses. The ORF may be conserved between one or more human influenza A viruses and one or more swine influenza A viruses. To be conserved between two or more influenza A viruses, the ORF in each of the two or more influenza A viruses preferably has at least 50% (such as at least 60%, at least 70%, at least 75%, at least 80%, at least 90%, at least 95%, at least 98% or at least 99%) identity over its entire sequence with the ORF in each of the other influenza A viruses. For example, the ORF may be conserved between two or more influenza A viruses if there is about 75% (such as about 70% to about 80%, e.g. about 71%, about 72%, about 73%, about 74%, about 76%, about 77%, about 78%, or about 79%) identity between the ORFs in each virus.

The ORF may encode a polypeptide comprising the sequence (SEQ ID NO: 1)

MLFAQNYSLLSSVYVSLLQSTILFLQTSDLIVLAIFRFCFGGSGGLPFS

LLLLQANLCRVSETRTVLSFHSSPPMRTPTAFLTSSSVCPGREGNGEIS

PTIAPSSVKALSSIRVSSRSKITLKFAFSMMFLSMIAWSILIQREPATF

CLGMSMNQSLDISSRVMSVR or a variant thereof. SEQ ID NO: 1 is the 167 amino acid sequence encoded by the nucleotide sequence of SEQ ID NO: 56.

The ORF may encode a polypeptide comprising the sequence (SEQ ID NO: 2)

MLFVQSYFPLFLVCVSLLQSAILSLQTFDLAVLAIFRFCFGVSGGPPFS

LLLLQANLCRFLETRTVLSFHSSPPMRTPIAFLTSSIVCPGKEGNGEIS

PTIAPSSVKALSNTMVSSRSKITLKFAFNMMFFSMIAWSILMQRGPSTF

CLGISMNQFLDNSSIVMSVMYREAGVETMVILSASSDSSFRIFSTICFP

TWVAALMSRPRVLPLPLRDL or a variant thereof. SEQ ID NO: 2 is the 216 amino acid sequence encoded by the nucleotide sequence of SEQ ID NO: 57.

The ORF may encode a polypeptide comprising the sequence (SEQ ID NO: 3)

MLFARNYSLLSSIYVSLLQSTTLFLQTSDSIVLAIFRFCFGGSGGLLSS

LLLLQANLCRVSETRTVLSFHSSPPMRTPIAFLTSSSVCPGREGTGEIS

-continued

PTIAPSSVKALSSIRVSNRSKIILKFAFSVMFLSMIAWSILIQREPATF

CLGMSMNQSLDISSRVMSVR or a variant thereof.

The ORF may encode a polypeptide comprising the sequence (SEQ ID NO: 4)

MLFAQNYSLLSSVCVSLLQSTILFLQTSDLIVPAISRFCFGVSCGLPFS

LLLLQANLCRVSETRTVLSFHSSPPMRTPTAFLTSSAVCPGREGNGEIS

PTIAPSSVKALSNIRVSSRSKITLKFAFSMMFLSMIAWSILIQRGPATF

CLGMSMDQSLDISSRVMSVR or a variant thereof.

The ORF may encode a polypeptide comprising the sequence (SEQ ID NO: 5)

MLFAQNYSLLFSICVSLLQSTILFLRTSDLIVLAIFRFCFGVSGGLPVS

LLLLQANLCRVLETRTVLSFHSSPPMRTPIAFLTSSLVCPGREGNGEIS

PTIAPSSVKALSNIRVSSRSKITLKFAFSMMLLSMIAWSILIQRGPATF

CLGMSMNQSLDISSIVMSVR or a variant thereof.

The ORF may encode a polypeptide comprising the sequence (SEQ ID NO: 6)

MLFAQNYSLLFSICASLLQSTILFLRTSDLIVLAIFRFCFGVSGGLPVS

LLLLQANLCRVLETRTVLSFHSSPPMRTPIAFLTSSLVCPGREGNGEIS

PYIAPSSVKALSNIRVSSRSKITLKFAFSMMLLSMIAWSILIQRGPATF

CLGMSMNQSLDISSIVMSVR or a variant thereof.

The ORF may encode a polypeptide comprising the sequence (SEQ ID NO: 7)

MLFAQNYSLLSSICVSLLQSAILFLRTFDLIVLAIFRFCFGVSGGLPFS

LLLLQANLCRVLETRTVLSFHSSPPMRTPIAFLTSSLVCPGREGNGEIS

PTIAPSSVKALSNIRVSSRSKITLKFAFNMMFLSMIAWSILIQRGPATF

CLGISMNQSLDISSIVMSVRYREAGAEAMVILSASSDSSFRILSTICFP

TRVAVSMFRPRVLPLPLRDF or a variant thereof.

The ORF may encode a polypeptide comprising the sequence (SEQ ID NO: 8)

MLFAQNYSLLSSICVSLLQSAILFLRTFDLIVLAIFRFYFGVSGGLPFS

SLLLQANLCRVLETRTVLSFHSSPPMRTPIAFLTSSLVCPGREGNGEIS

-continued

PTIAPASVKALSNIRVSSRSKITLKFAFNMMFLSMIAWSILIQRGPATF

CLGISMNQSLDISSIVMSBRYREAGAEAMVILSASSDSSFRILSTICFP

TRVAVSMFRPRVLPLPLRDF or a variant thereof.

The ORF may encode a polypeptide comprising the sequence (SEQ ID NO: 9)
MLFAQNYSLLSSICVSLLQSAILSLRTFDLTVLAIFRFCFGVSGGLPFS

LLLPQANLCRVLETRTVLSFHSSPPMRTPIAFLTSSIVCPGREGNGEIS

PTIAPSSVKALSNIRVSSRSKITLKFAFNMTFLSMIAWSILMQRGPSTF

CLGISMNQSLDNSSIVMSVRYREAGAEAMVILSASSDSSFRILSTICFP

TRVAASMFRPRVLPLPLRDF or a variant thereof.

The ORF may encode a polypeptide comprising the sequence (SEQ ID NO: 10)
MLFAQNYSLLSSICVSLLQSAILSLRTFDLIVLAIYRFCFGVSGCLPFS

LLLLQANLCRFLETRTVLSFHSSPPMRTPIAFLTSSIVCPGREGNGEIS

PTIAPSSVKALSNIRVSSRSKITLKFAFNMMFLSMIAWSILMQRGPSTF

CLGISMNQSLDNSSIVMSVRYREAGAEAMVILSASSDFSFRILSTICFP

TRVAASMFRPRVLPLPLRDF or a variant thereof.

The ORF may encode a polypeptide comprising the sequence (SEQ ID NO: 11)
MLFAQNYSQLFSVCVSLLQSAILSLRTFDLAVLAIFRFCFGVSGGPPFS

LLLPQANLCRVLETRTVLSFHSSPPMRTPIAFLTSSIVCPGKEGNGEIS

PTIAPSSVKALSNTRVSSRSKITLKFAFNMMFFSMIAWSILMQRGPSTF

CLGISMNQFLDNSSIVMSVMYREAGVEAMVILSASSDSSFRIFSTICFP

TWVAALMSRPRVLPLPLRDL or a variant thereof.

The ORF may encode a polypeptide comprising the sequence (SEQ ID NO: 12)
MLFAQNYSQLFLVCVSLLQSAILSLRTFDLAVLAIFRFCFGVSGGPPFS

LLLPQANLCRFLETRTVLSFHSSPPMRTPIAFLTSSIVCPGKEGNGEIS

PYIAPSSVKALSNTRVSSRSKITLKFAFNMMFFSMIAWSILMQRGPSTF

CLGISMNQFLDNSSIVISVMYREAGVEAMVILSASSDSSFRIFSTICFP

TWVAALMSRPRVLPLPLRDL or a variant thereof.

The ORF may encode a polypeptide comprising the sequence (SEQ ID NO: 13)
MLFAQNYSQLFLVCVSLLQSAILSLQTFDLAVLAIFRFCFGVSGGPPFS

LLLLQANLCRFLETRTVLSFHSSPPMRTPIAFLTSSIVCPGKEGNGEIS

PTIAPSSVKALSNTMVSSRSKTTLKFAFNMMFFSMIAWSILMQRGPSTF

CLGISMNQFLDNSSIVMSVMYREAGVEAMVILSASSDSSFRIFSTICFP

TWVAALISRPRVLPLPLRDL or a variant thereof.

The ORF may encode a polypeptide comprising the sequence (SEQ ID NO: 14)
MLFVQSYFQLFLICVSLLQLAILSLQTFDLAVLAISRFCFGVSGGPPFS

LLLLQANLCRFLETRTVLSFHSSPPMRTPIAFLTSSIVCPGKEGNGEIS

PTIAPSSVKALSNTIVSSRSKITLKFAFNVMFFSMIAWSILMQRGPSTF

CLGISMNQFLDNSSIVMSVMYREAGVETMVILSASSDSSFRIFSTICFP

TWVAALMSRPRVLPLPLRDL or a variant thereof.

The ORF may encode a polypeptide comprising the sequence (SEQ ID NO: 15)
MLFVQSYFQLFLICVSPLQLAILSLQTSDLAVLAISRFCFGVSGGPPFS

LLLLQANLCRFLETRTVLSFHSSPPMRTPIAFLTASIVCPGKEGNGEIS

PTIAPSSVKALSNTMVSSRPKITLKFAFNMIFFSMIAWSILMQRGPSTF

CLGISMNQFLDSSSIVMSVMYREAGVETMVILSASSDSSFRIFSIICFP

AWVAALVSRPRVLPLPLRDL or a variant thereof.

Over the entire length of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 or SEQ ID NO: 15, a variant will preferably be at least 50% identical to that sequence based on amino acid identity. More preferably, the variant may be at least 55%, at least 60%, at least 65%, at least 70%, at least 75%, at least 80%, at least 85%, at least 90% and more preferably at least 95%, 97% or 99% identical based on amino acid identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 or SEQ ID NO: 15 over the entire sequence. There may be at least 80%, for example at least 85%, 90% or 95%, amino acid identity over a stretch of 100 or more, for example 125, 150, 175 or 200 or more, contiguous amino acids.

The polypeptide encoded by the ORF may be conserved between two or more human influenza A viruses. The polypeptide may be conserved between one or more human influenza A viruses and one or more avian influenza A viruses. The polypeptide may be conserved between one or more human influenza A viruses and one or more equine influenza A viruses. The polypeptide may be conserved between one or more human influenza A viruses and one or more swine influenza A viruses. To be conserved between two or more influenza A viruses, the polypeptide encoded by the ORF in each of the two or more influenza A viruses preferably has at least 50% (such as at least 60%, at least 70%, at least 75%, at least 80%, at least 90%, at least 95%, at least 98% or at least 99%) identity over its entire sequence with the polypeptide encoded by the ORF in each of the other influenza A viruses. For example, the polypeptide may be conserved between two or more influenza A viruses if there is about 75% (such as about 70% to about 80%, e.g. about 71%, about 72%, about 73%, about 74%, about 76%, about 77%, about 78%, or about 79%) identity between the polypeptides encoded by the ORF in each virus.

The CD8+ T cell epitope from the polypeptide may be conserved between two or more human influenza A viruses. The epitope may be conserved between one or more human influenza A viruses and one or more avian influenza A viruses. The epitope may be conserved between one or more human influenza A viruses and one or more equine influenza A viruses. The epitope may be conserved between one or more human influenza A viruses and one or more swine influenza A viruses. To be conserved between two or more influenza A viruses, an epitope encoded by the ORF in each of the two or more influenza A viruses preferably has at least 50% (such as at least 60%, at least 70%, at least 75%, at least 80%, at least 90%, at least 95%, at least 98% or at least 99%) identity over its entire sequence with an epitope encoded by the ORF in each of the other influenza A viruses. For example, the epitope may be conserved between two or more influenza A viruses if there is about 75% (such as about 70% to about 80%, e.g. about 71%, about 72%, about 73%, about 74%, about 76%, about 77%, about 78%, or about 79%) identity between epitopes encoded by the ORF in each virus.

The ORF, polypeptide and/or epitope may be conserved among human H1N1 influenza A viruses. The ORF, polypeptide and/or epitope may be conserved among human H5N1 influenza A viruses. The ORF, polypeptide and/or epitope may be conserved among human H3N2 influenza A viruses. The ORF, polypeptide and/or epitope may be conserved among human H2N2 influenza A viruses. The ORF, polypeptide and/or epitope may be conserved among human H7N7 influenza A viruses. The ORF, polypeptide and/or epitope may be conserved among human H7N9 influenza A viruses. The ORF, polypeptide and/or epitope may be conserved among avian H1N1 influenza A viruses. The ORF, polypeptide and/or epitope may be conserved among avian H5N1 influenza A viruses. The ORF, polypeptide and/or epitope may be conserved among avian H3N2 influenza A viruses. The ORF, polypeptide and/or epitope may be conserved among avian H2N2 influenza A viruses. The ORF, polypeptide and/or epitope may be conserved among avian H7N7 influenza A viruses. The ORF, polypeptide and/or epitope may be conserved among avian H7N9 influenza A viruses. The ORF, polypeptide and/or epitope may be conserved among swine H1N1 influenza A viruses. The ORF, polypeptide and/or epitope may be conserved among swine H5N1 influenza A viruses. The ORF, polypeptide and/or epitope may be conserved among swine H3N2 influenza A viruses. The ORF, polypeptide and/or epitope may be conserved among swine H2N2 influenza A viruses. The ORF, polypeptide and/or epitope may be conserved among swine H7N7 influenza A viruses. The ORF, polypeptide and/or epitope may be conserved among swine H7N9 influenza A viruses. The ORF, polypeptide and/or epitope may be conserved among equine H1N1 influenza A viruses. The ORF, polypeptide and/or epitope may be conserved among equine H5N1 influenza A viruses. The ORF, polypeptide and/or epitope may be conserved among equine H3N2 influenza A viruses. The ORF, polypeptide and/or epitope may be conserved among equine H2N2 influenza A viruses. The ORF, polypeptide and/or epitope may be conserved among equine H7N7 influenza A viruses. The ORF, polypeptide and/or epitope may be conserved among equine H7N9 influenza A viruses.

The ORF may be conserved between (i) human H1N1 influenza A viruses, (ii) human H5N1 influenza A viruses, (iii) human H3N2 influenza A viruses, (iv) human H2N2 influenza A viruses, (v) human H7N7 influenza A viruses, (vi) human H7N9 influenza A viruses, (vii) avian H1N1 influenza A viruses, (viii) avian H5N1 influenza A viruses, (ix) avian H3N2 influenza A viruses, (x) avian H2N2 influenza A viruses, (xi) avian H7N7 influenza A viruses, (xii) avian H7N9 influenza A viruses, (xiii) swine H1N1 influenza A viruses, (xiv) swine H5N1 influenza A viruses, (xv) swine H3N2 influenza A viruses, (xvi) swine H2N2 influenza A viruses, (xvii) swine H7N7 influenza A viruses, (xviii) swine H7N9 influenza A viruses, (xix) equine H1N1 influenza A viruses, (xx) equine H5N1 influenza A viruses, (xxi) equine H3N2 influenza A viruses, (xxii) equine H2N2 influenza A viruses, (xxiii) equine H7N7 influenza A viruses and/or (xxiv) equine H7N9 influenza A viruses, alone or in any combination.

The polypeptide may be conserved between (i) human H1N1 influenza A viruses, (ii) human H5N1 influenza A viruses, (iii) human H3N2 influenza A viruses, (iv) human H2N2 influenza A viruses, (v) human H7N7 influenza A viruses, (vi) human H7N9 influenza A viruses, (vii) avian H1N1 influenza A viruses, (viii) avian H5N1 influenza A viruses, (ix) avian H3N2 influenza A viruses, (x) avian H2N2 influenza A viruses, (xi) avian H7N7 influenza A viruses, (xii) avian H7N9 influenza A viruses, (xiii) swine H1N1 influenza A viruses, (xiv) swine H5N1 influenza A viruses, (xv) swine H3N2 influenza A viruses, (xvi) swine H2N2 influenza A viruses, (xvii) swine H7N7 influenza A viruses, (xviii) swine H7N9 influenza A viruses, (xix) equine H1N1 influenza A viruses, (xx) equine H5N1 influenza A viruses, (xxi) equine H3N2 influenza A viruses, (xxii) equine H2N2 influenza A viruses, (xxiii) equine H7N7 influenza A viruses and/or (xxiv) equine H7N9 influenza A viruses, alone or in any combination.

The epitope may be conserved between (i) human H1N1 influenza A viruses, (ii) human H5N1 influenza A viruses, (iii) human H3N2 influenza A viruses, (iv) human H2N2 influenza A viruses, (v) human H7N7 influenza A viruses, (vi) human H7N9 influenza A viruses, (vii) avian H1N1 influenza A viruses, (viii) avian H5N1 influenza A viruses, (ix) avian H3N2 influenza A viruses, (x) avian H2N2 influenza A viruses, (xi) avian H7N7 influenza A viruses, (xii) avian H7N9 influenza A viruses, (xiii) swine H1N1 influenza A viruses, (xiv) swine H5N1 influenza A viruses, (xv) swine H3N2 influenza A viruses, (xvi) swine H2N2 influenza A viruses, (xvii) swine H7N7 influenza A viruses, (xviii) swine H7N9 influenza A viruses, (xix) equine H1N1 influenza A viruses, (xx) equine H5N1 influenza A viruses, (xxi) equine H3N2 influenza A viruses, (xxii) equine H2N2 influenza A viruses, (xxiii) equine H7N7 influenza A viruses and/or (xxiv) equine H7N9 influenza A viruses, alone or in any combination.

Conservation of the epitope between two or more influenza A viruses may allow the vaccine composition to provide protection against multiple influenza A viruses. For example, upon administration to an individual, the vaccine composition may induce an immune response that is protective against infection with some or all of the influenza A viruses possessing the conserved epitope. In this way, a single vaccine composition can be used to prevent or treat infection with a wide variety of influenza A viruses. This may help to overcome some of the problems associated with existing influenza A virus vaccines. In particular, targeting a conserved epitope may avoid the need to frequently develop new vaccines to match the current viral serotype(s) infecting the human population. The vaccine composition of the invention may be used to prevent or treat infection novel strains that emerge mid-season, such as potentially pandemic strains. The vaccine composition of the invention may be used to prevent or treat infection with strains arising from the re-assortment of segments from a swine, equine and/or avian influenza A virus with segment 8 from a human influenza A virus.

In one aspect, the CD8+ T cell epitope may be present in a predicted ORF of at at least 85, least 167 or at least 216 codons in length in a swine, equine and/or avian influenza A virus, such as a swine influenza A virus of serotype H1N1. For example, the CD8+ T cell epitope may be present in an ORF of at least 85, at least 167 or at least 216 codons in length that would arise in a swine, equine and/or avian influenza A virus should segment 8 undergo mutation. For instance, the CD8+ T cell epitope may be present in an ORF of at least 85, at least 167 or at least 216 codons in length that would arise in a swine, equine and/or avian influenza A virus should one or more nucleotides (such as two or more, three or more, four or more, five or more, six or more, seven or more, eight or more, nine or more or ten or more nucleotides) in segment 8 undergo substitution for a different nucleotide. Substitution for a different nucleotide may change a stop codon encoded by segment 8 in the opposite sense to positive sense RNA capable of translation into a codon that encodes an amino acid. For example, substitution of a single nucleotide in a UAG stop codon may give rise to a UAU, UAC, UUG, UCG, UGG, CAG, AAG, or GAG codon encoding an amino acid.

By including an immunogenic peptide that comprises a CD8+ T cell epitope that is present in a predicted ORF of at least 85, at least 167 or at least 216 codons in length in a swine, equine and/or avian influenza A virus in the vaccine composition, the ability of the vaccine composition to protect against potentially pandemic strains of influenza A virus may be improved. For example, doing so may allow the vaccine composition to induce a protective immune response against a swine, equine or avian influenza A virus that acquires the 85 codon, 167 codon or 216 codon NEG8 ORF that is found in human influenza A viruses and confers viral fitness in humans.

NEG8 Peptides

As set out in the Examples, the present inventors have identified a number of peptides that are (i) from a polypeptide encoded by the ORF encoded by segment 8 of human influenza A viruses in the opposite sense to positive sense RNA capable of translation (the NEG8 ORF), and (ii) presented by MHC class I molecules on cells infected with human influenza A virus. Accordingly, the present inventors have identified a number of CD8+ T cell epitopes that are encoded by the NEG8 ORF. The epitopes are set out in Tables 1 and 2 below.

TABLE 1

| SEQ ID NO: | Sequence | Protein ID | Modifications | Confidence | XCorr | m/z [Da] |
|---|---|---|---|---|---|---|
| 16 | WSILMQRGP | NEG8 | | High | 2.14 | 544.29120 |
| 17 | EAGVETMVIL | NEG8 | | High | 1.95 | 531.27979 |
| 18 | IAPSSVKALS | NEG8 | | High | 1.88 | 486.79718 |
| 19 | PMRTPIAFL | NEG8 | | Medium | 1.74 | 349.20383 |
| 20 | ISMNQFLDNS | NEG8 | M3(Oxidation) | Medium | 1.67 | 592.77045 |
| 21 | LMQRGPSTF | NEG8 | | Medium | 1.66 | 518.77515 |
| 22 | FHSSPPMRTP | NEG8 | | Medium | 1.65 | 386.18805 |
| 23 | KITLKFAFNMM | NEG8 | M10 (Oxidation); M11 (Oxidation) | Medium | 1.60 | 688.34729 |
| 24 | LVCVSLLQSAILSL | NEG8 | | Medium | 1.48 | 729.93231 |

TABLE 2

| SEQ ID NO: | Seq. | Protein | Motif | Xcorr | m/z |
|---|---|---|---|---|---|
| 25 | AFNMMFLSM | NSP | A24 | 1.35 | 554.24 |
| 26 | AILSLQTFD | NSP | A24 | 1.10 | 504.26 |
| 27 | DNSSIVISV | NSP | | 1.40 | 467.24 |
| 28 | IAWSILIQ | NS1 | | 1.22 | 472.28 |
| 29 | IVMSVMYR | NSP | A3 | 1.17 | 507.75 |
| 30 | FLICVSPLQL | NSP | A2/24 | 1.76 | 566.81 |
| 31 | GGLPFSLLL | NS1 | | 1.82 | 458.78 |
| 32 | LFLICVSLL | NSP | A24 | 1.74 | 510.81 |
| 33 | SPLQLAILSL | NSP | B7 | 1.90 | 527.82 |
| 34 | IFRFCFGGSG | Polymerase PB2 | | 1.49 | 545.76 |
| 35 | VAASMFRP | NSP | | 1.45 | 447.74 |
| 36 | LSLQTSDLA | NSP | | 1.11 | 474.25 |
| 37 | SIRVSNRS | Polymerase PB2 | | 1.08 | 459.76 |
| 38 | FSVMFLSM | NS1 | | 1.17 | 489.22 |
| 39 | SVKALSSI | HA | A2/24 | 1.15 | 402.74 |
| 40 | ALMSRPRV | NSP | A2 | 1.24 | 465.27 |
| 41 | EGNGEISPT | NSP | | 1.02 | 452.21 |
| 42 | AFNMMFFS | NSP | | 1.06 | 505.69 |
| 43 | PAISRFCF | HA | A24 | 1.48 | 470.73 |
| 44 | AFSVMFLSM | NSP | A24 | 1.36 | 516.74 |
| 45 | LIQRGPATFCL | Matrix protein | A2/24 | 1.36 | 609.83 |
| 46 | LIQRGPATF | Matrix protein | | | |
| 47 | AILSLQTFD | NSP | A24 | 1.10 | 504.26 |
| 48 | ALSSIRVSS | Polymerase PB2 | A2 B7 | 1.10 | 460.25 |
| 49 | FSMMLLSMI | Polymerase PB1 | | 1.00 | 560.76 |
| 50 | SPPMRTPT | PA-X protein | | 1.13 | 451.72 |
| 51 | LIVLAIYRFC | NSP | A24 | 1.11 | 605.86 |
| 52 | SLRTFDLA | NSP | A2 | 1.09 | 461.74 |
| 53 | MLFVQSYFQ | NSP | | 1.05 | 581.79 |

The vaccine composition may comprise one or more of the peptides set out in SEQ ID NOs: 5 to 41. For instance, the vaccine composition may comprise two or more, three or more, four or more, five or more, six or more, seven or more, eight or more, nine or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, or 36 or more of the peptides set out in SEQ ID NOs: 5 to 41, in any combination. The vaccine composition may comprise all of the peptides set out in SEQ ID NOs: 5 to 41.

The vaccine composition may, for example, comprise one or more peptides each consisting of one of the peptides set out in SEQ ID NOs: 5 to 41. The vaccine composition may, for example, comprise one or more peptides each comprising one of the peptides set out in SEQ ID NOs: 5 to 41. A peptide comprising a peptide set out in one of SEQ ID NOs: 5 to 41 may comprise the peptide set out in one of SEQ ID NOs: 5 to 41 and a number of other amino acids at the N terminal and/or the C terminal of the peptide set out in one of SEQ ID NOs: 5 to 41. For instance, the vaccine composition may comprise a peptide comprising a peptide set out in one of SEQ ID NOs: 5 to 41 and one or more, two or more, three or more, four or more, five or more, six or more, seven or more, eight or more, nine or more, ten or more, 15 or more, 20 or more or 25 or more amino acids at the N terminal of the peptide set out in one of SEQ ID NOs: 5 to 41. For instance, the vaccine composition may comprise a peptide comprising a peptide set out in one of SEQ ID NOs: 5 to 41 and one or more, two or more, three or more, four or more, five or more, six or more, seven or more, eight or more, nine or more, ten or more, 15 or more, 20 or more or 25 or more amino acids at the C terminal of the peptide set out in one of SEQ ID NOs: 5 to 41. The number of amino acids at the N terminal and C terminal of the peptide set out in one of SEQ ID NOs: 5 to 41 may be the same or different.

As the NEG8 ORF is highly conserved between human influenza A viruses, SEQ ID NOs: 5 to 41 should also be conserved between human influenza A viruses. A vaccine composition comprising one or more of the peptides set out in SEQ ID NOs: 5 to 41 may therefore possess the advantages associated with the inclusion of a conserved epitope and set out above.

Any of SEQ ID NOs: 5 to 41 may be present in a predicted ORF of at least 167 or at least 216 codons in length in a swine, equine and/or avian influenza A virus. A vaccine composition comprising one or more of the peptides set out in SEQ ID NOs: 5 to 41 may therefore possess the advantages set out above.

Cross-Protective Vaccine Compositions

As set out above, the NEG8 ORF is highly conserved among human influenza A viruses, and is also present in avian, equine and/or swine influenza A viruses. Other ssRNA viruses may similarly possess an ORF that is encoded by at least part of their genome in the opposite sense to positive sense RNA capable of translation, and which is conserved among viruses of the same genus or family. The polypeptide encoded by the ORF, and the CD8+ T cell epitope(s) it contains, may also be conserved.

For example, the ORF, polypeptide and/or epitope may be conserved among influenza B viruses. The ORF, polypeptide and/or epitope may be conserved among influenza C viruses.

The ORF, polypeptide and/or epitope may be conserved among flaviviruses, such as ebolaviruses and/or marburgviruses. For instance, the ORF, polypeptide and/or epitope may be conserved between two or more of ZEBOV, BDBV, RESTV, SUDV, and TAFV. The ORF, polypeptide and/or epitope may be conserved among margburgviruses. For instance, the ORF, polypeptide and/or epitope may be conserved between MARV and RAVV. The ORF, polypeptide and/or epitope may be conserved between ebolaviruses and marburgviruses. For example, the ORF, polypeptide and/or epitope may be conserved between one or more of ZEBOV, BDBV, RESTV, SUDV, and TAFV and one or more of MARV and RAVV.

The ORF, polypeptide and/or epitope may be conserved between flaviviruses. For instance, the ORF, polypeptide and/or epitope may be conserved between two or more of Zika virus, Dengue virus, West Nile virus and yellow fever virus, as well as St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest virus, Omsk Hemorrhagic Fever virus, Powassan virus, Louping Ill virus, Rio Bravo virus, Tyuleniy virus, Ntaya virus and Modoc virus. For example, the ORF, polypeptide and/or epitope may be conserved between Zika virus and Dengue virus, or Zika virus, Dengue virus and West Nile virus. The ORF, polypeptide and/or epitope may be conserved among Zika viruses. For instance, the ORF, polypeptide and/or epitope may be conserved between African Zika virus and Asian Zika virus. The ORF, polypeptide and/or epitope may be conserved among Dengue viruses. For example, the ORF, polypeptide and/or epitope may be conserved between two or more of DENV-1, DENV-2, DENV-3 and DENV-4.

As already mentioned, including a conserved epitope in the vaccine composition may confer protective capability against multiple virus species, strains or serotypes, providing cross-protection within a virus genus and/or family. Accordingly, a single vaccine composition may be used to confer protection against a variety of different ssRNA viruses. This provides a cost-effective means of controlling the spread of ssRNA virus infection. Inclusion of conserved peptides in the vaccine composition may confer protective capability against emerging ssRNA virus strains, assisting in the long-term control of infection. Furthermore, when the ssRNA virus is a flavivirus, including a conserved epitope in the vaccine composition may beneficially prevent or minimise the development of antibody-dependent enhancement of Dengue virus infection following administration of the vaccine composition.

Interaction with HLA Supertypes

The vaccine composition may comprise at least one immunogenic peptide that comprises a CD8+ T cell epitope from a polypeptide encoded by an ORF encoded by at least part of the genome of a ssRNA virus in the opposite sense to positive sense RNA capable of translation, and that interacts with at least two different HLA supertypes. This allows the vaccine composition to elicit a CD8+ T cell response in a greater proportion of individuals to which the vaccine composition is administered. This is because the vaccine composition should be capable of eliciting a CD8+ T cell response in all individuals of an HLA supertype that interacts with the CD8+ T cell epitope. The vaccine composition may comprise at least two, at least three, at least four, at least five, at least ten, at least fifteen, or at least twenty immunogenic peptides that each comprise a CD8+ T cell epitope from a polypeptide encoded by an ORF encoded by at least part of the genome of a ssRNA virus in the opposite sense to positive sense RNA capable of translation and interact with at least two different HLA supertypes. Each immunogenic peptide may interact with at least two, at least three, at least four, at least five, at least six, at least 7, at least 8, at least 9 or at least 10 different HLA supertypes. Each immunogenic peptide may interact with two or more of HLA-A1, HLA-A2, HLA-A3, HLA-A24, HLA-B7, HLA-B8, HLA-B27, HLA-B44, HLA-B58 or HLA-B62, or any other HLA supertype known in the art, in any combination.

The vaccine composition may comprise two or more immunogenic peptides that (i) each comprise a different CD8+ T cell epitope from a polypeptide encoded by an ORF encoded by at least part of the genome of a ssRNA virus in the opposite sense to positive sense RNA capable of translation, and (ii) each interact with a different HLA supertype. Including two or more such immunogenic peptides in the vaccine composition allows the vaccine composition to elicit a CD8+ T cell response in a greater proportion of individuals to which the vaccine composition is administered. This is because the vaccine composition should be capable of eliciting a CD8+ T cell response in all individuals of an HLA supertype that interacts with one of the CD8+ T cell epitopes comprised in the two or more immunogenic peptides. Each CD8+ T cell epitope may interact with HLA-A1, HLA-A2, HLA-A3, HLA-A24, HLA-B7, HLA-B8, HLA-B27, HLA-B44, HLA-B58 or HLA-B62, or any other HLA supertype know in the art. Any combination of immunogenic peptides comprising such a CD8+ T cell epitope is possible.

CD8+ T Cell Epitopes

CD8+ T cell epitopes presented by ssRNA virus-infected cells can be identified in order to directly identify CD8+ T cell epitopes for inclusion in the vaccine composition. This is an efficient and logical method which can be used alone or to confirm the utility of potential CD8+ T cell epitopes identified by MHC motif prediction methodologies.

To perform the method, cells are infected with a ssRNA virus and maintained in culture for a period of around 72 hours at a temperature of around 37° C. Following culture, the cells are then harvested and washed. Next, the cells are lysed, for instance by homogenisation and freezing/thawing in buffer containing 1% NP40. Lysates are cleared by centrifugation at 2000 rpm for 30 minutes to remove cell debris.

MHC/peptide complexes are then isolated from the lysates by immunoaffinity chromatography using protein A/G beads (UltraLink Immobilized Protein A/G, pierce, Rockford, IL) coated with W6/32 (a monoclonal antibody recognising pan MHC class I molecule). To coat the beads with the antibody, the beads are washed with low pH buffer followed by PBS rinses, incubated with 0.5 mg of the antibody at room temperature for 2 hours, and washed three times to remove unbound antibody. For immunoaffinity chromatography, the coated beads are incubated with lysate for 2 hours at room temperature with continuous rocking. The beads are then separated from the lysate by centrifuging at 1000 rpm for 5 minutes. Bound MHC complexes are eluted from the beads by the addition of 0.1% trifluoroacetic acid (TFA), pH 1.5.

The eluate is next heated at 85° C. for 15 minutes to dissociate the bound peptides from the MHC molecules. After cooling to room temperature, peptides are separated from the antibody by centrifugation using, for example, 3 kDa molecular mass cutoff membrane filters (Millipore). The filtrate is concentrated using vacuum centrifugation and reconstituted to a final volume of 100 µl. The purified peptide mixture is fractionated, for example using a C-18 reversed phase (RP) column (e.g. 4.6 mm diameter×150 mm length) using an offline HPLC. For this step, mobile phase A may be 2% acetonitrile (CAN) and 0.1% formic acid (FA) in water, while mobile phase B may be 0.1% FA and 90% CAN in water.

The peptide-containing fractions are then eluted from the column, dried under a vacuum, and analysed by mass spectrometry to identify the sequences of the fractions. The acquired spectral data can then be searched against all databased proteins for the ssRNA virus to identify peptide sequences associated with ssRNA virus. Synthetic peptides may then be made according to the identified sequences and subjected to mass spectrometry to confirm their identity to the peptides in the peptide-containing fractions.

In this method, any type of cells may be infected with any type of ssRNA virus. ssRNA viruses are described in detail below. The cells may be antigen presenting cells. The cells may be hepatoma cells such as HepG2 cells, EBV-transformed lymphoblastoid B cells such as JY cells, or lymphoblasts such as T2 cells.

The direct identification of CD8+ T cell epitopes presented by ssRNA virus-infected cells is advantageous compared to MHC motif prediction methodologies. The immune epitope database (IEDB; http://www.iedb.org) is generated by motif prediction methods, and not functional methods, and contains numerous predicted HLA-specific ssRNA virus T cell epitopes, including some shared epitopes with high MHC binding scores and limited CTL characterization. As both dominant and subdominant epitopes may be presented by ssRNA virus-infected cells, it is difficult to sort out the dominance hierarchies of naturally presented epitopes using the database. Thus, it is not clear from the immune epitope database alone which of the listed epitopes may be expected to efficiently induce a CD8+ T cell response when included in a vaccine composition. The direct identification method set out above provides a mechanism for confirming the utility of the epitopes.

Vaccine compositions based on epitopes presented by ssRNA virus-infected cells, are superior to vaccines based on a viral protein subunit or a motif predicted epitope. Protein processing by the immune system is likely to alter native viral epitopes. Basing a vaccine composition on peptides demonstrated to be presented by infected cells removes this source of uncertainty, because the peptides have already undergone protein processing.

CD4+ T Cell Epitopes

As set out above, the vaccine composition of the invention may comprise an immunogenic peptide comprising a CD4+ T cell epitope. The vaccine composition may comprise two or more, such as three or more, four or more, five our more, ten or more, fifteen or more or twenty or more immunogenic peptides comprising a CD4+ T cell epitope. A CD4+ T cell epitope is a peptide that is capable of (i) presentation by a class II MHC molecule and (ii) recognition by a T cell receptor (TCR) present on a CD4+ T cell. Preferably, recognition by the TCR results in activation of the CD4+ T cell. CD4+ T cell activation may lead to increased proliferation and/or cytokine production.

The CD4+ T cell epitope may be a ssRNA virus CD4+ T cell epitope. That is, the CD4+ T cell epitope may be a peptide that is expressed by one or more ssRNA viruses (such as Influenza A virus, Dengue virus, Zika virus, Ebola virus or Marburg virus) and that is that is capable of (i) presentation by a class II MHC molecule and (ii) recognition by a T cell receptor (TCR) present on a CD4+ T cell. Such peptides are known in the art.

The CD4+ T cell epitope may be a CD4+ T cell epitope other than a ssRNA virus CD4+ T cell epitope. For example, the CD4+ T cell may be expressed by an organism other than a ssRNA virus. The CD4+ T cell epitope may, for example, be expressed by *Clostriudium tetani*. For instance, the CD4+ T cell epitope may be derived from tetanus toxin.

The CD4+ T cell epitope may be a CD4+ T cell epitope that reacts with all class II HLA types, i.e. a so-called "promiscuous" epitope. Inclusion of a promiscuous epitope in the vaccine composition may improve the ability of the vaccine composition to induce an immune response to the immunogenic peptide comprising a CD8+ T cell epitope from a polypeptide encoded by an ORF encoded by at least part of the genome of a ssRNA virus in the opposite sense to positive sense RNA capable of translation. The CD4+ T cell epitope may, for example, comprise the sequence FKLQTMVKLFNRIKNNVA (SEQ ID NO: 54) and/or the sequence LQTMVKLFNRIKNNVAGGC (SEQ ID NO: 55). SEQ ID NOs 54 and 55 are promiscuous epitopes derived from tetanus toxin.

The peptide comprising a CD4+ T cell epitope may be a different peptide from the immunogenic peptide comprising a CD8+ T cell epitope from a polypeptide encoded by an ORF encoded by at least part of the genome of a ssRNA virus in the opposite sense to positive sense RNA capable of translation. The CD4+ T cell epitope may, for instance, be comprised in an additional peptide in the vaccine composition, i.e. in a peptide that does not comprise a CD8+ T cell epitope from a polypeptide encoded by an ORF encoded by at least part of the genome of a ssRNA virus in the opposite sense to positive sense RNA capable of translation. As mentioned above, the additional peptide may comprise one or more CD8+ T cell epitopes and/or one or more B cell epitopes as well as the CD4+ T cell epitope.

The peptide comprising a CD4+ T cell epitope may be the same peptide as the immunogenic peptide comprising a CD8+ T cell epitope from a polypeptide encoded by an ORF encoded by at least part of the genome of a ssRNA virus in the opposite sense to positive sense RNA capable of translation. That is, the immunogenic peptide comprising a CD8+ T cell epitope from a polypeptide encoded by an ORF encoded by at least part of the genome of a ssRNA virus in the opposite sense to positive sense RNA capable of translation may further comprise a CD4+ T cell epitope.

When the peptide comprising a CD4+ T cell epitope also comprises a CD8+ T cell epitope (such as a CD8+ T cell epitope from a polypeptide encoded by an ORF encoded by at least part of the genome of a ssRNA virus in the opposite sense to positive sense RNA capable of translation), the CD8+ epitope may be nested within the CD4+ T cell epitope. CD4+ T cell epitopes are typically longer than CD8+ T cell epitopes. Therefore, extending one or both termini of the CD8+ T cell epitope may yield a longer, CD4+ T cell epitope whose sequence still comprises the CD8+ T cell epitope. Therefore, the CD4+ T cell epitope may comprise a CD8+ T cell epitope, such as a CD8+ T cell epitope from a polypeptide encoded by an ORF encoded by at least part of the genome of a ssRNA virus in the opposite sense to positive sense RNA capable of translation (e.g. an epitope set out in SEQ ID NOs: 5 to 41), extended at its N-terminus or C-terminus. The CD8+ T cell epitope may be extended by 1, 2, 3, 4 or 5 amino acids at its N terminus. The CD8+ T cell epitope may be extended by 1, 2, 3, 4 or 5 amino acids at its C terminus. Preferably, the CD8+ T cell epitope is extended by 3 amino acids at the N terminus, and 3 amino acids at the C terminus. However, the CD8+ T cell epitope need not be extended by the same number of amino acids at each terminus.

The CD8+ T cell epitope nested within a CD4+ T cell epitope may be capable of generating a robust CTL response. The extended peptide (CD4+ T cell epitope) may be capable of inducing T helper mediated cytokine responses. Thus, inclusion of a ssRNA virus peptide comprising a CD8+ T cell epitope and a CD4+ T cell epitope in the vaccine composition may allow the vaccine composition to induce both cytotoxic and helper T cell responses.

B Cell Epitopes

The vaccine composition of the invention may comprise an immunogenic peptide comprising a B cell epitope. The vaccine composition may comprise two or more, such as three or more, four or more, five our more, ten or more, fifteen or more or twenty or more peptides comprising a B cell epitope. A B cell epitope is a peptide that is capable of recognition by a B cell receptor (BCR) present on a B cell. Preferably, recognition by the BCR results in activation and/or maturation of the B cell. B cell activation may lead to increased proliferation, and/or antibody production.

The B cell epitope may be a ssRNA B cell epitope. That is, the B cell epitope may be a peptide that is expressed by one or more ssRNA viruses and that is capable of recognition by a B cell receptor (BCR) present on a B cell. Such peptides are known in the art.

The B cell epitope may be a linear epitope, i.e. an epitope that is defined by the primary amino acid sequence of a particular region of a ssRNA virus protein. Alternatively, the epitope may be a conformational epitope, i.e. an epitope that is defined by the conformational structure of a native ssRNA virus protein. In this case, the epitope may be continuous (i.e. the components that interact with the antibody are situated next to each other sequentially on the protein) or discontinuous (i.e. the components that interact with the antibody are situated on disparate parts of the protein, which are brought close to each other in the folded native protein structure).

Typically, the B cell epitope is around 5 to 20 amino acids in length, such as 6 to 19, 7 to 18, 8 to 17, 9 to 16, 10 to 15, 11 to 14 or 12 to 13 amino acids in length.

Methods for identifying B cell epitopes are also known in the art. For instance, epitope mapping methods may be used to identify B cell epitopes. These methods include structural approaches, wherein the known or modelled structure of a protein is used in an algorithm based approach to predict surface epitopes, and functional approaches, wherein the binding of whole proteins, protein fragments or peptides to an antibody can be quantitated e.g. using an Enzyme-Linked Immunosorbent Assay (ELISA). Competition mapping, antigen modification or protein fragmentation methods may also be used.

Nanoparticles

Any immunogenic peptide comprised in the vaccine composition of the invention may be attached to a nanoparticle. Attachment to a nanoparticle, for example a gold nanoparticle, is beneficial.

Attachment of the peptide to a nanoparticle (such as a gold nanoparticle) reduces or eliminates the need to include a virus or an adjuvant in the vaccine composition. The nanoparticles may contain immune "danger signals" that help to effectively induce an immune response to the peptides. The nanoparticles may induce dendritic cell (DC) activation and maturation, required for a robust immune response. The nanoparticles may contain non-self components that improve uptake of the nanoparticles and thus the peptides by cells, such as antigen presenting cells. Attachment of a peptide to a nanoparticle may therefore enhance the ability of antigen presenting cells to stimulate virus-specific T and/or B cells. Attachment to a nanoparticle also facilitates delivery of the vaccine compositions via the subcutaneous, intradermal, transdermal and oral/buccal routes, providing flexibility in administration.

Nanoparticles are particles between 1 and 100 nanometers (nm) in size which can be used as a substrate for immobilising ligands. In the vaccine compositions of the invention, the nanoparticle may have a mean diameter of 1 to 100, 20 to 90, 30 to 80, 40 to 70 or 50 to 60 nm. Preferably, the nanoparticle has a mean diameter of 20 to 40 nm. A mean diameter of 20 to 40 nm facilitates uptake of the nanoparticle to the cytosol. The mean diameter can be measured using techniques well known in the art such as transmission electron microscopy.

Nanoparticles suitable for the delivery of antigen, such as an immunogenic peptide, are known in the art. Methods for the production of such nanoparticles are also known.

The nanoparticle may, for example, be a polymeric nanoparticle, an inorganic nanoparticle, a liposome, an immune stimulating complex (ISCOM), a virus-like particle (VLP), or a self-assembling protein. The nanoparticle is preferably a calcium phosphate nanoparticle, a silicon nanoparticle or a gold nanoparticle.

The nanoparticle may be a polymeric nanoparticle. The polymeric nanoparticle may comprise one or more synthetic polymers, such as poly(d,1-lactide-co-glycolide) (PLG), poly(d,1-lactic-coglycolic acid) (PLGA), poly(g-glutamic acid) (g-PGA)m poly(ethylene glycol) (PEG), or polystyrene. The polymeric nanoparticle may comprise one or more natural polymers such as a polysaccharide, for example pullulan, alginate, inulin, and chitosan. The use of a polymeric nanoparticle may be advantageous due to the properties of the polymers that may be include in the nanoparticle. For instance, the natural and synthetic polymers recited above may have good biocompatibility and biodegradability, a non-toxic nature and/or the ability to be manipulated into desired shapes and sizes. The polymeric nanoparticle may form a hydrogel nanoparticle. Hydrogel nanoparticles are a type of nano-sized hydrophilic three-dimensional polymer network. Hydrogel nanoparticles have favourable properties including flexible mesh size, large surface area for multivalent conjugation, high water content, and high loading capacity for antigens. Polymers such as Poly(L-lactic acid) (PLA), PLGA, PEG, and polysaccharides are particularly suitable for forming hydrogel nanoparticles.

The nanoparticle may be an inorganic nanoparticle. Typically, inorganic nanoparticles have a rigid structure and are non-biodegradable. However, the inorganic nanoparticle may be biodegradable. The inorganic nanoparticle may comprise a shell in which an antigen may be encapsulated. The inorganic nanoparticle may comprise a core to which an antigen may be covalently attached. The core may comprise a metal. For example, the core may comprise gold (Au), silver (Ag) or copper (Cu) atoms. The core may be formed of more than one type of atom. For instance, the core may comprise an alloy, such as an alloy of Au/Ag, Au/Cu, Au/Ag/Cu, Au/Pt, Au/Pd or Au/Ag/Cu/Pd. The core may comprise calcium phosphate (CaP). The core may comprise a semiconductor material, for example cadmium selenide.

Other exemplary inorganic nanoparticles include carbon nanoparticles and silica-based nanoparticles. Carbon nanoparticles have good biocompatibility and can be synthesized into nanotubes and mesoporous spheres. Silica-based nanoparticles (SiNPs) are biocompatible and can be prepared with tunable structural parameters to suit their therapeutic application.

The nanoparticle may be a silicon nanoparticle, such as an elemental silicon nanoparticle. The nanoparticle may be mesoporous or have a honeycomb pore structure. Preferably, the nanoparticle is an elemental silicon particle having a honeycomb pore structure. Such nanoparticles are known in the art and offer tunable and controlled drug loading, targeting and release that can be tailored to almost any load, route of administration, target or release profile. For example, such nanoparticles may increase the bioavailability of their load, and/or improve the intestinal permeability and absorption of orally administered actives. The nanoparticles may have an exceptionally high loading capacity due to their porous structure and large surface area. The nanoparticles may release their load over days, weeks or months, depending on their physical properties. Since silicon is a naturally occurring element of the human body, the nanoparticles may elicit no response from the immune system. This is advantageous to the in vivo safety of the nanoparticles.

Any of the SiNPs described above may be biodegradable or non-biodegradable. A biodegradable SiNP may dissolve to orthosilic acid, the bioavailable form of silicon. Orthosilic acid has been shown to be beneficial for the health of bones, connective tissue, hair, and skin.

The nanoparticle may be a liposome. Liposomes are typically formed from biodegradable, non-toxic phospholipids and comprise a self-assembling phospholipid bilayer shell with an aqueous core. A liposome may be an unilamellar vesicle comprising a single phospholipid bilayer, or a multilameller vesicle that comprises several concentric phospholipid shells separated by layers of water. As a consequence, liposomes can be tailored to incorporate either hydrophilic molecules into the aqueous core or hydrophobic molecules within the phospholipid bilayers. Liposomes may encapsulate antigen within the core for delivery. Liposomes may incorporate viral envelope glycoproteins to the shell to form virosomes. A number of liposome-based products are established in the art and are approved for human use.

The nanoparticle may be an immune-stimulating complex (ISCOM). ISCOMs are cage-like particles which are typically formed from colloidal saponin-containing micelles. ISCOMs may comprise cholesterol, phospholipid (such as phosphatidylethanolamine or phosphatidylcholine) and saponin (such as Quil A from the tree *Quillaia saponaria*). ISCOMs have traditionally been used to entrap viral envelope proteins, such as envelope proteins from herpes simplex virus type 1, hepatitis B, or influenza virus.

The nanoparticle may be a virus-like particle (VLP). VLPs are self-assembling nanoparticles that lack infectious nucleic acid, which are formed by self-assembly of biocompatible capsid protein. VLPs are typically about 20 to about 150 nm, such as about 20 to about 40 nm, about 30 to about 140 nm, about 40 to about 130 nm, about 50 to about 120 nm, about 60 to about 110 nm, about 70 to about 100 nm, or about 80 to about 90 nm in diameter. VLPs advantageously harness the power of evolved viral structure, which is naturally optimized for interaction with the immune system. The naturally-optimized nanoparticle size and repetitive structural order means that VLPs induce potent immune responses, even in the absence of adjuvant.

The nanoparticle may be a self-assembling protein. For instance, the nanoparticle may comprise ferritin. Ferritin is a protein that can self-assemble into nearly-spherical 10 nm structures. The nanoparticle may comprise major vault protein (MVP). Ninety-six units of MVP can self-assemble into a barrel-shaped vault nanoparticle, with a size of approximately 40 nm wide and 70 nm long.

The nanoparticle may be a calcium phosphate (CaP) nanoparticle. CaP nanoparticles may comprise a core comprising one or more (such as two or more, 10 or more, 20 or more, 50 or more, 100 or more, 200 or more, or 500 or more) molecules of CaP. CaP nanoparticles and methods for their production are known in the art. For instance, a stable nano-suspension of CAP nanoparticles may be generated by mixing inorganic salt solutions of calcium and phosphates in pre-determined ratios under constant mixing.

The CaP nanoparticle may have an average particle size of about 80 to about 100 nm, such as about 82 to about 98 nm, about 84 to about 96 nm, about 86 to about 94 nm, or about 88 to about 92 nm. This particle size may produce a better performance in terms of immune cell uptake and immune response than other, larger particle sizes. The particle size may be stable (i.e. show no significant change), for instance when measured over a period of 1 month, 2 months, 3 months, 6 months, 12 months, 18 months, 24 months, 36 months or 48 months.

CaP nanoparticles can be co-formulated with one or multiple antigens either adsorbed on the surface of the nanoparticle or co-precipitated with CaP during particle synthesis. For example, a peptide, such as an immunogenic peptide, may be attached to the CaP nanoparticle by dissolving the peptide in DMSO (for example at a concentration of about 10 mg/ml), adding to a suspension of CaP nanoparticles together with N-acetyl-glucosamine (GlcNAc) (for example at 0.093 mol/L and ultra-pure water, and mixing at room temperature for a period of about 4 hours (for example, 1 hour, 2 hours, 3 hours, 5 hours, 6 hours, 7 hours, 8 hours, 9 hours or 10 hours).

The vaccine composition may comprise about 0.15 to about 0.8%, such as 0.2 to about 0.75%, 0.25 to about 0.7%, 0.3 to about 0.6%, 0.35 to about 0.65%, 0.4 to about 0.6%, or 0.45 to about 0.55%, CaP nanoparticles. Preferably the vaccine composition comprises about 0.3% CaP nanoparticles.

CaP nanoparticles have a high degree of biocompatibility due to their chemical similarity to human hard tissues such as bone and teeth. Advantageously, therefore, CaP nanoparticles are non-toxic when used for therapeutic applications. CaP nanoparticles are safe for administration via intramuscular, subcutaneous, oral, or inhalation routes. CaP nanoparticles are also simple to synthesise commercially. Furthermore, CaP nanoparticles may be associated with slow release of antigen, which may enhance the induction of an immune response to a peptide attached to the nanoparticle. CaP nanoparticles may be used both as an adjuvant, and as a drug delivery vehicle.

The nanoparticle may be a gold nanoparticle. Gold nanoparticles are known in the art and are described in particular in WO 2002/32404, WO 2006/037979, WO 2007/122388, WO 2007/015105 and WO 2013/034726. The gold nanoparticle attached to each peptide may be a gold nanoparticle described in any of WO 2002/32404, WO 2006/037979, WO 2007/122388, WO 2007/015105 and WO 2013/034726.

Gold nanoparticles comprise a core comprising a gold (Au) atom. The core may further comprise one or more Fe, Cu or Gd atoms. The core may be formed from a gold alloy, such as Au/Fe, Au/Cu, Au/Gd, Au/Fe/Cu, Au/Fe/Gd or Au/Fe/Cu/Gd. The total number of atoms in the core may be 100 to 500 atoms, such as 150 to 450, 200 to 400 or 250 to 350 atoms. The gold nanoparticle may have a mean diameter of 1 to 100, 20 to 90, 30 to 80, 40 to 70 or 50 to 60 nm. Preferably, the gold nanoparticle has a mean diameter of 20 to 40 nm.

The nanoparticle may comprise a surface coated with alpha-galactose and/or beta-GlcNHAc. For instance, the nanoparticle may comprise a surface passivated with alpha-galactose and/or beta-GlcNHAc. In this case, the nanoparticle may, for example, be a nanoparticle which comprises a core including metal and/or semiconductor atoms. For instance, the nanoparticle may be a gold nanoparticle. Beta-GlcNHAc is a bacterial pathogen-associated-molecular pattern (PAMP), which is capable of activating antigen-presenting cells. In this way, a nanoparticle comprising a surface coated or passivated with Beta-GlcNHAc may non-specifically stimulate an immune response. Attachment of an immunogenic peptide to such a nanoparticle may therefore improve the immune response elicited by administration of the vaccine composition of the invention to an individual.

One or more ligands other than the peptide may be linked to the nanoparticle, which may be any of the types of nanoparticle described above. The ligands may form a "corona", a layer or coating which may partially or completely cover the surface of the core. The corona may be considered to be an organic layer that surrounds or partially surrounds the nanoparticle core. The corona may provide or participate in passivating the core of the nanoparticle. Thus, in certain cases the corona may be a sufficiently complete coating layer to stabilise the core. The corona may facilitate solubility, such as water solubility, of the nanoparticles of the present invention.

The nanoparticle may comprise at least 10, at least 20, at least 30, at least 40 or at least 50 ligands. The ligands may include one or more peptides, protein domains, nucleic acid molecules, lipidic groups, carbohydrate groups, anionic groups, or cationic groups, glycolipids and/or glycoproteins. The carbohydrate group may be a polysaccharide, an oligosaccharide or a monosaccharide group (e.g. glucose). One or more of the ligands may be a non-self component, that renders the nanoparticle more likely to be taken up by antigen presenting cells due to its similarity to a pathogenic component. For instance, one or more ligands may comprise a carbohydrate moiety (such as a bacterial carbohydrate moiety), a surfactant moiety and/or a glutathione moiety. Exemplary ligands include glucose, N-acetylglucosamine (GlcNAc), glutathione, 2'-thioethyl-β-D-glucopyranoside and 2'-thioethyl-D-glucopyranoside. Preferred ligands include glycoconjugates, which form glyconanoparticles Linkage of the ligands to the core may be facilitated by a linker. The linker may comprise a thiol group, an alkyl group, a glycol group or a peptide group. For instance, the linker may comprise C2-C15 alkyl and/or C2-C15 glycol. The linker may comprise a sulphur-containing group, amino-containing group, phosphate-containing group or oxygen-containing group that is capable of covalent attachment to the core. Alternatively, the ligands may be directly linked to the core, for example via a sulphur-containing group, amino-containing group, phosphate-containing group or oxygen-containing group comprised in the ligand.

Attachment to Nanoparticles

An immunogenic peptide may be attached at its N-terminus to the nanoparticle. Typically, the immunogenic peptide may be attached to the core of the nanoparticle, but attachment to the corona or a ligand may also be possible.

The peptide may be directly attached to the nanoparticle, for example by covalent bonding of an atom in a sulphur-containing group, amino-containing group, phosphate-containing group or oxygen-containing group in the peptide to an atom in the nanoparticle or its core.

A linker may be used to link the peptide to the nanoparticle. The linker may comprise a sulphur-containing group, amino-containing group, phosphate-containing group or oxygen-containing group that is capable of covalent attachment to an atom in the core. For example, the linker may comprise a thiol group, an alkyl group, a glycol group or a peptide group.

The linker may comprise a peptide portion and a non-peptide portion. The peptide portion may comprise the sequence $X_1X_2Z_1$, wherein $X_1$ is an amino acid selected from A and G; $X_2$ is an amino acid selected from A and G; and $Z_1$ is an amino acid selected from Y and F. The peptide portion may comprise the sequence AAY or FLAAY. The peptide portion of the linker may be linked to the N-terminus of the peptide. The non-peptide portion of the linker may comprise a C2-C15 alkyl and/a C2-C15 glycol, for example a thioethyl group or a thiopropyl group.

The linker may be (i) HS—$(CH_2)_2$—CONH-AAY; (ii) HS—$(CH_2)_2$—CONH-LAAY; (iii) HS—$(CH_2)_3$—CONH-AAY; (iv) HS—$(CH_2)_3$—CONH-FLAAY; (v) HS—$(CH_2)_{10}$—$(CH_2OCH_2)_7$—CONH-AAY; and (vi) HS—$(CH_2)_{10}$—$(CH_2OCH_2)_7$—CONH-FLAAY. In this case, the thiol group of the non-peptide portion of the linker links the linker to the core.

Other suitable linkers for attaching a peptide to a nanoparticle are known in the art, and may be readily identified and implemented by the skilled person.

As explained above, the vaccine composition may comprise multiple immunogenic peptides. When the vaccine composition comprises more than one immunogenic peptide, two or more (such as three or more, four or more, five or more, ten or more, or twenty or more) of the immunogenic peptides may be attached to the same nanoparticle. Two or more (such as three or more, four or more, five or more, ten or more, or twenty or more) of the immunogenic peptides may each be attached to different nanoparticle. The nanoparticles to which the immunogenic peptides are attached may though be the same type of nanoparticle. For instance, each immunogenic peptide may be attached to a gold nanoparticle. Each immunogenic peptide may be attached to a CaP nanoparticle. The nanoparticle to which the immunogenic peptides are attached may be a different type of nanoparticle. For instance, one immunogenic peptide may be attached to a gold nanoparticle, and another immunogenic peptide may be attached to a CaP nanoparticle.

Medicaments, Methods and Therapeutic Use

The invention provides a method of preventing or treating a viral infection, comprising administering the vaccine composition of the invention to an individual infected with, or at risk of being infected with, a ssRNA virus. The invention also provides a vaccine composition of the invention for use in a method of preventing or treating a ssRNA virus infection in an individual.

The individual may, for example, be human. The individual may, for example, be a swine, a horse or a bird.

The ssRNA virus infection may be caused by a zoonotic virus. The ssRNA virus infection may be a pandemic viral infection.

The ssRNA virus infection may be, for example, an orthomyxovirus infection. The orthomyxovirus infection may be, for instance, an influenza virus infection. The influenza virus may be an influenza A, influenza B and/or influenza C virus. The influenza A virus may, for example, be of serotype H1N1, H5N1, H7N9, H7N7, H2N2 or H3N2. The influenza virus may be a human influenza virus, a swine influenza virus, an equine influenza virus, or an avian influenza virus. The influenza virus may be a pandemic influenza virus or a potentially pandemic influenza virus.

The ssRNA virus infection may be, for example, a flavivirus infection. The flavivirus infection may be, for example, a Zika virus infection, a Dengue virus infection, a West Nile virus infection, a yellow fever virus infection, a St. Louis encephalitis virus infection, a Japanese encephalitis virus infection, a Murray Valley encephalitis virus infection, a Tick-borne encephalitis virus infection, a Kunjin encephalitis virus infection, a Rocio encephalitis virus infection, a Russian Spring Summer encephalitis virus infection, Negeishi virus infection, a Kyasanur Forest infection, a Omsk Hemorrhagic Fever virus infection, a Powassan virus infection, a Louping Ill virus infection, a Rio Bravo virus infection, a Tyuleniy virus infection, a Ntaya virus infection or a Modoc virus infection. The Zika virus infection may, for example, be African Zika Virus infection or Asian Zika Virus infection. The Dengue virus may, for example, be DENV-1 infection, DENV-2 infection, DENV-3 infection or DENV-4 infection.

The ssRNA virus infection may be, for example, a filovirus infection. The filovirus infection may be, for example, an ebolavirus infection or marburgvirus infection. The ebolavirus infection may be, for instance, a Zaire ebolavirus (ZEBOV), Sudan ebolavirus (SUDV), Reston ebolavirus (RESTV), Tai Forest ebolavirus (TAFV) or Bundibugyo ebolavirus (BDBV) infection. The marburgvirus infection may be, for instance, a Marburg virus (MARV) or Ravn virus (RAVV) infection The vaccine composition may be provided as a pharmaceutical composition. The pharmaceutical composition preferably comprises a pharmaceutically acceptable carrier or diluent. The pharmaceutical composition may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, 19th Edition, Mack Publishing Company, Eastern Pennsylvania, USA.

The vaccine composition or pharmaceutical composition may be administered by any route. Suitable routes include, but are not limited to, the intravenous, intramuscular, intraperitoneal, subcutaneous, intradermal, transdermal and oral/buccal routes.

Compositions may be prepared together with a physiologically acceptable carrier or diluent. Typically, such compositions are prepared as liquid suspensions of peptides and/or peptide-linked nanoparticles. The peptides and/or peptide-linked nanoparticles may be mixed with an excipient which is pharmaceutically acceptable and compatible with the active ingredient. Suitable excipients are, for example, water, saline, dextrose, glycerol, of the like and combinations thereof.

In addition, if desired, the pharmaceutical compositions may contain minor amounts of auxiliary substances such as wetting or emulsifying agents, and/or pH buffering agents.

The peptides or peptide-linked nanoparticles are administered in a manner compatible with the dosage formulation and in such amount will be therapeutically effective. The quantity to be administered depends on the subject to be treated, the disease to be treated, and the capacity of the subject's immune system. Precise amounts of nanoparticles required to be administered may depend on the judgement of the practitioner and may be peculiar to each subject.

Any suitable number of peptides or peptide-linked nanoparticles may be administered to a subject. For example, at least, or about, $0.2\times10^6$, $0.25\times10^6$, $0.5\times10^6$, $1.5\times10^6$, $4.0\times10^6$ or $5.0\times10^6$ peptides or peptide-linked nanoparticles per kg of patient may administered. For example, at least, or about, $10^5$, $10^6$, $10^7$, $10^8$, $10^9$ peptides or peptide-linked nanoparticles may be administered. As a guide, the number of peptides or peptide-linked nanoparticles to be administered may be from $10^5$ to $10^9$, preferably from $10^6$ to $10^8$.

Methods

The invention provides a method of identifying an immunogenic peptide comprising a CD8+ T cell epitope from an open reading frame ORF encoded by at least part of the genome of a ssRNA virus in the opposite sense to positive sense RNA capable of translation by: (a) identifying an ORF encoded by at least part of the genome of a ssRNA virus in the opposite sense to positive sense RNA capable of translation; (b) predicting the sequence of the polypeptide encoded by the ORF; and (c) assessing whether a peptide that binds a MHC Class I molecule comprises a sequence present in the predicted sequence, thereby identifying an immunogenic peptide comprising a CD8+ T cell epitope.

The immunogenic peptide may be any of the immunogenic peptides discussed above. The CD8+ T cell epitope may be any of the CD8+ T cell epitopes discussed above. The ssRNA virus may be any of the ssRNA viruses discussed above. Preferably, the ssRNA virus is an influenza A virus.

The ORF may be any of the ORFs discussed above. The ORF may, for example, be a NEG8 ORF. In some aspects, the ORF comprises a stop codon. In this case, the predicted sequence is predicted on the basis that the ORF is mutated to a codon encoding an amino acid and the peptide comprises a sequence present in a part of the predicted sequence that is C-terminal to the mutated codon.

Methods for identifying an ORF encoded by at least part of the genome of a ssRNA virus in the opposite sense to positive sense RNA capable of translation are well known in the art. For example, the ORF may be identified by analysing the sequence of the genome a ssRNA virus in the opposite sense to positive sense RNA capable of translation. As set out above, an ORF is a continuous stretch of codons that contains a start codon and a stop codon. If the sequence of the genome a ssRNA virus in the opposite sense to positive sense RNA capable of translation comprises such a stretch of codons, it may comprise an ORF.

Methods for predicting the sequence of the polypeptide encoded by the ORF are routine in the art. For instance, in the knowledge of the genetic code, the skilled person may easily determine the amino acid sequence of the polypeptide from the codons comprised in the ORF.

Methods for assessing whether a peptide that binds a MHC Class I molecule comprises a sequence present in the predicted sequence are also known. For instance, peptides that bind to a MHC class I molecule can be determined as set out in the "CD8+ T cell epitopes" section above. In brief, cells are infected with a ssRNA virus, cultured, harvested and washed. The cells are lysed and MHC/peptide complexes are then isolated from the lysates by immunoaffinity chromatography. MHC complexes obtained by immunoaffinity chromatography are heated to dissociate the bound peptides from the MHC molecules. The peptide mixture is purified and analysed by mass spectrometry to identify the sequences of the peptides. The sequence of the peptide can then be compared to the predicted sequence to determine whether or not the peptide comprises a sequence present in the predicted sequence. In other words, the predicted sequence may be compared to that of a sequence known or newly shown to bind a MHC class I molecule. If, for example, there is identity between the predicted sequence and the peptide over some (e.g. 10%, 20%, 25%, 30%, 40%, 50%, 60%, 70%, 75%, 80%, 90%, 95%, 97%, 98% or 99%) or all of the length of the peptide, the peptide may comprise a sequence present in the predicted sequence. There may, for instance, be at least 50% identity (such as at least 55%, at least 60%, at least 65%, at least 70%, at least 75%, at least 80%, at least 85%, at least 90% m at least 95%, at least 97%, at least 98% or at least 99% identity) between the peptide and the predicted sequence over some or all of the length of the peptide, based on amino acid identity.

As the immunogenic peptide comprises a CD8+ T cell epitope, it is expected to be capable of inducing a CD8+ T cell response. The method of the invention may further comprise one or more steps that help to confirm whether or not this is the case. For example, the method may further comprise (d) contacting CD8+ T cells obtained from an individual infected with, or previously infected with, the ssRNA virus with the peptide; and (e) measuring in vitro the immune response to the peptide. In other words, CD8+ T cells obtained from an individual infected with, or previously infected with, the ssRNA virus are stimulated with the immunogenic peptide to determine whether the CD8+ T cell population comprises CD8+ T cells specific for the epitope comprised in the immunogenic peptide. Methods for measuring the immune response in vitro are well known in the art. For example, the proliferation of CD8+ T cells may be measured. IFNγ production may be measured, for instance by assaying IFNγ into the culture supernatant or investigating intracellular IFNγ using flow cytometry. Expression of CD107a, a marker of degranulation, may be measured using flow cytometry.

Immunogenic Peptides

The invention provides an immunogenic peptide comprising a CD4+ T cell epitope or a B cell epitope from a polypeptide encoded by an open reading frame (ORF) encoded by at least part of the genome of a ssRNA virus in the opposite sense to positive sense RNA capable of translation.

A CD4+ T cell epitope is a peptide that is capable of (i) presentation by a class II MHC molecule and (ii) recognition by a T cell receptor (TCR) present on a CD4+ T cell. Preferably, recognition by the TCR results in activation of the CD4+ T cell. CD4+ T cell activation may lead to increased proliferation and/or cytokine production.

A B cell epitope is a peptide that is capable of recognition by a B cell receptor (BCR) present on a B cell. Preferably, recognition by the BCR results in activation and/or maturation of the B cell. B cell activation may lead to increased proliferation, and/or antibody production.

The immunogenic peptide may be used in a vaccine composition. Any of the aspects described above in relation to a vaccine composition comprising an immunogenic peptide comprising a CD8+ T cell epitope or a B cell epitope from a polypeptide encoded by an ORF encoded by at least part of the genome of a ssRNA virus in the opposite sense to positive sense RNA capable of translation may equally apply to a vaccine composition comprising an immunogenic peptide comprising a CD4+ T cell epitope or a B cell epitope from a polypeptide encoded by an ORF encoded by at least part of the genome of a ssRNA virus in the opposite sense to positive sense RNA capable of translation Administration of a vaccine composition comprising the immunogenic peptide may induce a protective immune response against the ssRNA virus. For example, administration of the vaccine composition may induce a CD4+ T cell response against the ssRNA virus. Administration of the vaccine composition may induce a B cell response against the ssRNA virus. In this way, humoral immunity against the ssRNA virus may be induced.

The immunogenic peptide may be used in an assay for diagnosing infection with the ssRNA virus. For instance, the immunogenic peptide may be used to detect antibodies against the ssRNA virus, such as antibodies specific for the B cell epitope comprised in the immunogenic peptide. The immunogenic peptide may be used to detect B cells specific against the ssRNA virus, such as B cells whose B cell receptor is specific for the B cell epitope comprised in the immunogenic peptide. The immunogenic peptide may be used to detect CD4+ T cells specific for the ssRNA virus, such as CD4+ T cells specific for the CD4+ T cell epitope comprised in the immunogenic peptide.

Identifying Pandemic Potential

Traditionally, influenza A virus pandemics have been associated with a global change in the HA serotype of the virus. However, the inventors have noted that certain influenza A virus outbreaks have not been associated with a change in HA serotype, but rather a change in the codon length of an ORF encoded by at least part of the genome of the influenza A virus in the opposite sense to positive sense RNA capable of translation.

Accordingly, the present invention provides a method of determining the pandemic potential of an influenza A virus, the method comprising the steps of: (i) identifying a first ORF encoded by at least part of segment 8 of the genome of the influenza A virus in the opposite sense to positive sense RNA capable of translation; (ii) determining the number of codons comprised in the first ORF; and (iii) comparing the number of codons comprised in the first ORF to the number of codons comprised in a second ORF encoded by at least part of segment 8 of the genome of a known pandemic influenza A virus in the opposite sense to positive sense RNA capable of translation, wherein a difference in the number of codons in the first ORF compared to the second ORF is indicative of pandemic potential.

In the context of the invention, pandemic potential means the ability of an influenza A virus to cause an influenza pandemic. An influenza pandemic occurs when a new influenza virus emerges and spreads around the world.

The first ORF may comprise any nucleotide sequence. The first ORF may encode any polypeptide sequence. The second ORF may comprise any nucleotide sequence. The second ORF may encode any polypeptide sequence.

The first ORF may be of any length i.e. comprise any number of codons. The second ORF may be of any length i.e. comprise any number of codons. Exemplary ORF lengths are discussed above.

The first and second ORFs may differ in length by any number of codons. For example, a difference of one or more, two or more, three or more, four or more, five or more, six or more, seven or more, eight or more, nine or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, 75 or more, 80 or more, 90 or more or 100 or more codons may be indicative of pandemic potential.

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a peptide" includes "peptides", reference to "a nanoparticle" includes two or more such nanoparticles, and the like.

All publications, patents and patent applications cited herein, whether supra or infra, are hereby incorporated by reference in their entirety.

The following Examples illustrate the invention.

Example 1—Identification of CD8+ T Cell Epitopes

Cell Lines

HepG2 hepatoma cells were obtained from ATCC andmaintained in DMEM:F12 (Mediatech, Manassas, VA). Culture medium was supplemented with 10% fetal bovine serum, L-glutamine (300 mg/mL), non-essential amino acids (1× concentration), 0.5 mM sodium pyruvate, penicillin and streptomycin (1× concentration, supplements were purchased from Mediatech) [complete medium]. Cells were maintained at 37° C. in a humidified incubator with 5% C02.

Preparation of Samples for MHC Peptide Analysis

HepG2 cells were grown to about 1E9 cells. These cells were then infected with PR8 strain influenza A virus. After a 1 hr pulse, virus was washed away, and cells were incubated for 72 hrs at 37° C. At this point, cells were harvested and processed for MHC peptide analysis.

Isolation, Purification and Fractionation of MHC Class I Bound Peptides

Infected cells were lysed by homogenization and freeze/thawed in buffer containing 1.0% NP40. The lysates were cleared by centrifugation at 2000 rpm for 30 minutes to remove the cell debris. MHC/peptide complexes were isolated by immunoaffinity chromatography using W6/32 antibody (monoclonal antibody recognizing pan MHC class I molecule) coated protein A/G beads (UltraLink Immobilized Protein A/G, Pierce, Rockford, IL). 400 μl Protein A/G beads were washed with low pH buffer followed by PBS rinses. The beads were then incubated with 0.5 mg of the antibody at room temperature for 2 hours. Labelled beads were washed three times to remove unbound antibodies, and antibody-coated beads were added to the prepared cell lysate. After a two-hour incubation at room temperature with continuous rocking, the beads were separated from the lysate by centrifuging at 1000 rpm for 5 minutes. The bound MHC complexes were eluted from the beads by the addition of 0.1% Trifluoroacetic acid, (TFA), pH 1.5. Next, the eluate was heated at 85° C. for 15 min to dissociate the bound peptides from the MHC molecules. After the solution was cooled to room temperature, peptides were separated from the antibody by centrifugation using Amicon Ultra-3 kDa molecular mass cutoff membrane filters (Millipore). The filtrate was concentrated using vacuum centrifugation and reconstituted to a final volume of 100 μL. The purified peptide mixture was fractionated using C-18 reversed phase (RP) column (4.6 mm diameter×150 mm length) using an offline ultimate 3000 HPLC (Dionex, Sunnyvale, CA). Mobile phase A was 2% acetonitrile (ACN) and 0.1% formic acid (FA) in water, while mobile phase B was 0.1% FA and 90% ACN in water. Peptides were then eluted from the column with an 80 min linear gradient from 5 to 80% buffer B at a flow rate of 200 μL/min. A total of 35 fractions were collected and dried to 6 μL under vacuum for LC/MS/MS analysis.

Mass Spectrometry Analysis

Mass spectrometry experiments were carried out using LTQ (Thermo) and Orbitrap instruments interfaced with nano ultimate HPLC (Dionex). RP-HPLC purified peptide fractions were injected individually into the LC-MS/MS system to identify the sequences of the peptides. As a part of the on-line sample clean-up step, the peptides were first concentrated using a 300 μm ID×5mmC18 RP trap column (Dionex, Sunnyvale CA) and then separated using a 75 μm ID×15 cm C18 RP analytical column (Dionex, Sunnyvale CA), equilibrated in 4% ACN/0.1% FA at 250 nL/min flow rate. Mobile phase A was 2% ACN and 0.1% FA in water, while mobile phase B was 0.1% FA and 90% ACN in water. Peptides were separated with a gradient of 4% to 50% B in 60 min and 50% to 80% in 90 min and eluted directly into the mass spectrometer. The mass range in MS mode was 350

Da to 1500 Da and in MS/MS mode it was set as 100 Da to 1500 Da. The peptides were analyzed using a Data-Dependent method. The acquired spectra data were searched against an influenza A protein database using Proteome Discoverer (Thermo) to interpret data and derive peptide sequences. The sequences of peptides bound to MHC class I in PR8-infected cells was logged in a database.

Identification of MHC Peptides in the NEG8 ORF

The database of peptides found to bind MHC class I in PR8-infected cells was searched against the sequence of the polypeptide (SEQ ID NO: 2; MLFVQSYFPLFLV CVSLLQSAILSLQTFDLAVLAIFRFCFGVSGGP-PFSLLLLQANLCRFLETRTVLSFHS SPPMRTPIAFLTS-SIVCPGKEGNGEISPTIAPSSVKALSNTMVSSR-SKITLKFAFNMM FFSMIAWSILMQRGPSTFCL-GISMNQFLDNSSIVMSVMYREAGVETMVILSASSDSS FRIFSTICFPTWVAALMSRPRVLPLPLRDL) encoded by the NEG8 ORF. The NEG8 polypeptide was found to comprise a number of peptides that bind to MHC class I in influenza A virus-infected cells. Table 3 below shows peptides encoded by the NEG8 ORF that bind to MHC class I in influenza A virus-infected cells.

TABLE 3

| SEQ ID NO: | Sequence | Protein ID | Modifications | Confidence | XCorr | m/z [Da] |
|---|---|---|---|---|---|---|
| 5 | WSILMQRGP | NEG8 | | High | 2.14 | 544.29120 |
| 6 | EAGVETMVIL | NEG8 | | High | 1.95 | 531.27979 |
| 7 | IAPSSVKALS | NEG8 | | High | 1.88 | 486.79718 |
| 8 | PMRTPIAFL | NEG8 | | Medium | 1.74 | 349.20383 |
| 9 | ISMNQFLDNS | NEG8 | M3(Oxidation) | Medium | 1.67 | 592.77045 |
| 10 | LMQRGPSTF | NEG8 | | Medium | 1.66 | 518.77515 |
| 11 | FHSSPPMRTP | NEG8 | | Medium | 1.65 | 386.18805 |
| 12 | KITLKFAFNMM | NEG8 | M10 (Oxidation); M11 (Oxidation) | Medium | 1.60 | 688.34729 |
| 13 | LVCVSLLQSAILSL | NEG8 | | Medium | 1.48 | 729.93231 |

Example 2

The identity of five peptides encoded by the NEG8 ORF and found to bind MHC class I in influenza A virus-infected cells was confirmed using synthetic peptide mass spec analysis. The five peptides shown in Table 3 were synthesised and subjected to LC-MS/MS analysis under identical experimental conditions as described above. The spectrum obtained for each peptide as isolated from influenza A virus-infected cells with the spectrum obtained for its synthetic analog in order to confirm the sequence of each peptide. Results are shown in Table 4 and FIGS. 1 to 3.

TABLE 4

| Seq. | Origin | Motif | Virus origin | Cell type | Confirmation |
|---|---|---|---|---|---|
| EAGVE TMVIL | Polypeptide | A2 | NEG8, NSP [Influenza A virus (A/Moscow/343/ 2003(H3N2))], NSP [Influenza A virus (A/Moscow/328/ 2003(H3N2))] | Flu virus infected cells | No |
| IAPSSV KALS | Flu virus infected cells | No | NEG8, NSP [Influenza A virus (A/Moscow/343/ 2003(H3N2))], NSP [Influenza A virus (A/Moscow/328/ 2003(H3N2))] | Flu virus infected cells | Yes |
| IAPSSV KALS | Transmembrane protein | A2 | NEG8, NSP [Influenza A virus (A/Moscow/343/ 2003(H3N2))], NSP [Influenza A virus (A/Moscow/328/ 2003(H3N2))] | Flu virus infected cells | Yes |

TABLE 4-continued

| Seq. | Origin | Motif | Virus origin | Cell type | Confirmation |
|---|---|---|---|---|---|
| PMRTPI AFL | Transmembrane protein | A2/24 | NEG8, NSP [Influenza A virus (A/Moscow/343/2003(H3N2))], NSP [Influenza A virus (A/Moscow/328/2003(H3N2))] | Flu virus infected cells | No |
| LMQRG PSTF | Transmembrane protein | A24 | NEG8, NSP [Influenza A virus (A/Moscow/343/2003(H3N2))], NSP [Influenza A virus (A/Moscow/328/2003(H3N2))] | Flu virus infected cells | Yes |

Figure 1B:
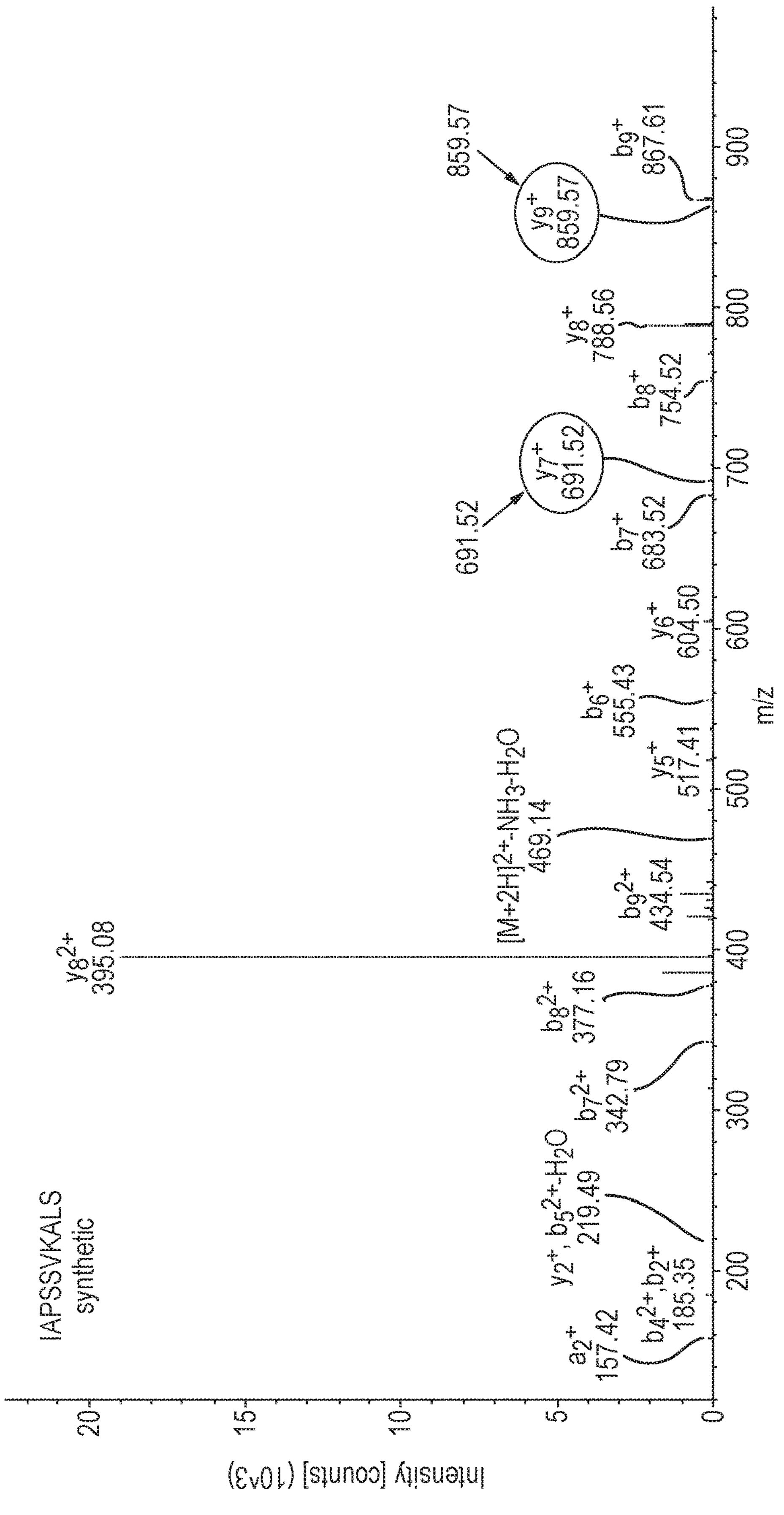
Figure 2A:
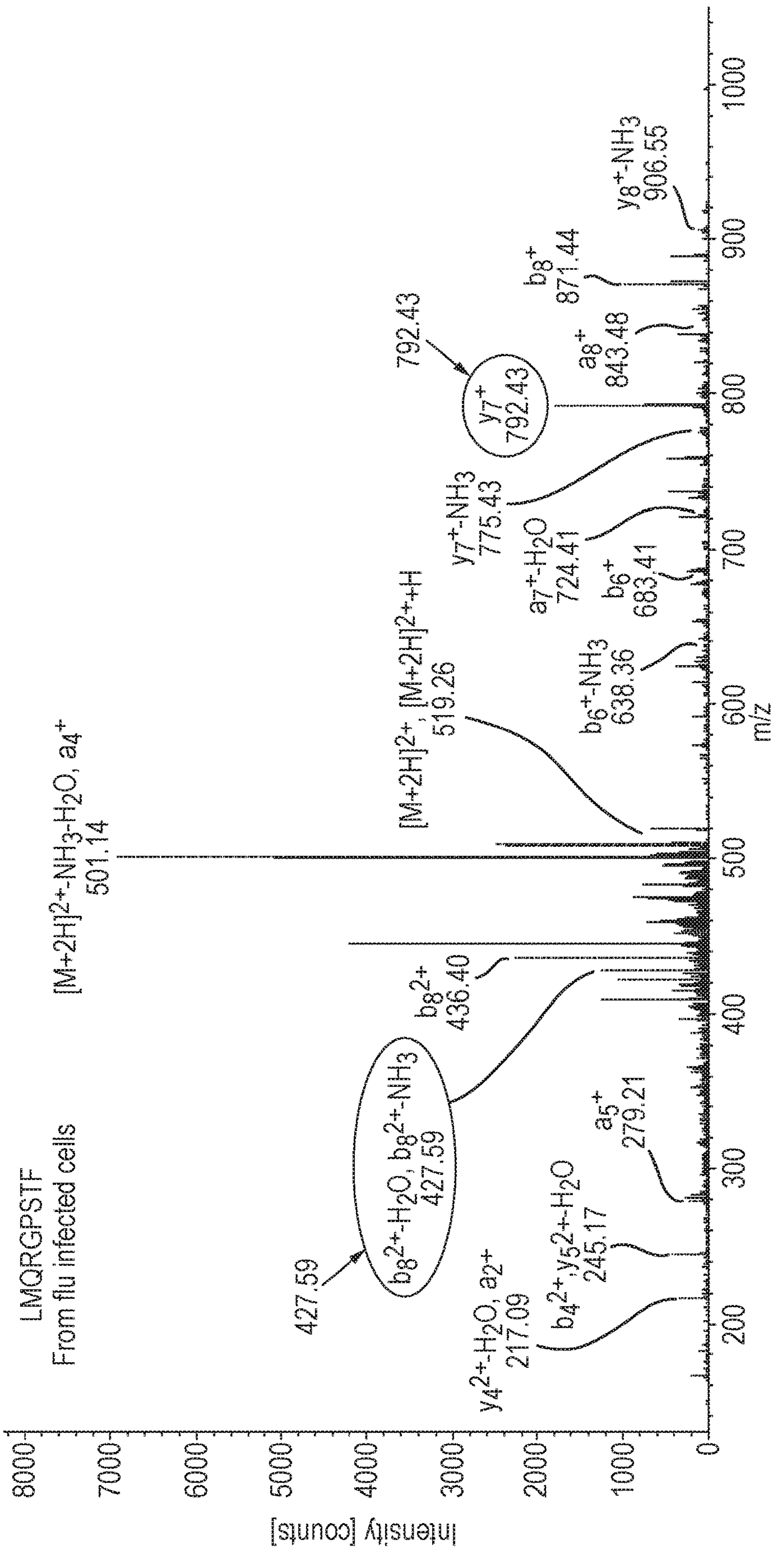
FIG. 2: Comparison of mass spectra of LMQRGPSTF from influenza virus A infected cells (A) and synthetic LMQRGPSTF peptide (B). Some typical ions in each spectrum are circled to emphasise the identity of the peptide from infected cells with that synthesised.
Figure 2B:
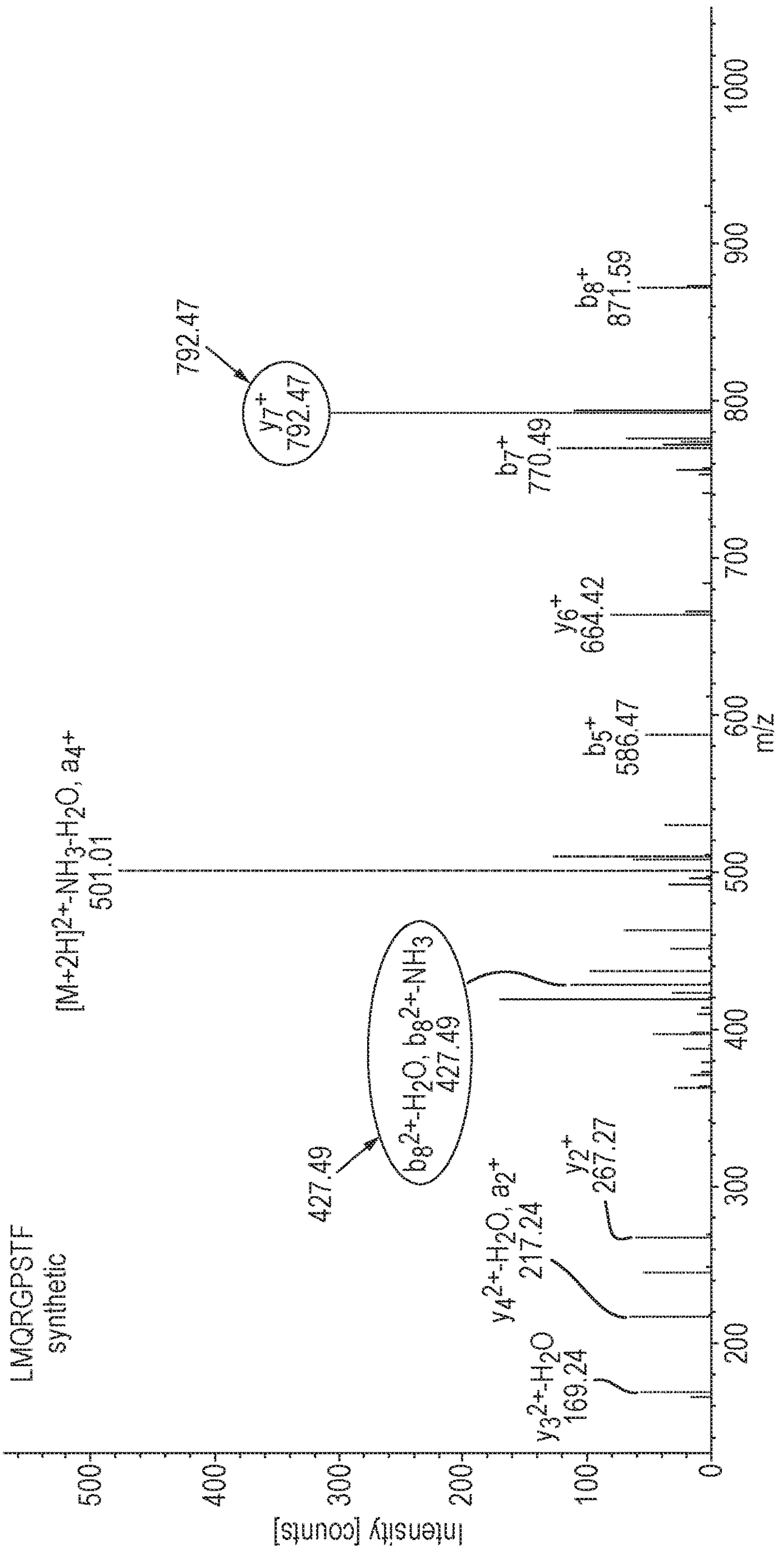
Figure 3A:
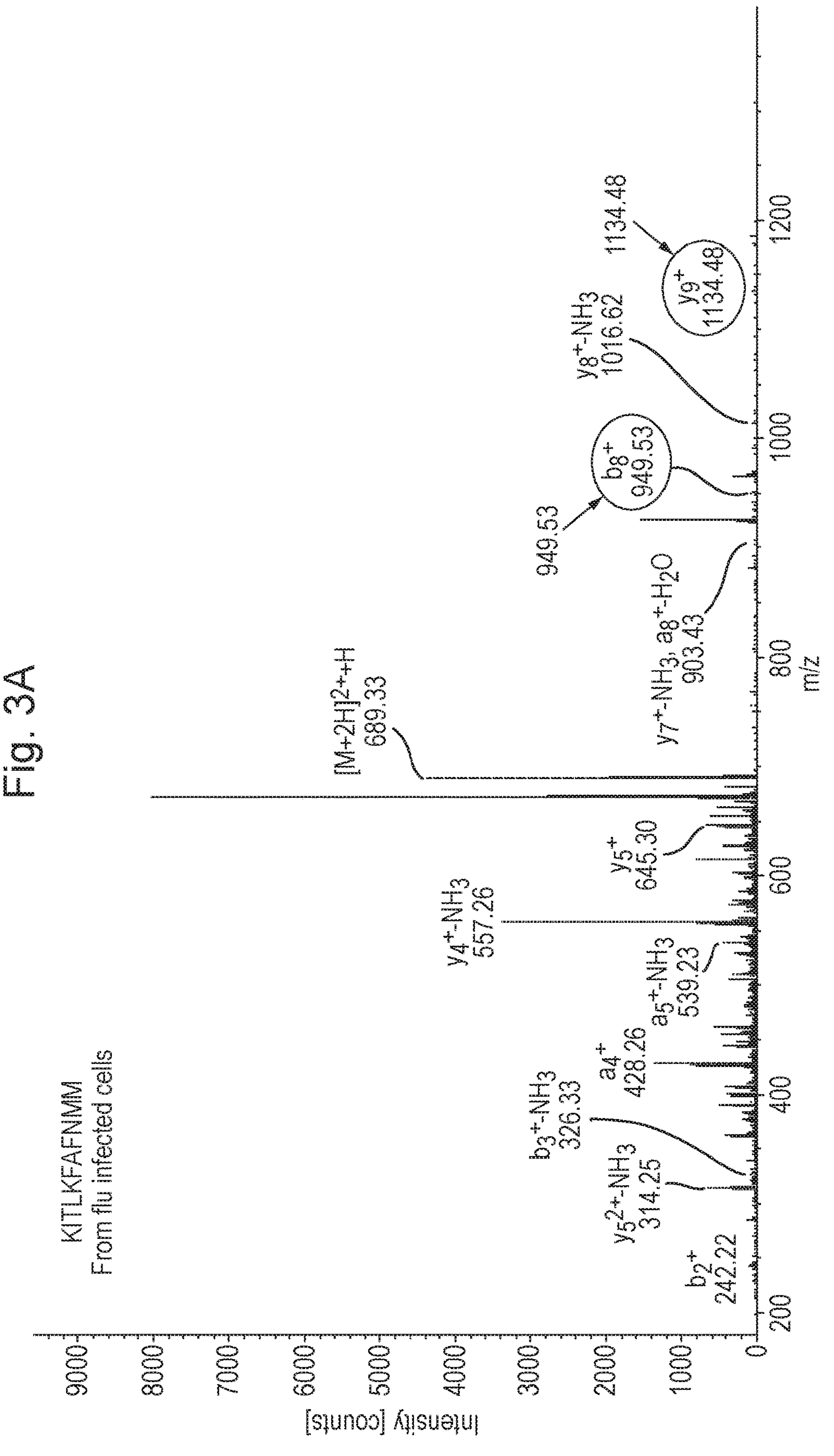
FIG. 3: Comparison of mass spectra of KITLKFAFNMM from influenza virus A infected cells (A) and synthetic KITLKFAFNMM peptide (B). Some typical ions in each spectrum are circled to emphasise the identity of the peptide from infected cells with that synthesised.
Figure 3B:
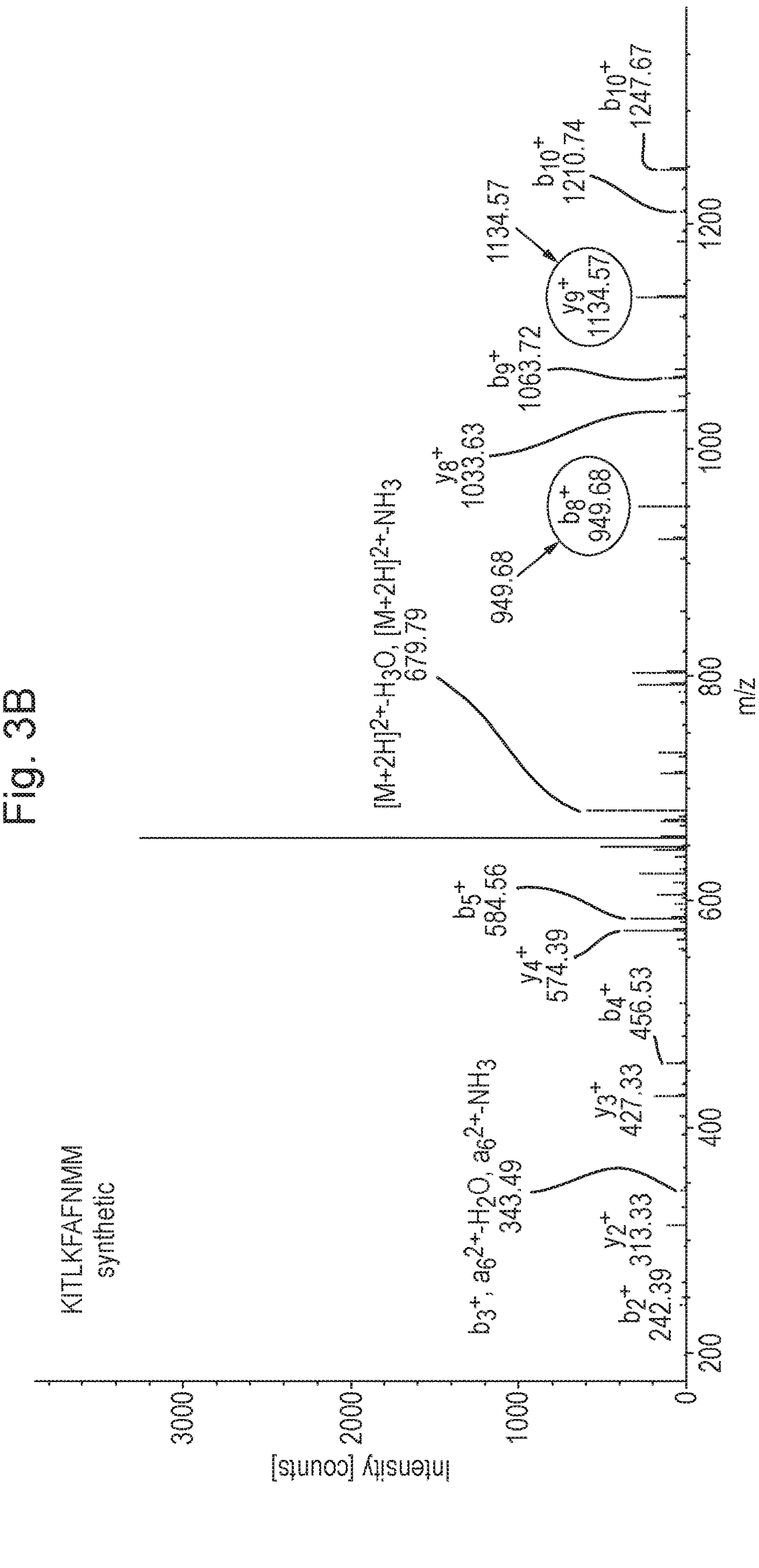
Figure 4:
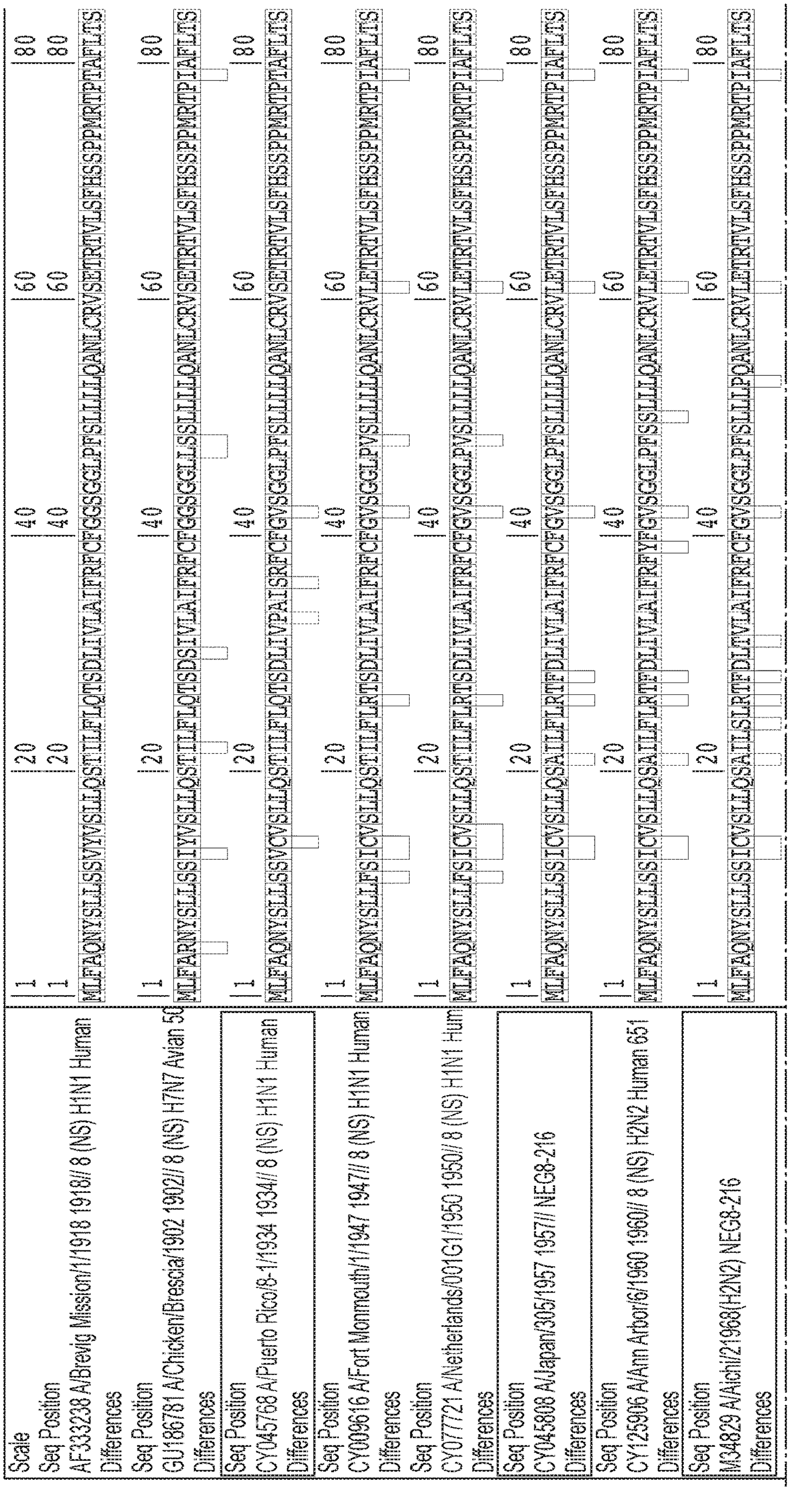
FIG. 4: Alignment of NEG8 polypeptide sequences of SEQ ID NOs: 1 and 3 to 15.

FIG. 1 to 3 compare the mass spectra obtained for synthetic peptides with those obtained for peptides isolated from infected cells. Some typical ions are circled in each spectrum to illustrate the identity of the peptides isolated from infected cells with its synthetic analog. The data confirm that the peptides IAPSSVKALS, LMQRGPSTF and KITLKFAFNMM encoded by the NEG8 ORF are truly found in influenza A virus-infected cells.

Example 3

The sequence of the polypeptide encoded by the NEG8 ORF

```
(SEQ ID NO: 2; MLFVQSYFPLFLVCVSLLQSAILSLQTFDLAVLA

IFRFCFGVSGGPPFSLLLLQANLCRFLETRTVLSFHSSPPMRTPIAFLT
```

-continued

```
SSIVCPGKEGNGEISPTIAPSSVKALSNTMVSSRSKITLKFAFNMMFFS

MIAWSILMQRGPSTFCLGISMNQFLDNSSIVMSVMYREAGVETMVILSA

SSDSSFRIFSTICFPTWVAALMSRPRVLPLPLRDL)
```

was used to search datasets of T cell epitopes derived from influenza virus infected cells. The NEG8 peptides described in Examples 1 and 2 were also identified using this search. The purpose of performing the search was to establish whether any NEG8 peptides or sequences within the polypeptide encoded by the NEG8 ORF are shared with any other influenza A virus proteins. Table 5 sets out T cell epitopes derived from influenza A virus proteins other than NEG8 that are also comprised in one or more of the NEG8 peptides identified in Examples 1 and 2 or the polypeptide encoded by the NEG8 ORF. From this, numerous NEG8 peptides considered to bind to MHC in cells infected with influenza A virus can be identified based on confidence level, XCorr, and performance of fragment mass spectra.

TABLE 5

NEG8 peptides shared with other flu proteins

| Seq. | Protein | Motif | Flu strain | Xcorr | m/z | HLA binding | Notes |
|---|---|---|---|---|---|---|---|
| AFNMMFLSM | NSP | A24 | H2N2 H3N2 (human) | 1.35 | 554.24 | A2:10 A24:7 | Multiple dataset |
| AILSLQTFD | NSP | A24 | H3N2 (human) | 1.10 | 504.26 | | Multiple dataset |
| DNSSIVISV | NSP | | H3N2 (human) | 1.40 | 467.24 | | Multiple dataset |
| IAWSILIQ | NS1 | | H1N1 (human) H7N7 (avian) H2N2 (human) | 1.22 | 472.28 | | Multiple dataset |
| IVMSVMYR | NSP | A3 | H3N2 (human) | 1.17 | 507.75 | | Multiple dataset |
| FLICVSPLQL | NSP | A2/24 | H3N2 (human) | 1.76 | 566.81 | A2:24 A24:13 | VLS0670 |
| GGLPFSLLL | NS1 | | H1N1 (human) | 1.82 | 458.78 | | VLS0670 |
| LFLICVSLL | NSP | A24 | H3N2 (human) | 1.74 | 510.81 | A2:18 A24:21 | VLS0670 |
| SPLQLAILSL | NSP | B7 | H3N2 (human) | 1.90 | 527.82 | B7:22 | VLS0670 |
| WSILMQRGP | NSP | | H3N2 (human) | 2.14 | 544.29 | | VLS0670 |
| IFRFCFGGSG | Polymerase PB2 | | H7N7 (avian) H1N1 (human) | 1.49 | 545.76 | | VLS3056 |

TABLE 5-continued

NEG8 peptides shared with other flu proteins

| Seq. | Protein | Motif | Flu strain | Xcorr | m/z | HLA binding | Notes |
|---|---|---|---|---|---|---|---|
| VAASMFRP | NSP | | H3N2 (human) | 1.45 | 447.74 | | VLS3056 |
| LSLQTSDLA | NSP | | H3N2 (human) | 1.11 | 474.25 | | VLS3056 |
| SIRVSNRS | Polymerase PB2 | | H7N7 (avian) | 1.08 | 459.76 | | VLS3056 |
| FSVMFLSM | NS1 | | H7N7 (avian) | 1.17 | 489.22 | | VLS3056 VLS3063 |
| SVKALSSI | HA | A2/24 | H7N7 (avian) H1N1 (human) | 1.15 | 402.74 | | VLS3056 VLS3063 |
| ALMSRPRV | NSP | A2 | H3N2 (human) | 1.24 | 465.27 | | VLS3056 |
| EGNGEISPT | NSP | | H3N2 H2N2 H1N1 (human) | 1.02 | 452.21 | | VLS3056 |
| AFNMMFFS | NSP | | H3N2 (human) | 1.06 | 505.69 | | VLS3056 |
| PAISRFCF | HA | A24 | H1N1 (human) | 1.48 | 470.73 | | VLS3056 |
| AFSVMFLSM | NSP | A24 | H7N7 (avian) | 1.36 | 516.74 | A24:7 | VLS3056 |
| LIQRGPATFCL | Matrix protein | A2/24 | H2N2 H1N1 (human) | 1.36 | 609.83 | | VLS3063 |
| AILSLQTFD | NSP | A24 | H3N2 (human) | 1.10 | 504.26 | A24:2 | VLS3063 |
| ALSSIRVSS | Polymerase PB2 | A2 B7 | H1N1 (human) | 1.10 | 460.25 | A2:16 B7:7 | VLS3063 |
| FSMMLLSMI | Polymerase PB1 | | H1N1 (human) | 1.00 | 560.76 | | VLS3063 |
| SPPMRTPT | PA-X protein | | H1N1 (human) | 1.13 | 451.72 | | VLS3063 |
| LIVLAIYRFC | NSP | A24 | H3N2 (human) | 1.11 | 605.86 | | VLS3063 |
| SLRTFDLA | NSP | A2 | H3N2 (human) | 1.09 | 461.74 | | VLS3063 |
| MLFVQSYFQ | NSP | | H3N2 (human) | 1.05 | 581.79 | | VLS3063 |

Example 4

Stimulation of CTL Responses In Vitro

Peripheral blood mononuclear cells (PBMCs) from a healthy (naive) human donor are stimulated with peptides encoded by the NEG8 ORF and shown to bind to MHC class I in influenza A virus-infected cells, (in a cytokine cocktail to induce an antigen specific CTL response. The PBMCs are stimulated with pooled free peptides (FPs) for a total of four stimulations at varying peptide loads.

These stimulated PBMCs are then assayed by co-culturing with uninfected, infected, or peptide loaded targets for antigen specific response. TAP-deficient cells (T2) are used for peptide loading, and blank T2 cells are used as a control. Activated PBMCs are assayed for both interferon gamma (IFNγ) and CD107a degranulation markers by flow cytometry.

Dextramer Studies

Dextramer reagents are fluorescently labelled and are used to detect antigen specific T-cells in cell suspensions and solid tissue samples. MHC dextramers are added to PBMCs or splenocytes. An optimal amount of anti-CD8 antibody conjugated with a relevant fluorochrome is then added. Additional antibodies (e.g. anti-CD3 or anti-CD4 antibodies) conjugated with other relevant fluorochromes may also be added at this step. Cells are then analysed using a flow cytometer.

In Vivo CTL Studies

Transgenic mice (5-6 mice per group) are immunised with free synthetic peptide or nanoparticle-peptide conjugates mixed with and without montanide-51 adjuvant three times at 2-week intervals by subcutaneous and intra-dermal routes of administration. Spleen and draining lymph nodes are collected 7 days after the final boost for CTL analysis. Single cell suspensions are prepared from the lymphoid organs and cells are stimulated with peptide antigens in culture for 7 days. The reactivated T-cells are assayed for epitope specific CTL responses using NEG8 peptide-loaded T2 cells and influenza A virus-infected HepG2 cells as targets in the following assays: production of IFN-γ and granzyme-B by ELISpot; cytokine secretion by MAGPIX assay; CD107a co-expression by flow cytometry.

Adoptive Transfer Experiments

Adoptive transfer experiments are performed to investigate whether peptide-specific CTL generated in transgenic mice have cytotoxic effect against influenza A virus infected cells in vivo in SCID-Beige mice. Infected liver tumour suspension is injected sc or iv into SCID Beige mice, followed by single or multiple adoptive transfer of peptide specific CTL generated in transgenic A2 mice against peptide or peptide-nanoparticle constructs. Appropriate controls are used. Survival of mice is monitored.

Example 5

Changes in Predominant ORF Length Over Time

The international flu database was used to obtain the sequence of segment 8 for numerous human influenza A viruses. The negative sense genomic sequence was analysed to determine the length of the NEG8 ORF in each virus. ORF length was calculated by determining the position of the first stop codon in the negative sense sequence. For example, a virus whose NEG8 sequence has a stop codon at position 94 has an ORF of 93 codons in length.

Figure 5:
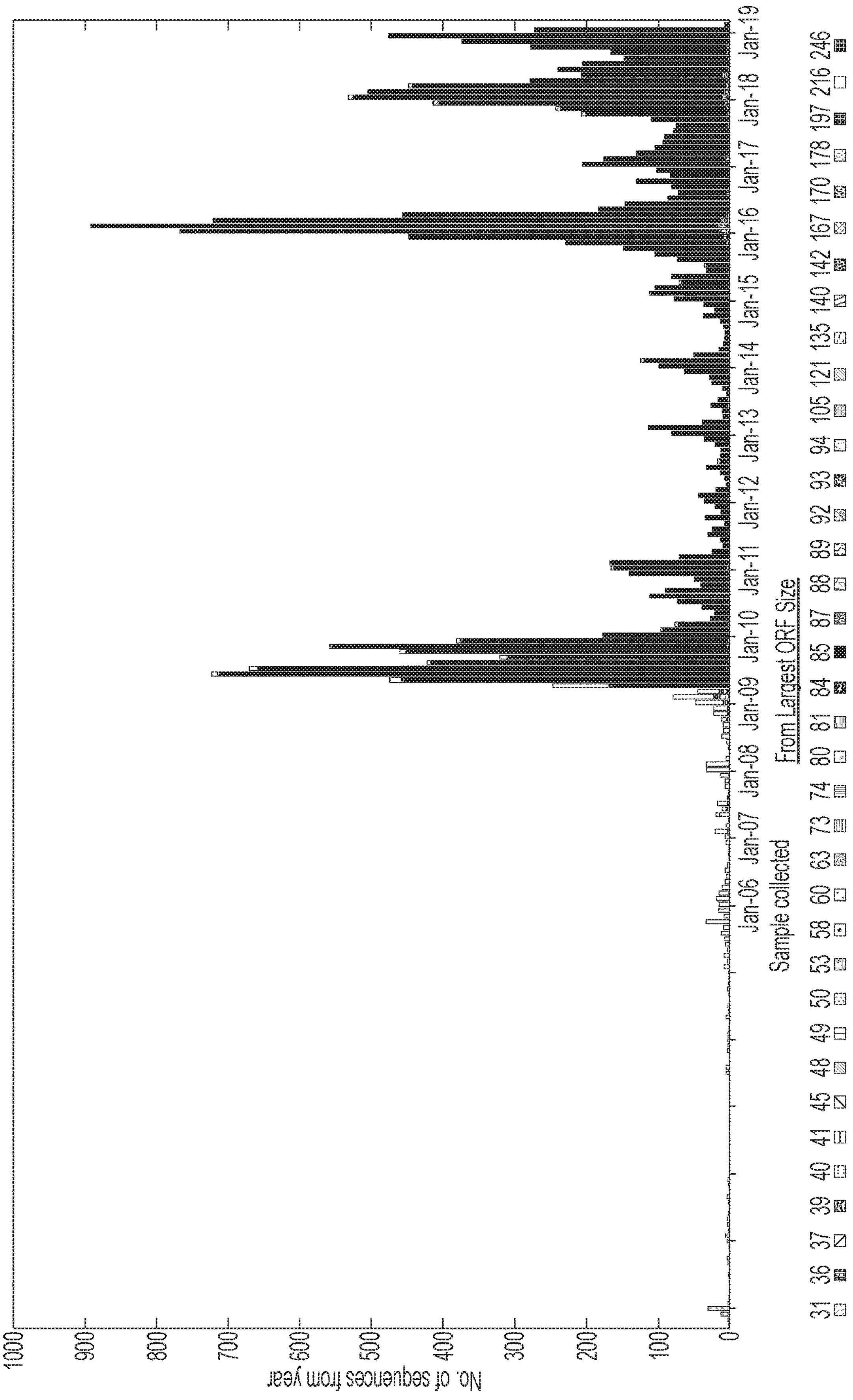
FIG. 5: ORF length by year. Chart shows number of collected influenza A viruses (Y axis) by year and month of collection (X axis). Colour coding indicates the length of the ORFs present in the viruses collected at each time point.

FIG. 5 shows the number of analysed influenza A viruses (Y axis) by year and month of collection (X axis). Colour coding indicates the length of the ORFs present in the viruses collected at each time point. The data shows that from 1918 to 1947 the predominant ORF length in human influenza A viruses was 167 codons. From 1947 to 2009, a 216 codon ORF was predominant. Since the 2009 pandemic flu, the predominant ORF was 85 codons in length.

ORF Length by Serotype

Figure 6:
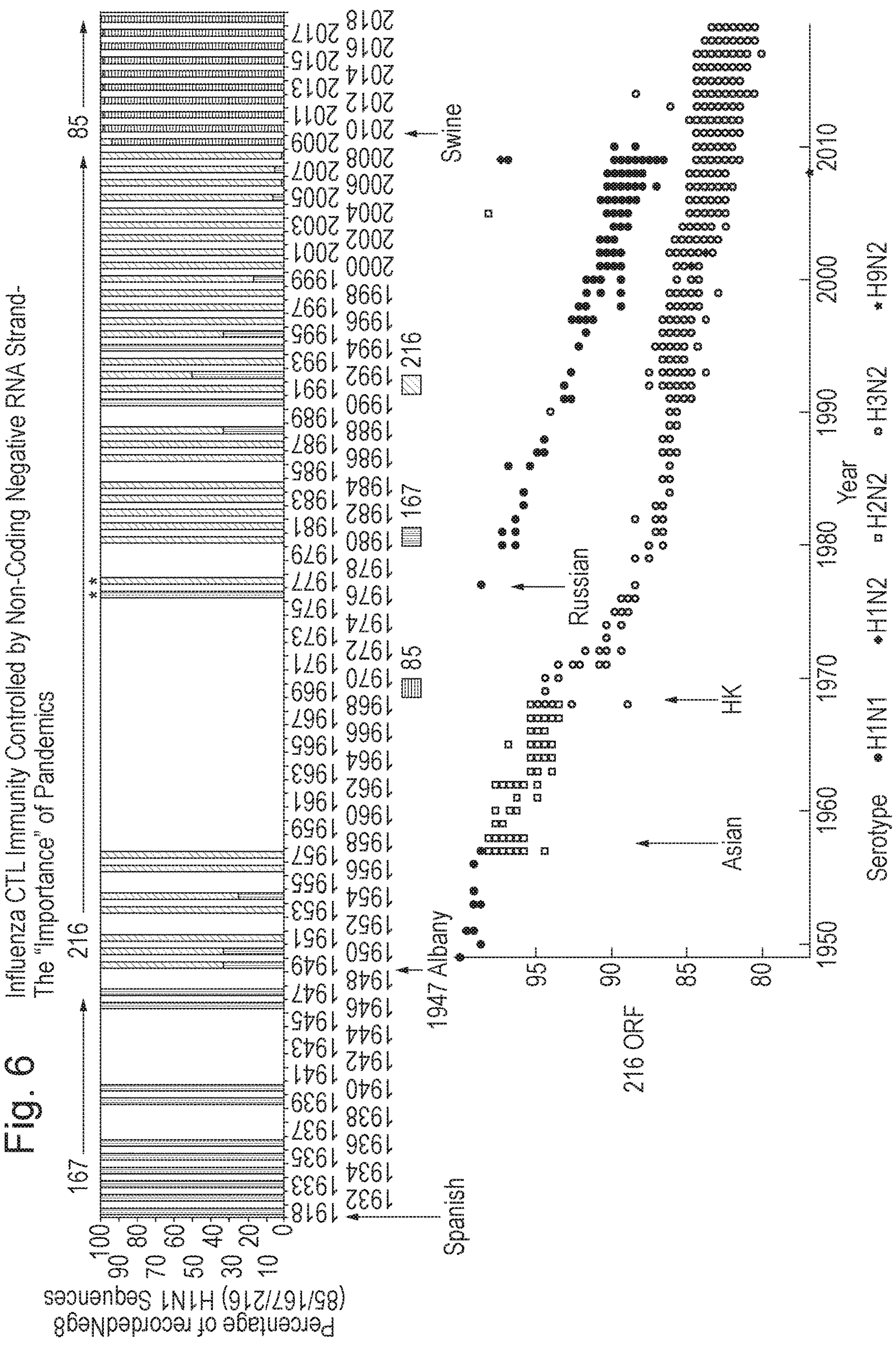
FIG. 6: ORF identity by year. Colour coding shows the serotype of each plotted virus.
Figure 7:
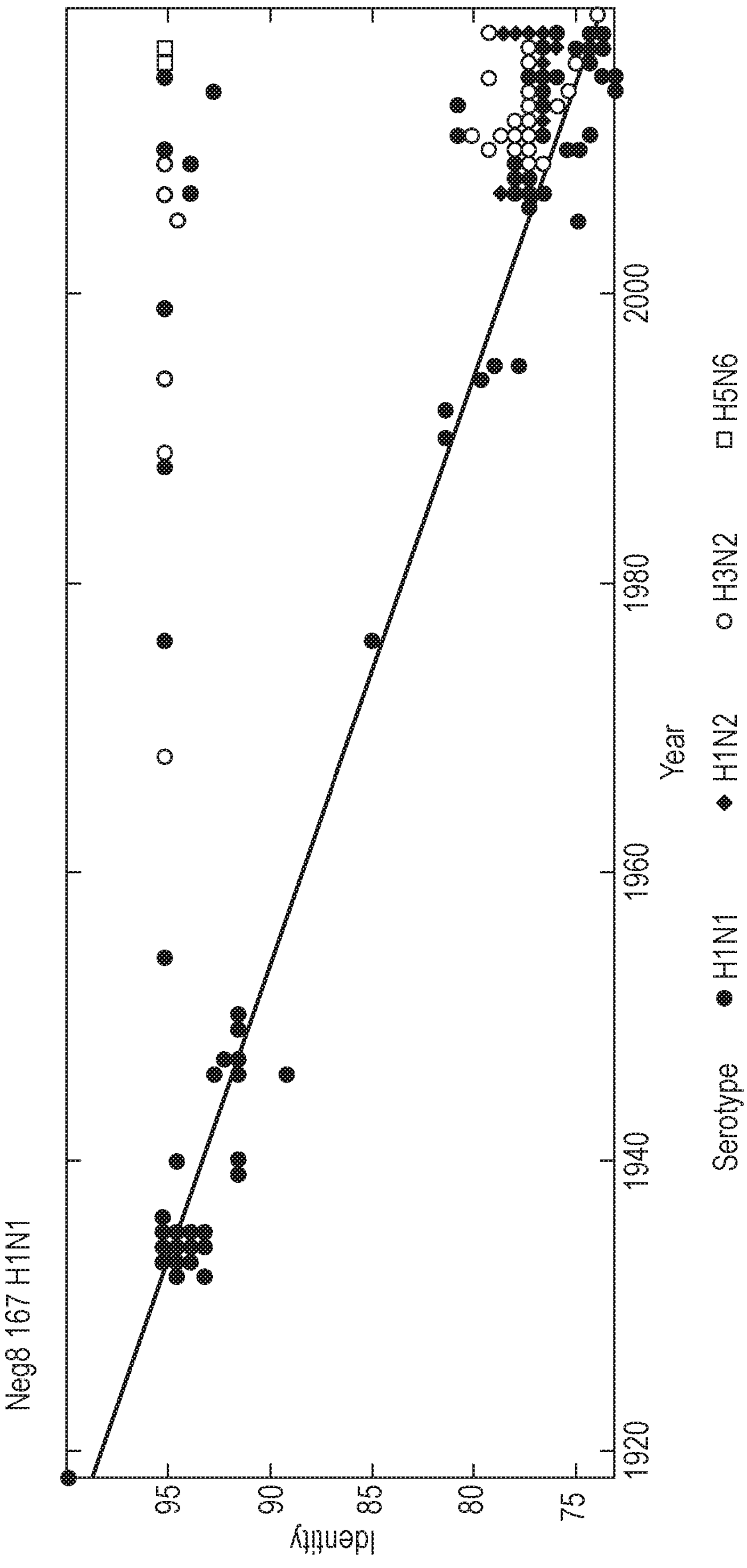
FIG. 7: ORF identity by year. Colour coding shows the serotype of each plotted virus.

The relationship between serotype and ORF length was also considered. FIG. 6 shows ORF identity by year. The colour coding shows the serotype of each plotted virus. Between 1918 (Spanish flu—green) and 1957 (Asian flu—blue), the predominant 167 codon ORF was present in viruses of serotype H1N1. The predominant 167 codon ORF was then present in viruses of serotype H2N2 until 1968 (HK flu—yellow), at which point the predominant 167 codon ORF became present in viruses of serotype H3N2. The 167 codon ORF was seen again in H1N1 serotype viruses in 1976 as Russian flu (green). Results are confirmed in FIG. 7 which plots identity of the 167 codon ORF by year, with serotype shown in colour coding, These data show that ORF length may be maintained in the influenza A virus population despite changes in serotype and associated constellation effects.

ORF Length by Species

Figure 8:
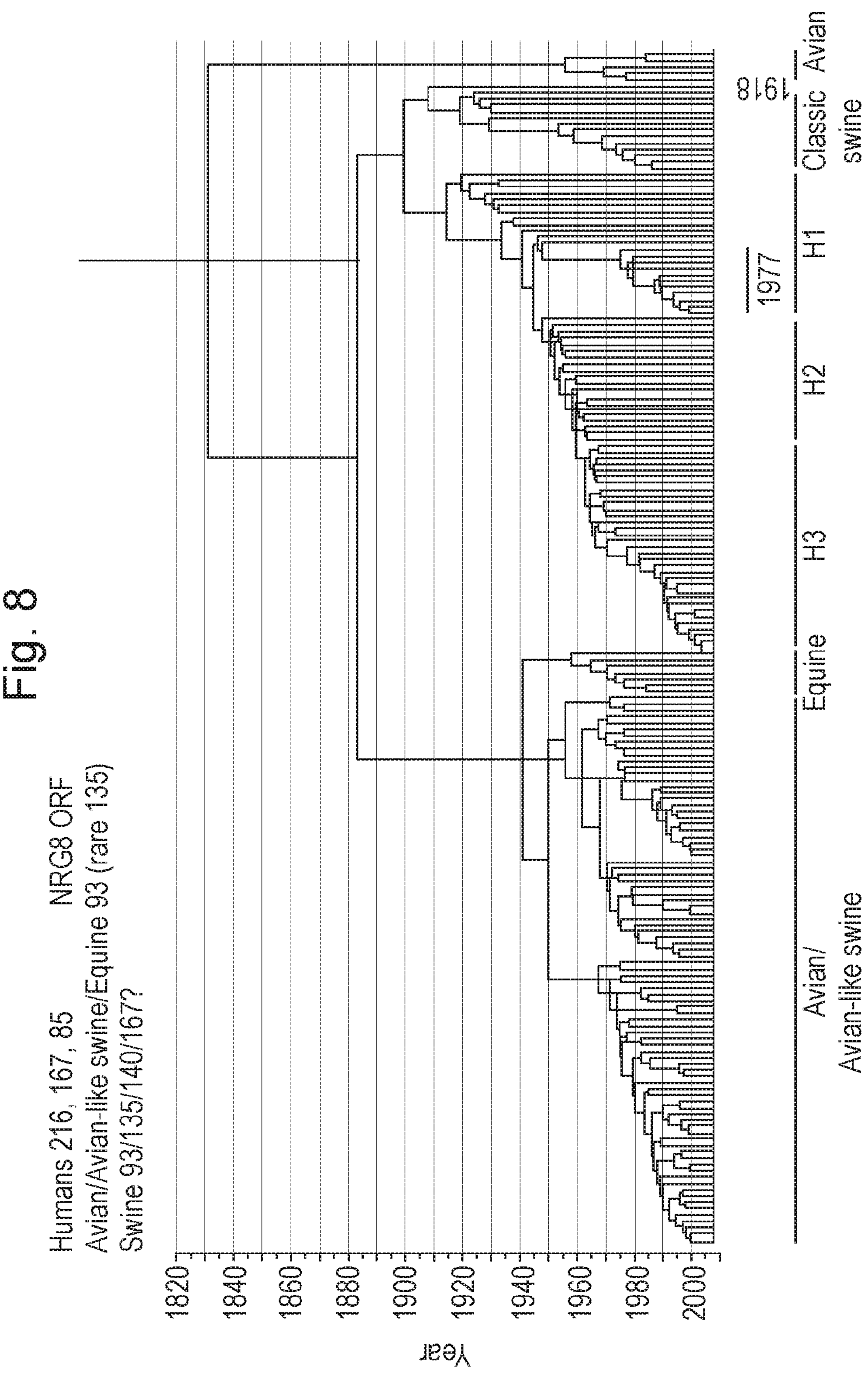
FIG. 8: ORF lengths prevalent in different species of influenza A virus.

FIG. 8 shows ORF lengths prevalent in different species of influenza A virus. A 93 codon ORF (or more rarely, a 135 codon ORF) has been observed in avian, avian-like swine, and equine influenza A viruses. A 140 codon ORF and a 167 codon ORF have been observed in swine influenza A viruses. In equine influenza A viruses, the NEG8 ORF is 93 codons in length almost 100% of the time. Equine influenza A viruses never contain the human-length ORFs of 85,167 or 216 codons in length.

The invention claimed is:

1. A vaccine composition comprising an immunogenic peptide comprising an influenza A CD8+ T cell epitope, wherein the CD8+ T cell epitope is selected from any one of SEQ ID NOs: 16 to 18 and 20 to 53, or a variant thereof having at least 80% identity to any one of SEQ ID NOs: 16 to 18 and 20 to 53, said variant comprising an epitope that is recognized by a CD8+ T cell, and wherein the immunogenic peptide:

(i) is about 8 to about 30 amino acids in length; and (ii) is attached to a nanoparticle.

2. The vaccine composition of claim 1, which comprises two or more immunogenic peptides, each comprising a different influenza A CD8+ T cell epitope selected from SEQ ID NOs: 16 to 18 and 20 to 53, or a variant thereof having at least 80% identity to one of SEQ ID NOs: 16 to 18 and 20 to 53.

3. The vaccine composition of claim 1, which comprises at least one immunogenic peptide that interacts with at least two different HLA supertypes.

4. The vaccine composition of claim 1, wherein the CD8+ T cell epitope is conserved between human influenza A viruses.

5. The vaccine composition of claim 1, wherein the CD8+ T cell epitope is:

(a) conserved between human influenza A viruses and a swine, equine and/or avian influenza A virus, optionally wherein the swine influenza A virus is of serotype H1N1; and/or (b) present in a predicted ORF of at least 85, at least 167 or at least 216 codons in length in a swine, equine and/or avian influenza A virus.

6. The vaccine composition of claim 1, wherein the CD8+ T cell epitope comprises the amino acid sequence of any one of SEQ ID NOs: 16 to 18 and 20 to 53.

7. A method preventing or treating an influenza infection, comprising administering a vaccine composition to an individual infected with, or at risk of being infected with, an influenza A virus, wherein said vaccine composition comprises: an immunogenic peptide comprising an influenza A CD8+ T cell epitope, wherein the CD8+ T cell epitope is selected from any one of SEQ ID NOs: 16 to 18 and 20 to 53, or a variant thereof having at least 80% identity to any one of SEQ ID NOs: 16 to 18 and 20 to 53, said variant comprising an epitope that is recognized by a CD8+ T cell, and wherein the immunogenic peptide:

(i) is about 8 to about 30 amino acids in length; and (ii) is attached to a nanoparticle, and wherein the nanoparticle is coated with a coating that includes N-acetylglucosamine (GlcNAc).

8. The method of claim 7, wherein:

(a) the influenza infection is caused by a zoonotic influenza virus;

(b) the individual is human; and/or (c) the influenza infection is a pandemic influenza infection.

9. The vaccine composition of claim 5, wherein the swine influenza A virus is of serotype H1N1.

10. The vaccine composition of claim 1, wherein the CD8+ T cell epitope is selected from any one of SEQ ID NOs: 16, 17, 20 to 22, 26 to 30 or 32 to 53, or a variant thereof having at least 80% identity to any one of SEQ ID NOs: 16, 17, 20 to 22, 26 to 30 or 32 to 53, said variant comprising an epitope that is recognized by a CD8+ T cell.

11. The vaccine composition of claim 10, wherein the CD8+ T cell epitope is selected from any one of SEQ ID NOs: 16, 17, 20 to 22, 26 to 30 or 32 to 53.

12. The vaccine composition of claim 1, wherein the nanoparticle is a gold nanoparticle, a calcium phosphate nanoparticle, or a silicon nanoparticle.

13. The vaccine composition of claim 12, wherein the nanoparticle is a gold nanoparticle.

14. The vaccine composition of claim 1, wherein the nanoparticle is coated with glucose, N-acetylglucosamine (GlcNAc), glutathione and/or 2-thioethyl-D-glucopyranoside.

15. The vaccine composition of claim 13, wherein the gold nanoparticle is coated with alpha-galactose and/or beta-GlcNAc.

16. The vaccine composition of claim 1, wherein the immunogenic peptide is attached to the nanoparticle via a linker.

17. The vaccine composition of claim 16, wherein the linker comprises a peptide portion with the amino acid sequence AAY.

18. The vaccine composition of claim 17, wherein the linker has the structure —S—$(CH_2)_2$-CONH-AAY-, wherein the AAY sequence is linked to the N-terminus of the immunogenic peptide, and the S atom is attached to the nanoparticle.

19. The vaccine composition of claim 1, wherein the immunogenic peptide consists of the CD8+ T cell epitope of any one of SEQ ID NOs: 16 to 18 and 20 to 53, or variant thereof having at least 80% identity to any one of SEQ ID NOs: 16 to 18 and 20 to 53, said variant comprising an epitope that is recognized by a CD8+ T cell.

20. The vaccine composition of claim 19, wherein the immunogenic peptide is attached to the nanoparticle via a linker, and the linker comprises a peptide portion which is attached to the immunogenic peptide.

21. A method of inducing an immune response in an individual, comprising administering to the individual an immunogenic peptide comprising an influenza A CD8+ T cell epitope selected from the group consisting of any one of SEQ ID NOs: 16 to 18 and 20 to 53, or a variant thereof having at least 80% identity to any one of SEQ ID NOs: 16 to 18 and 20 to 53, said variant comprising an epitope that is recognized by a CD8+ T cell, wherein the peptide is about 8 to about 30 amino acids in length and is attached to a nanoparticle and wherein the nanoparticle is coated with a coating that includes N-acetylglucosamine (GlcNAc).

* * * * *

SEQUENCE LISTING

```
<160> NUMBER OF SEQ ID NOS: 58

<210> SEQ ID NO 1
<211> LENGTH: 167
<212> TYPE: PRT
<213> ORGANISM: Influenza A virus

<400> SEQUENCE: 1

Met Leu Phe Ala Gln Asn Tyr Ser Leu Leu Ser Ser Val Tyr Val Ser
1               5                   10                  15

Leu Leu Gln Ser Thr Ile Leu Phe Leu Gln Thr Ser Asp Leu Ile Val
            20                  25                  30

Leu Ala Ile Phe Arg Phe Cys Phe Gly Gly Ser Gly Gly Leu Pro Phe
        35                  40                  45

Ser Leu Leu Leu Leu Gln Ala Asn Leu Cys Arg Val Ser Glu Thr Arg
    50                  55                  60

Thr Val Leu Ser Phe His Ser Ser Pro Pro Met Arg Thr Pro Thr Ala
65                  70                  75                  80

Phe Leu Thr Ser Ser Ser Val Cys Pro Gly Arg Glu Gly Asn Gly Glu
                85                  90                  95

Ile Ser Pro Thr Ile Ala Pro Ser Ser Val Lys Ala Leu Ser Ser Ile
            100                 105                 110

Arg Val Ser Ser Arg Ser Lys Ile Thr Leu Lys Phe Ala Phe Ser Met
        115                 120                 125

Met Phe Leu Ser Met Ile Ala Trp Ser Ile Leu Ile Gln Arg Glu Pro
    130                 135                 140

Ala Thr Phe Cys Leu Gly Met Ser Met Asn Gln Ser Leu Asp Ile Ser
145                 150                 155                 160

Ser Arg Val Met Ser Val Arg
                165


<210> SEQ ID NO 2
<211> LENGTH: 216
<212> TYPE: PRT
<213> ORGANISM: Influenza A virus
```

<400> SEQUENCE: 2

```
Met Leu Phe Val Gln Ser Tyr Phe Pro Leu Phe Leu Val Cys Val Ser
1               5                   10                  15

Leu Leu Gln Ser Ala Ile Leu Ser Leu Gln Thr Phe Asp Leu Ala Val
            20                  25                  30

Leu Ala Ile Phe Arg Phe Cys Phe Gly Val Ser Gly Gly Pro Pro Phe
        35                  40                  45

Ser Leu Leu Leu Leu Gln Ala Asn Leu Cys Arg Phe Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Ile Val Cys Pro Gly Lys Glu Gly Asn Gly Glu
                85                  90                  95

Ile Ser Pro Thr Ile Ala Pro Ser Ser Val Lys Ala Leu Ser Asn Thr
            100                 105                 110

Met Val Ser Ser Arg Ser Lys Ile Thr Leu Lys Phe Ala Phe Asn Met
        115                 120                 125

Met Phe Phe Ser Met Ile Ala Trp Ser Ile Leu Met Gln Arg Gly Pro
    130                 135                 140

Ser Thr Phe Cys Leu Gly Ile Ser Met Asn Gln Phe Leu Asp Asn Ser
145                 150                 155                 160

Ser Ile Val Met Ser Val Met Tyr Arg Glu Ala Gly Val Glu Thr Met
                165                 170                 175

Val Ile Leu Ser Ala Ser Ser Asp Ser Ser Phe Arg Ile Phe Ser Thr
            180                 185                 190

Ile Cys Phe Pro Thr Trp Val Ala Ala Leu Met Ser Arg Pro Arg Val
        195                 200                 205

Leu Pro Leu Pro Leu Arg Asp Leu
    210                 215
```

<210> SEQ ID NO 3
<211> LENGTH: 167
<212> TYPE: PRT
<213> ORGANISM: Influenza A virus

<400> SEQUENCE: 3

```
Met Leu Phe Ala Arg Asn Tyr Ser Leu Leu Ser Ser Ile Tyr Val Ser
1               5                   10                  15

Leu Leu Gln Ser Thr Thr Leu Phe Leu Gln Thr Ser Asp Ser Ile Val
            20                  25                  30

Leu Ala Ile Phe Arg Phe Cys Phe Gly Gly Ser Gly Gly Leu Leu Ser
        35                  40                  45

Ser Leu Leu Leu Leu Gln Ala Asn Leu Cys Arg Val Ser Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Ser Val Cys Pro Gly Arg Glu Gly Thr Gly Glu
                85                  90                  95

Ile Ser Pro Thr Ile Ala Pro Ser Ser Val Lys Ala Leu Ser Ser Ile
            100                 105                 110

Arg Val Ser Asn Arg Ser Lys Ile Ile Leu Lys Phe Ala Phe Ser Val
        115                 120                 125

Met Phe Leu Ser Met Ile Ala Trp Ser Ile Leu Ile Gln Arg Glu Pro
    130                 135                 140
```

```
Ala Thr Phe Cys Leu Gly Met Ser Met Asn Gln Ser Leu Asp Ile Ser
145                 150                 155                 160

Ser Arg Val Met Ser Val Arg
                165


<210> SEQ ID NO 4
<211> LENGTH: 167
<212> TYPE: PRT
<213> ORGANISM: Influenza A virus

<400> SEQUENCE: 4

Met Leu Phe Ala Gln Asn Tyr Ser Leu Leu Ser Ser Val Cys Val Ser
1               5                   10                  15

Leu Leu Gln Ser Thr Ile Leu Phe Leu Gln Thr Ser Asp Leu Ile Val
            20                  25                  30

Pro Ala Ile Ser Arg Phe Cys Phe Gly Val Ser Cys Gly Leu Pro Phe
        35                  40                  45

Ser Leu Leu Leu Leu Gln Ala Asn Leu Cys Arg Val Ser Glu Thr Arg
    50                  55                  60

Thr Val Leu Ser Phe His Ser Ser Pro Pro Met Arg Thr Pro Thr Ala
65                  70                  75                  80

Phe Leu Thr Ser Ser Ala Val Cys Pro Gly Arg Glu Gly Asn Gly Glu
                85                  90                  95

Ile Ser Pro Thr Ile Ala Pro Ser Ser Val Lys Ala Leu Ser Asn Ile
            100                 105                 110

Arg Val Ser Ser Arg Ser Lys Ile Thr Leu Lys Phe Ala Phe Ser Met
        115                 120                 125

Met Phe Leu Ser Met Ile Ala Trp Ser Ile Leu Ile Gln Arg Gly Pro
    130                 135                 140

Ala Thr Phe Cys Leu Gly Met Ser Met Asp Gln Ser Leu Asp Ile Ser
145                 150                 155                 160

Ser Arg Val Met Ser Val Arg
                165


<210> SEQ ID NO 5
<211> LENGTH: 167
<212> TYPE: PRT
<213> ORGANISM: Influenza A virus

<400> SEQUENCE: 5

Met Leu Phe Ala Gln Asn Tyr Ser Leu Leu Phe Ser Ile Cys Val Ser
1               5                   10                  15

Leu Leu Gln Ser Thr Ile Leu Phe Leu Arg Thr Ser Asp Leu Ile Val
            20                  25                  30

Leu Ala Ile Phe Arg Phe Cys Phe Gly Val Ser Gly Gly Leu Pro Val
        35                  40                  45

Ser Leu Leu Leu Leu Gln Ala Asn Leu Cys Arg Val Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Leu Val Cys Pro Gly Arg Glu Gly Asn Gly Glu
                85                  90                  95

Ile Ser Pro Thr Ile Ala Pro Ser Ser Val Lys Ala Leu Ser Asn Ile
            100                 105                 110

Arg Val Ser Ser Arg Ser Lys Ile Thr Leu Lys Phe Ala Phe Ser Met
        115                 120                 125
```

```
Met Leu Leu Ser Met Ile Ala Trp Ser Ile Leu Ile Gln Arg Gly Pro
    130                 135                 140

Ala Thr Phe Cys Leu Gly Met Ser Met Asn Gln Ser Leu Asp Ile Ser
145                 150                 155                 160

Ser Ile Val Met Ser Val Arg
                165


<210> SEQ ID NO 6
<211> LENGTH: 167
<212> TYPE: PRT
<213> ORGANISM: Influenza A virus

<400> SEQUENCE: 6

Met Leu Phe Ala Gln Asn Tyr Ser Leu Leu Phe Ser Ile Cys Ala Ser
1               5                   10                  15

Leu Leu Gln Ser Thr Ile Leu Phe Leu Arg Thr Ser Asp Leu Ile Val
            20                  25                  30

Leu Ala Ile Phe Arg Phe Cys Phe Gly Val Ser Gly Gly Leu Pro Val
        35                  40                  45

Ser Leu Leu Leu Leu Gln Ala Asn Leu Cys Arg Val Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Leu Val Cys Pro Gly Arg Glu Gly Asn Gly Glu
                85                  90                  95

Ile Ser Pro Tyr Ile Ala Pro Ser Ser Val Lys Ala Leu Ser Asn Ile
            100                 105                 110

Arg Val Ser Ser Arg Ser Lys Ile Thr Leu Lys Phe Ala Phe Ser Met
        115                 120                 125

Met Leu Leu Ser Met Ile Ala Trp Ser Ile Leu Ile Gln Arg Gly Pro
    130                 135                 140

Ala Thr Phe Cys Leu Gly Met Ser Met Asn Gln Ser Leu Asp Ile Ser
145                 150                 155                 160

Ser Ile Val Met Ser Val Arg
                165


<210> SEQ ID NO 7
<211> LENGTH: 216
<212> TYPE: PRT
<213> ORGANISM: Influenza A virus

<400> SEQUENCE: 7

Met Leu Phe Ala Gln Asn Tyr Ser Leu Leu Ser Ser Ile Cys Val Ser
1               5                   10                  15

Leu Leu Gln Ser Ala Ile Leu Phe Leu Arg Thr Phe Asp Leu Ile Val
            20                  25                  30

Leu Ala Ile Phe Arg Phe Cys Phe Gly Val Ser Gly Gly Leu Pro Phe
        35                  40                  45

Ser Leu Leu Leu Leu Gln Ala Asn Leu Cys Arg Val Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Leu Val Cys Pro Gly Arg Glu Gly Asn Gly Glu
                85                  90                  95

Ile Ser Pro Thr Ile Ala Pro Ser Ser Val Lys Ala Leu Ser Asn Ile
            100                 105                 110
```

-continued

```
Arg Val Ser Ser Arg Ser Lys Ile Thr Leu Lys Phe Ala Phe Asn Met
        115                 120                 125

Met Phe Leu Ser Met Ile Ala Trp Ser Ile Leu Ile Gln Arg Gly Pro
    130                 135                 140

Ala Thr Phe Cys Leu Gly Ile Ser Met Asn Gln Ser Leu Asp Ile Ser
145                 150                 155                 160

Ser Ile Val Met Ser Val Arg Tyr Arg Glu Ala Gly Ala Glu Ala Met
                165                 170                 175

Val Ile Leu Ser Ala Ser Ser Asp Ser Ser Phe Arg Ile Leu Ser Thr
            180                 185                 190

Ile Cys Phe Pro Thr Arg Val Ala Val Ser Met Phe Arg Pro Arg Val
        195                 200                 205

Leu Pro Leu Pro Leu Arg Asp Phe
    210                 215


<210> SEQ ID NO 8
<211> LENGTH: 216
<212> TYPE: PRT
<213> ORGANISM: Influenza A virus

<400> SEQUENCE: 8

Met Leu Phe Ala Gln Asn Tyr Ser Leu Leu Ser Ser Ile Cys Val Ser
1               5                   10                  15

Leu Leu Gln Ser Ala Ile Leu Phe Leu Arg Thr Phe Asp Leu Ile Val
            20                  25                  30

Leu Ala Ile Phe Arg Phe Tyr Phe Gly Val Ser Gly Gly Leu Pro Phe
        35                  40                  45

Ser Ser Leu Leu Leu Gln Ala Asn Leu Cys Arg Val Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Leu Val Cys Pro Gly Arg Glu Gly Asn Gly Glu
                85                  90                  95

Ile Ser Pro Thr Ile Ala Pro Ala Ser Val Lys Ala Leu Ser Asn Ile
            100                 105                 110

Arg Val Ser Ser Arg Ser Lys Ile Thr Leu Lys Phe Ala Phe Asn Met
        115                 120                 125

Met Phe Leu Ser Met Ile Ala Trp Ser Ile Leu Ile Gln Arg Gly Pro
    130                 135                 140

Ala Thr Phe Cys Leu Gly Ile Ser Met Asn Gln Ser Leu Asp Ile Ser
145                 150                 155                 160

Ser Ile Val Met Ser Asx Arg Tyr Arg Glu Ala Gly Ala Glu Ala Met
                165                 170                 175

Val Ile Leu Ser Ala Ser Ser Asp Ser Ser Phe Arg Ile Leu Ser Thr
            180                 185                 190

Ile Cys Phe Pro Thr Arg Val Ala Val Ser Met Phe Arg Pro Arg Val
        195                 200                 205

Leu Pro Leu Pro Leu Arg Asp Phe
    210                 215


<210> SEQ ID NO 9
<211> LENGTH: 216
<212> TYPE: PRT
<213> ORGANISM: Influenza A virus

<400> SEQUENCE: 9
```

```
Met Leu Phe Ala Gln Asn Tyr Ser Leu Leu Ser Ser Ile Cys Val Ser
1               5                   10                  15

Leu Leu Gln Ser Ala Ile Leu Ser Leu Arg Thr Phe Asp Leu Thr Val
            20                  25                  30

Leu Ala Ile Phe Arg Phe Cys Phe Gly Val Ser Gly Gly Leu Pro Phe
        35                  40                  45

Ser Leu Leu Leu Pro Gln Ala Asn Leu Cys Arg Val Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Ile Val Cys Pro Gly Arg Glu Gly Asn Gly Glu
                85                  90                  95

Ile Ser Pro Thr Ile Ala Pro Ser Ser Val Lys Ala Leu Ser Asn Ile
            100                 105                 110

Arg Val Ser Ser Arg Ser Lys Ile Thr Leu Lys Phe Ala Phe Asn Met
        115                 120                 125

Thr Phe Leu Ser Met Ile Ala Trp Ser Ile Leu Met Gln Arg Gly Pro
    130                 135                 140

Ser Thr Phe Cys Leu Gly Ile Ser Met Asn Gln Ser Leu Asp Asn Ser
145                 150                 155                 160

Ser Ile Val Met Ser Val Arg Tyr Arg Glu Ala Gly Ala Glu Ala Met
                165                 170                 175

Val Ile Leu Ser Ala Ser Ser Asp Ser Ser Phe Arg Ile Leu Ser Thr
            180                 185                 190

Ile Cys Phe Pro Thr Arg Val Ala Ala Ser Met Phe Arg Pro Arg Val
        195                 200                 205

Leu Pro Leu Pro Leu Arg Asp Phe
    210                 215


<210> SEQ ID NO 10
<211> LENGTH: 216
<212> TYPE: PRT
<213> ORGANISM: Influenza A virus

<400> SEQUENCE: 10

Met Leu Phe Ala Gln Asn Tyr Ser Leu Leu Ser Ser Ile Cys Val Ser
1               5                   10                  15

Leu Leu Gln Ser Ala Ile Leu Ser Leu Arg Thr Phe Asp Leu Ile Val
            20                  25                  30

Leu Ala Ile Tyr Arg Phe Cys Phe Gly Val Ser Gly Cys Leu Pro Phe
        35                  40                  45

Ser Leu Leu Leu Leu Gln Ala Asn Leu Cys Arg Phe Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Ile Val Cys Pro Gly Arg Glu Gly Asn Gly Glu
                85                  90                  95

Ile Ser Pro Thr Ile Ala Pro Ser Ser Val Lys Ala Leu Ser Asn Ile
            100                 105                 110

Arg Val Ser Ser Arg Ser Lys Ile Thr Leu Lys Phe Ala Phe Asn Met
        115                 120                 125

Met Phe Leu Ser Met Ile Ala Trp Ser Ile Leu Met Gln Arg Gly Pro
    130                 135                 140

Ser Thr Phe Cys Leu Gly Ile Ser Met Asn Gln Ser Leu Asp Asn Ser
145                 150                 155                 160
```

```
Ser Ile Val Met Ser Val Arg Tyr Arg Glu Ala Gly Ala Glu Ala Met
                165                 170                 175

Val Ile Leu Ser Ala Ser Ser Asp Phe Ser Phe Arg Ile Leu Ser Thr
            180                 185                 190

Ile Cys Phe Pro Thr Arg Val Ala Ala Ser Met Phe Arg Pro Arg Val
        195                 200                 205

Leu Pro Leu Pro Leu Arg Asp Phe
    210                 215


<210> SEQ ID NO 11
<211> LENGTH: 216
<212> TYPE: PRT
<213> ORGANISM: Influenza A virus

<400> SEQUENCE: 11

Met Leu Phe Ala Gln Asn Tyr Ser Gln Leu Phe Ser Val Cys Val Ser
1               5                   10                  15

Leu Leu Gln Ser Ala Ile Leu Ser Leu Arg Thr Phe Asp Leu Ala Val
            20                  25                  30

Leu Ala Ile Phe Arg Phe Cys Phe Gly Val Ser Gly Gly Pro Pro Phe
        35                  40                  45

Ser Leu Leu Leu Pro Gln Ala Asn Leu Cys Arg Val Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Ile Val Cys Pro Gly Lys Glu Gly Asn Gly Glu
                85                  90                  95

Ile Ser Pro Thr Ile Ala Pro Ser Ser Val Lys Ala Leu Ser Asn Thr
            100                 105                 110

Arg Val Ser Ser Arg Ser Lys Ile Thr Leu Lys Phe Ala Phe Asn Met
        115                 120                 125

Met Phe Phe Ser Met Ile Ala Trp Ser Ile Leu Met Gln Arg Gly Pro
    130                 135                 140

Ser Thr Phe Cys Leu Gly Ile Ser Met Asn Gln Phe Leu Asp Asn Ser
145                 150                 155                 160

Ser Ile Val Met Ser Val Met Tyr Arg Glu Ala Gly Val Glu Ala Met
                165                 170                 175

Val Ile Leu Ser Ala Ser Ser Asp Ser Ser Phe Arg Ile Phe Ser Thr
            180                 185                 190

Ile Cys Phe Pro Thr Trp Val Ala Ala Leu Met Ser Arg Pro Arg Val
        195                 200                 205

Leu Pro Leu Pro Leu Arg Asp Leu
    210                 215


<210> SEQ ID NO 12
<211> LENGTH: 216
<212> TYPE: PRT
<213> ORGANISM: Influenza A virus

<400> SEQUENCE: 12

Met Leu Phe Ala Gln Asn Tyr Ser Gln Leu Phe Leu Val Cys Val Ser
1               5                   10                  15

Leu Leu Gln Ser Ala Ile Leu Ser Leu Arg Thr Phe Asp Leu Ala Val
            20                  25                  30

Leu Ala Ile Phe Arg Phe Cys Phe Gly Val Ser Gly Gly Pro Pro Phe
        35                  40                  45
```

```
Ser Leu Leu Leu Pro Gln Ala Asn Leu Cys Arg Phe Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Ile Val Cys Pro Gly Lys Glu Gly Asn Gly Glu
                85                  90                  95

Ile Ser Pro Tyr Ile Ala Pro Ser Ser Val Lys Ala Leu Ser Asn Thr
            100                 105                 110

Arg Val Ser Ser Arg Ser Lys Ile Thr Leu Lys Phe Ala Phe Asn Met
        115                 120                 125

Met Phe Phe Ser Met Ile Ala Trp Ser Ile Leu Met Gln Arg Gly Pro
    130                 135                 140

Ser Thr Phe Cys Leu Gly Ile Ser Met Asn Gln Phe Leu Asp Asn Ser
145                 150                 155                 160

Ser Ile Val Ile Ser Val Met Tyr Arg Glu Ala Gly Val Glu Ala Met
                165                 170                 175

Val Ile Leu Ser Ala Ser Ser Asp Ser Ser Phe Arg Ile Phe Ser Thr
            180                 185                 190

Ile Cys Phe Pro Thr Trp Val Ala Ala Leu Met Ser Arg Pro Arg Val
        195                 200                 205

Leu Pro Leu Pro Leu Arg Asp Leu
    210                 215


<210> SEQ ID NO 13
<211> LENGTH: 216
<212> TYPE: PRT
<213> ORGANISM: Influenza A virus

<400> SEQUENCE: 13

Met Leu Phe Ala Gln Asn Tyr Ser Gln Leu Phe Leu Val Cys Val Ser
1               5                   10                  15

Leu Leu Gln Ser Ala Ile Leu Ser Leu Gln Thr Phe Asp Leu Ala Val
            20                  25                  30

Leu Ala Ile Phe Arg Phe Cys Phe Gly Val Ser Gly Gly Pro Pro Phe
        35                  40                  45

Ser Leu Leu Leu Leu Gln Ala Asn Leu Cys Arg Phe Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Ile Val Cys Pro Gly Lys Glu Gly Asn Gly Glu
                85                  90                  95

Ile Ser Pro Thr Ile Ala Pro Ser Ser Val Lys Ala Leu Ser Asn Thr
            100                 105                 110

Met Val Ser Ser Arg Ser Lys Thr Thr Leu Lys Phe Ala Phe Asn Met
        115                 120                 125

Met Phe Phe Ser Met Ile Ala Trp Ser Ile Leu Met Gln Arg Gly Pro
    130                 135                 140

Ser Thr Phe Cys Leu Gly Ile Ser Met Asn Gln Phe Leu Asp Asn Ser
145                 150                 155                 160

Ser Ile Val Met Ser Val Met Tyr Arg Glu Ala Gly Val Glu Ala Met
                165                 170                 175

Val Ile Leu Ser Ala Ser Ser Asp Ser Ser Phe Arg Ile Phe Ser Thr
            180                 185                 190

Ile Cys Phe Pro Thr Trp Val Ala Ala Leu Ile Ser Arg Pro Arg Val
```

```
        195                 200                 205

Leu Pro Leu Pro Leu Arg Asp Leu
    210                 215


<210> SEQ ID NO 14
<211> LENGTH: 216
<212> TYPE: PRT
<213> ORGANISM: Influenza A virus

<400> SEQUENCE: 14

Met Leu Phe Val Gln Ser Tyr Phe Gln Leu Phe Leu Ile Cys Val Ser
1               5                   10                  15

Leu Leu Gln Leu Ala Ile Leu Ser Leu Gln Thr Phe Asp Leu Ala Val
            20                  25                  30

Leu Ala Ile Ser Arg Phe Cys Phe Gly Val Ser Gly Gly Pro Pro Phe
        35                  40                  45

Ser Leu Leu Leu Leu Gln Ala Asn Leu Cys Arg Phe Leu Glu Thr Arg
    50                  55                  60

Thr Val Leu Ser Phe His Ser Ser Pro Pro Met Arg Thr Pro Ile Ala
65                  70                  75                  80

Phe Leu Thr Ser Ser Ile Val Cys Pro Gly Lys Glu Gly Asn Gly Glu
                85                  90                  95

Ile Ser Pro Thr Ile Ala Pro Ser Ser Val Lys Ala Leu Ser Asn Thr
            100                 105                 110

Ile Val Ser Ser Arg Ser Lys Ile Thr Leu Lys Phe Ala Phe Asn Val
        115                 120                 125

Met Phe Phe Ser Met Ile Ala Trp Ser Ile Leu Met Gln Arg Gly Pro
    130                 135                 140

Ser Thr Phe Cys Leu Gly Ile Ser Met Asn Gln Phe Leu Asp Asn Ser
145                 150                 155                 160

Ser Ile Val Met Ser Val Met Tyr Arg Glu Ala Gly Val Glu Thr Met
                165                 170                 175

Val Ile Leu Ser Ala Ser Ser Asp Ser Ser Phe Arg Ile Phe Ser Thr
            180                 185                 190

Ile Cys Phe Pro Thr Trp Val Ala Ala Leu Met Ser Arg Pro Arg Val
        195                 200                 205

Leu Pro Leu Pro Leu Arg Asp Leu
    210                 215


<210> SEQ ID NO 15
<211> LENGTH: 216
<212> TYPE: PRT
<213> ORGANISM: Influenza A virus

<400> SEQUENCE: 15

Met Leu Phe Val Gln Ser Tyr Phe Gln Leu Phe Leu Ile Cys Val Ser
1               5                   10                  15

Pro Leu Gln Leu Ala Ile Leu Ser Leu Gln Thr Ser Asp Leu Ala Val
            20                  25                  30

Leu Ala Ile Ser Arg Phe Cys Phe Gly Val Ser Gly Gly Pro Pro Phe
        35                  40                  45

Ser Leu Leu Leu Leu Gln Ala Asn Leu Cys Arg Phe Leu Glu Thr Arg
    50                  55                  60

Thr Val Leu Ser Phe His Ser Ser Pro Pro Met Arg Thr Pro Ile Ala
65                  70                  75                  80

Phe Leu Thr Ala Ser Ile Val Cys Pro Gly Lys Glu Gly Asn Gly Glu
```

-continued

```
                85                  90                  95

Ile Ser Pro Thr Ile Ala Pro Ser Ser Val Lys Ala Leu Ser Asn Thr
            100                 105                 110

Met Val Ser Ser Arg Pro Lys Ile Thr Leu Lys Phe Ala Phe Asn Met
        115                 120                 125

Ile Phe Phe Ser Met Ile Ala Trp Ser Ile Leu Met Gln Arg Gly Pro
    130                 135                 140

Ser Thr Phe Cys Leu Gly Ile Ser Met Asn Gln Phe Leu Asp Ser Ser
145                 150                 155                 160

Ser Ile Val Met Ser Val Met Tyr Arg Glu Ala Gly Val Glu Thr Met
                165                 170                 175

Val Ile Leu Ser Ala Ser Ser Asp Ser Ser Phe Arg Ile Phe Ser Ile
            180                 185                 190

Ile Cys Phe Pro Ala Trp Val Ala Ala Leu Val Ser Arg Pro Arg Val
        195                 200                 205

Leu Pro Leu Pro Leu Arg Asp Leu
    210                 215


<210> SEQ ID NO 16
<211> LENGTH: 9
<212> TYPE: PRT
<213> ORGANISM: Influenza A virus

<400> SEQUENCE: 16

Trp Ser Ile Leu Met Gln Arg Gly Pro
1               5


<210> SEQ ID NO 17
<211> LENGTH: 10
<212> TYPE: PRT
<213> ORGANISM: Influenza A virus

<400> SEQUENCE: 17

Glu Ala Gly Val Glu Thr Met Val Ile Leu
1               5                   10


<210> SEQ ID NO 18
<211> LENGTH: 10
<212> TYPE: PRT
<213> ORGANISM: Influenza A virus

<400> SEQUENCE: 18

Ile Ala Pro Ser Ser Val Lys Ala Leu Ser
1               5                   10


<210> SEQ ID NO 19
<211> LENGTH: 9
<212> TYPE: PRT
<213> ORGANISM: Influenza A virus

<400> SEQUENCE: 19

Pro Met Arg Thr Pro Ile Ala Phe Leu
1               5


<210> SEQ ID NO 20
<211> LENGTH: 10
<212> TYPE: PRT
<213> ORGANISM: Influenza A virus

<400> SEQUENCE: 20

Ile Ser Met Asn Gln Phe Leu Asp Asn Ser
```

1 5 10

<210> SEQ ID NO 21
<211> LENGTH: 9
<212> TYPE: PRT
<213> ORGANISM: Influenza A virus

<400> SEQUENCE: 21

Leu Met Gln Arg Gly Pro Ser Thr Phe
1 5

<210> SEQ ID NO 22
<211> LENGTH: 10
<212> TYPE: PRT
<213> ORGANISM: Influenza A virus

<400> SEQUENCE: 22

Phe His Ser Ser Pro Pro Met Arg Thr Pro
1 5 10

<210> SEQ ID NO 23
<211> LENGTH: 11
<212> TYPE: PRT
<213> ORGANISM: Influenza A virus

<400> SEQUENCE: 23

Lys Ile Thr Leu Lys Phe Ala Phe Asn Met Met
1 5 10

<210> SEQ ID NO 24
<211> LENGTH: 14
<212> TYPE: PRT
<213> ORGANISM: Influenza A virus

<400> SEQUENCE: 24

Leu Val Cys Val Ser Leu Leu Gln Ser Ala Ile Leu Ser Leu
1 5 10

<210> SEQ ID NO 25
<211> LENGTH: 9
<212> TYPE: PRT
<213> ORGANISM: Influenza A virus

<400> SEQUENCE: 25

Ala Phe Asn Met Met Phe Leu Ser Met
1 5

<210> SEQ ID NO 26
<211> LENGTH: 9
<212> TYPE: PRT
<213> ORGANISM: Influenza A virus

<400> SEQUENCE: 26

Ala Ile Leu Ser Leu Gln Thr Phe Asp
1 5

<210> SEQ ID NO 27
<211> LENGTH: 9
<212> TYPE: PRT
<213> ORGANISM: Influenza A virus

<400> SEQUENCE: 27

Asp Asn Ser Ser Ile Val Ile Ser Val
1 5

<210> SEQ ID NO 28
<211> LENGTH: 8
<212> TYPE: PRT
<213> ORGANISM: Influenza A virus

<400> SEQUENCE: 28

Ile Ala Trp Ser Ile Leu Ile Gln
1               5

<210> SEQ ID NO 29
<211> LENGTH: 8
<212> TYPE: PRT
<213> ORGANISM: Influenza A virus

<400> SEQUENCE: 29

Ile Val Met Ser Val Met Tyr Arg
1               5

<210> SEQ ID NO 30
<211> LENGTH: 10
<212> TYPE: PRT
<213> ORGANISM: Influenza A virus

<400> SEQUENCE: 30

Phe Leu Ile Cys Val Ser Pro Leu Gln Leu
1               5                   10

<210> SEQ ID NO 31
<211> LENGTH: 9
<212> TYPE: PRT
<213> ORGANISM: Influenza A virus

<400> SEQUENCE: 31

Gly Gly Leu Pro Phe Ser Leu Leu Leu
1               5

<210> SEQ ID NO 32
<211> LENGTH: 9
<212> TYPE: PRT
<213> ORGANISM: Influenza A virus

<400> SEQUENCE: 32

Leu Phe Leu Ile Cys Val Ser Leu Leu
1               5

<210> SEQ ID NO 33
<211> LENGTH: 10
<212> TYPE: PRT
<213> ORGANISM: Influenza A virus

<400> SEQUENCE: 33

Ser Pro Leu Gln Leu Ala Ile Leu Ser Leu
1               5                   10

<210> SEQ ID NO 34
<211> LENGTH: 10
<212> TYPE: PRT
<213> ORGANISM: Influenza A virus

<400> SEQUENCE: 34

Ile Phe Arg Phe Cys Phe Gly Gly Ser Gly
1               5                   10

<210> SEQ ID NO 35

<211> LENGTH: 8
<212> TYPE: PRT
<213> ORGANISM: Influenza A virus

<400> SEQUENCE: 35

Val Ala Ala Ser Met Phe Arg Pro
1 5

<210> SEQ ID NO 36
<211> LENGTH: 9
<212> TYPE: PRT
<213> ORGANISM: Influenza A virus

<400> SEQUENCE: 36

Leu Ser Leu Gln Thr Ser Asp Leu Ala
1 5

<210> SEQ ID NO 37
<211> LENGTH: 8
<212> TYPE: PRT
<213> ORGANISM: Influenza A virus

<400> SEQUENCE: 37

Ser Ile Arg Val Ser Asn Arg Ser
1 5

<210> SEQ ID NO 38
<211> LENGTH: 8
<212> TYPE: PRT
<213> ORGANISM: Influenza A virus

<400> SEQUENCE: 38

Phe Ser Val Met Phe Leu Ser Met
1 5

<210> SEQ ID NO 39
<211> LENGTH: 8
<212> TYPE: PRT
<213> ORGANISM: Influenza A virus

<400> SEQUENCE: 39

Ser Val Lys Ala Leu Ser Ser Ile
1 5

<210> SEQ ID NO 40
<211> LENGTH: 8
<212> TYPE: PRT
<213> ORGANISM: Influenza A virus

<400> SEQUENCE: 40

Ala Leu Met Ser Arg Pro Arg Val
1 5

<210> SEQ ID NO 41
<211> LENGTH: 9
<212> TYPE: PRT
<213> ORGANISM: Influenza A virus

<400> SEQUENCE: 41

Glu Gly Asn Gly Glu Ile Ser Pro Thr
1 5

<210> SEQ ID NO 42
<211> LENGTH: 8
<212> TYPE: PRT

<213> ORGANISM: Influenza A virus

<400> SEQUENCE: 42

Ala Phe Asn Met Met Phe Phe Ser
1 5

<210> SEQ ID NO 43
<211> LENGTH: 8
<212> TYPE: PRT
<213> ORGANISM: Influenza A virus

<400> SEQUENCE: 43

Pro Ala Ile Ser Arg Phe Cys Phe
1 5

<210> SEQ ID NO 44
<211> LENGTH: 9
<212> TYPE: PRT
<213> ORGANISM: Influenza A virus

<400> SEQUENCE: 44

Ala Phe Ser Val Met Phe Leu Ser Met
1 5

<210> SEQ ID NO 45
<211> LENGTH: 11
<212> TYPE: PRT
<213> ORGANISM: Influenza A virus

<400> SEQUENCE: 45

Leu Ile Gln Arg Gly Pro Ala Thr Phe Cys Leu
1 5 10

<210> SEQ ID NO 46
<211> LENGTH: 9
<212> TYPE: PRT
<213> ORGANISM: Influenza A virus

<400> SEQUENCE: 46

Leu Ile Gln Arg Gly Pro Ala Thr Phe
1 5

<210> SEQ ID NO 47
<211> LENGTH: 9
<212> TYPE: PRT
<213> ORGANISM: Influenza A virus

<400> SEQUENCE: 47

Ala Ile Leu Ser Leu Gln Thr Phe Asp
1 5

<210> SEQ ID NO 48
<211> LENGTH: 9
<212> TYPE: PRT
<213> ORGANISM: Influenza A virus

<400> SEQUENCE: 48

Ala Leu Ser Ser Ile Arg Val Ser Ser
1 5

<210> SEQ ID NO 49
<211> LENGTH: 9
<212> TYPE: PRT
<213> ORGANISM: Influenza A virus

<400> SEQUENCE: 49

Phe Ser Met Met Leu Leu Ser Met Ile
1 5

<210> SEQ ID NO 50
<211> LENGTH: 8
<212> TYPE: PRT
<213> ORGANISM: Influenza A virus

<400> SEQUENCE: 50

Ser Pro Pro Met Arg Thr Pro Thr
1 5

<210> SEQ ID NO 51
<211> LENGTH: 10
<212> TYPE: PRT
<213> ORGANISM: Influenza A virus

<400> SEQUENCE: 51

Leu Ile Val Leu Ala Ile Tyr Arg Phe Cys
1 5 10

<210> SEQ ID NO 52
<211> LENGTH: 8
<212> TYPE: PRT
<213> ORGANISM: Influenza A virus

<400> SEQUENCE: 52

Ser Leu Arg Thr Phe Asp Leu Ala
1 5

<210> SEQ ID NO 53
<211> LENGTH: 9
<212> TYPE: PRT
<213> ORGANISM: Influenza A virus

<400> SEQUENCE: 53

Met Leu Phe Val Gln Ser Tyr Phe Gln
1 5

<210> SEQ ID NO 54
<211> LENGTH: 18
<212> TYPE: PRT
<213> ORGANISM: Clostridium tetani

<400> SEQUENCE: 54

Phe Lys Leu Gln Thr Met Val Lys Leu Phe Asn Arg Ile Lys Asn Asn
1 5 10 15

Val Ala

<210> SEQ ID NO 55
<211> LENGTH: 19
<212> TYPE: PRT
<213> ORGANISM: Clostridium tetani

<400> SEQUENCE: 55

Leu Gln Thr Met Val Lys Leu Phe Asn Arg Ile Lys Asn Asn Val Ala
1 5 10 15

Gly Gly Cys

<210> SEQ ID NO 56
<211> LENGTH: 838
<212> TYPE: DNA

<213> ORGANISM: Influenza A virus

<400> SEQUENCE: 56
ttaaataagc tgaaacgaga aagttcttat ctcttgctcc acttcaagca atagttgtaa 60
ggcttgcata aatgttattt gctcaaaact attctctgtt atcttcagtc tatgtctcac 120
ttcttcaatc aaccatctta tttcttcaaa cttctgactt aattgttctc gccattttcc 180
gtttctgttt tggagggagt ggaggtctcc cattctcatt actgcttctc caagcgaatc 240
tctgtagagt ttcagagact cgaactgtgt tatcattcca ttcaagtcct ccgatgagga 300
ccccaactgc atttttgaca tcctcatcag tatgtcctgg aagagaaggc aatggtgaaa 360
tttcgccaac aattgctccc tcttcggtga aagcccttag tagtattaga gtctccagcc 420
ggtcgaaaat cacactgaag ttcgctttca gtatgatgtt cttatccatg atcgcctggt 480
ccattctgat acaaagagag cctgccactt tctgcttggg catgagcatg aaccagtccc 540
ttgacatctc ctcaagagtc atgtcagtta ggtagcgcga agcaggtaca gaggcaatgg 600
tcattttaag tgcctcatcg gattcttcct tcagaatccg ctccactatc tgctttccag 660
cacgggtggc tgtctcgatg tccagaccaa gagtgctgcc tcttcctctt agggacttct 720
gatctcggcg aagccgatca aggaatgggg catcacccag ttcttggtct gcaaaccgtt 780
tgcggacatg ccaaagaaag cagtctacct gaaagcttga cacagtgttg gaatccat 838

<210> SEQ ID NO 57
<211> LENGTH: 848
<212> TYPE: DNA
<213> ORGANISM: Influenza A virus

<400> SEQUENCE: 57
tatcattaaa taagctgaaa tgagaaagtt cttatctcct gttccacttc aaacagcagt 60
tgtaatgctt gcatgaatgt tatttgttca aagctatttt ccgttgtttt tagtctgtgt 120
ctcacttctt caatcagcca tcttatctct tcaaactttt gacctagctg ttctcgccat 180
tttccgtttc tgttttggag taagtggagg tcccccattc tcattactgc ttctccaagc 240
gaatctctgt agatttttag agactcgaac tgtgttatca ttccattcaa gtcctccgat 300
gaggacccca attgcatttt tgacatcctc aatagtatgt cctggaaaag aaggcaatgg 360
tgagatttcg ccaacaattg ctccctcttc ggtgaaagcc cttagtaata ctatggtctc 420
tagtcggtca aaaatcacac tgaaattcgc tttcaatatg atgtttttct ccatgattgc 480
ctggtccatt ctgatgcaaa gaggtccttc cactttctgc ttgggcatta gcatgaacca 540
gtttcttgac aattcctcaa tagtcatgtc agttatgtat cgcgaagcag gtgtggagac 600
catggtcatt ttaagtgcct catcagattc ttctttcaga atcttttcta caatttgctt 660
tccaacatgg gtggctgctt tgatgtctag accgagagta ttgcctcttc cccttaggga 720
cctctgatct cggcgaagcc gatcaaggaa tggggcatca ctcagttctt ggtctacaac 780
ttgtttccgg atatgccaaa gaaagcaatc tacctggaaa cttgacacag tgttggaatc 840
cattatgt 848

<210> SEQ ID NO 58
<211> LENGTH: 85
<212> TYPE: PRT
<213> ORGANISM: Influenza A virus

<400> SEQUENCE: 58

Met Leu Phe Val Arg Asn Tyr Ser Leu Ser Leu Ser Ile Cys Ala Ala

-continued

```
1               5                   10                  15

Phe Leu Gln Leu Thr Thr Leu Phe Pro Gln Ile Ser Val Pro Ile Ala
            20                  25                  30

Leu Ala Thr Phe His Phe Cys Ser Gly Gly Ser Glu Gly Leu Pro Phe
        35                  40                  45

Ser Ser Gln Phe Leu Gln Ala Asn Leu Cys Ile Phe Ser Glu Thr Arg
    50                  55                  60

Thr Val Leu Pro Phe His Ser Ser Pro Pro Met Arg Thr Pro Thr Ala
65                  70                  75                  80

Phe Leu Thr Ser Ser
                85
```